US011452709B2

(12) United States Patent
Xue et al.

(10) Patent No.: US 11,452,709 B2
(45) Date of Patent: Sep. 27, 2022

(54) COMPOSITIONS AND METHODS FOR PREVENTING AND TREATING RADIATION-INDUCED BYSTANDER EFFECTS CAUSED BY RADIATION OR RADIOTHERAPY

(71) Applicant: The Regents of the University of Colorado, Denver, CO (US)

(72) Inventors: Ding Xue, Louisville, CO (US); Yu Peng, Beijing (CN); Man Zhang, Beijing (CN); Lingjun Zheng, Boulder, CO (US); Qian Liang, Beijing (CN); Hanzeng Li, Louisville, CO (US); Jau-Song Yu, Taoyuan (TW); Jeng-Ting Chen, Taoyuan (TW)

(73) Assignees: THE REGENTS OF THE UNIVERSITY OF COLORADO, A BODY CORPORATE, Denver, CO (US); TSINGHUA UNIVERSITY, Beijing (CN); CHANG GUNG UNIVERSITY, Taoyuan (TW)

(*) Notice: Subject to any disclaimer, the term of this patent is extended or adjusted under 35 U.S.C. 154(b) by 83 days.

(21) Appl. No.: 16/632,046

(22) PCT Filed: Jul. 17, 2018

(86) PCT No.: PCT/US2018/042569
§ 371 (c)(1),
(2) Date: Jan. 17, 2020

(87) PCT Pub. No.: WO2019/018451
PCT Pub. Date: Jan. 24, 2019

(65) Prior Publication Data
US 2020/0155502 A1 May 21, 2020

Related U.S. Application Data

(60) Provisional application No. 62/533,272, filed on Jul. 17, 2017.

(51) Int. Cl.
*A61K 31/353* (2006.01)
*A61K 31/336* (2006.01)
*A61K 31/4025* (2006.01)
*A61K 31/7048* (2006.01)

(52) U.S. Cl.
CPC .......... *A61K 31/353* (2013.01); *A61K 31/336* (2013.01); *A61K 31/4025* (2013.01); *A61K 31/7048* (2013.01)

(58) Field of Classification Search
CPC .................................................. A61K 31/353
USPC ........................................................ 514/422
See application file for complete search history.

(56) References Cited

U.S. PATENT DOCUMENTS

2010/0257636 A1 10/2010 Warpeha et al.
2012/0020902 A1 1/2012 Giuliani et al.

OTHER PUBLICATIONS

Patel, European Journal of Medicinal Chemistry 155 (2018) 889-904.*
Ozyurt, Free Radical Research, Oct. 2014; 48(10): 1247-1255.*
Lin, Radio therapy and Oncology, 2011, vol. 104,395-400.*
Zwicky, Biochemical Journal, 2002, vol. 367, 209-217.*
Ozyurt et Al., "Quercetin protects radiation-induced DNA damage and apoptosis in kidney and bladder tissues of rats", Free Radical Research, Aug. 14, 2014 (Aug. 14, 2014), vol. 48, 9 pp. 1247-1255.
Lin et al., "Combination of quercelin with radiotherapy enhances tumor radiosensitivity in vitro and in vivo", Radiotherapy and Oncology, Nov. 25, 2011 (Nov. 25, 2011), vol. 104, 15 pp. 395-400.
Zwicky et al., "Cathepsin B expression and down-regulation by gene silencing and antisense DNA in human chondrocytes", Biochemical Journal, Oct. 1, 2002 (Oct. 1, 2002). vol. 367, 9 pp. 209-217.
Gondi et al., "Cathepsin B as a Cancer Target', Expert Opinion on Therapeutic Targets", Jan. 8, 2013 (Jan. 8, 2013), vol. 17, 9 pp. 281-291.
Wang et al., "Quercetin, a flavonoid with anti-inflammatory activity, suppresses the development of abdominal aortic aneurysms in mice", European Journal of Pharmacology, Jun. 19, 2012 (Jun. 19, 2012). vol. 690, 9 pp. 133-141.
Alapati et al., "uPAR and cathepsin B knockdown inhibits radiation-induced PKC integrated integrin signaling to the cytoskeleton of glioma-initiating cells", International Journal of Oncology, May 24, 2012 (May 24, 2012). 12 pp. 599-610.
Piao et al., "Hyperoside Protects Cells against Gamma Ray Radiation-Induced Apoptosis in Hamster Lung Fibroblast", Natural Product Sciences, Jun. 2013, vol. 19, 2 pp. 127-136.
Written Opinion dated Jan. 30, 2019 in International Application No. PCT/US2018/042569, 11 pages.
International Preliminary Report on Patentability dated Jan. 21, 2020 in International Application No. PCT/US2018/042569, 12 pages.
International Search Report dated Jan. 30, 2019 in International Application No. PCT/US2018/042569, 5 pages.

* cited by examiner

*Primary Examiner* — Nizal S Chandrakumar
(74) *Attorney, Agent, or Firm* — Berg Hill Greenleaf Ruscitti, LLP

(57) ABSTRACT

The invention provides novel compositions and methods for the treatment of Radiation-Induced Bystander Effects (RIBE), resulting from radiation exposure. In one preferred embodiment the inventions includes novel therapeutic agents, including but not limited to quercetin and quercetin analogs, as well as E64, CA074, CA074Me, that interfere with the activity of Cathepsin B.

9 Claims, 23 Drawing Sheets

Specification includes a Sequence Listing.

COMPOSITIONS AND METHODS FOR PREVENTING AND TREATING RADIATION-INDUCED BYSTANDER EFFECTS CAUSED BY RADIATION OR RADIOTHERAPY

CROSS REFERENCE TO RELATED APPLICATION

This application is a national stage application under 35 U.S.C. 371 of PCT Application No. PCT/US18/42569 having an international filing date of Jul. 17, 2018, which designated the United States, which PCT application claimed the benefit of U.S. Application Ser. No. 62/533,272, filed Jul. 17, 2017, both of which are incorporated by reference in their entirety.

This International PCT Application claims the benefit of and priority to U.S. Provisional Application No. 62/533,272, filed Jul. 17, 2017. The entire specification and figures of the above-referenced application is hereby incorporated, in its entirety by reference.

GOVERNMENT INTEREST

This invention was made with Government support under grant number R35 GM118188 awarded by the National Institutes of Health (NIH). The U.S. Government has certain rights in this invention.

SEQUENCE LISTING

The instant application contains a Sequence Listing which has been submitted electronically in ASCII format and is hereby incorporated by reference in its entirety. Said ASCII copy, created on May 25, 2022, is named "90245-00022" and is 5 Kbytes in size.

TECHNICAL FIELD

The inventive technology generally relates to compositions and methods for preventing and alleviating side effects caused by exposure to radiation and radiotherapy. Specifically, the invention encompasses the identification, isolation, and characterization of novel molecular components and pathways involved in Radiation-Induced Bystander Effects (RIBE) in both human and animals. The inventive technology further includes methods and systems for the development and application of novel therapeutic compositions and treatments, as well as diagnostic methodologies to treat RIBE caused by radiation or radiotherapy.

BACKGROUND OF THE INVENTION

Radiation-Induced Bystander Effects (RIBE) refer to a unique process, in which factors released by irradiated cells or tissues exert effects on other parts of the animal not exposed to radiation, causing genomic instability, stress responses, and altered apoptosis or cell proliferation among others effects. RIBE is also a major factor in determining the efficacy and success of radiotherapy in cancer treatment, not only because it affects and causes damage in nonirradiated cells and tissues, resulting in all sorts of deleterious side effects (e.g. hair loss, fatigue, skin problems, and low blood counts), but also because it can affect irradiated cells through paracrine signaling and cause resistance of cancer cells to radiotherapy. There is so far, no effective way to reduce or prevent side effects caused by radiation and radiotherapy.

Despite important implications in radioprotection, radiation safety and radiotherapy, the molecular identities of RIBE factors and their mechanisms of action remain elusive. Identification of RIBE factors and understanding of how they act have been fundamental issues in cancer radiotherapy and radioprotection. Thus, there remains a substantial need in the art for the identification and characterization of the molecular components and signaling pathways involved in RIBE, as well as novel compositions and treatments to prevent and/or alleviate RIBE caused by exposure to radiation and radiotherapy.

SUMMARY OF THE INVENTION

The present invention identifies and characterizes CPR-4, a cathepsin B homolog, as a major RIBE factor that induces multiple, typical RIBE effects, including apoptosis inhibition and increased cell proliferation, lethality, stress response, and genomic DNA damage. In one embodiment, the present inventors demonstrate that radiation increases cpr-4 transcription and CPR-4 protein production and secretion through a p53/CEP-1-dependent mechanism. The secreted CPR-4 then induces multiple RIBE responses, either directly or indirectly, through regulating the activity of the DAF-2 insulin/IGF receptor that is critical for multiple conserved signaling pathways, from aging, stress response, metabolism, to apoptosis.

In another embodiment, the present inventors demonstrate that expression of human Cathepsin B (CTSB) is upregulated in response to irradiation and that it is also involved in UV-induced bystander effects in human cells. In a preferred embodiment, the inventive technology relates to compositions, systems, methods and therapeutic treatments as well as diagnostic methodologies to prevent and/or alleviate RIBE in humans caused by radiation exposure or radiotherapy. Additional embodiments may also be directed generally to cathepsin B in other animal systems as well as all homologs and variants thereof.

In another embodiment, the present inventors demonstrate that expression of human Insulin/IGF Receptor (INSR), a homologue of the C. elegans DAF-2 protein, is involved in Cathepsin B (CTSB)-induced RIBE in human and other cells and that the RIBE signaling pathways are conserved between C. elegans and humans. In a preferred embodiment, the inventive technology includes compositions, systems, methods and therapeutic treatments as well as diagnostic methodologies to prevent and/or alleviate RIBE in humans caused by radiation exposure or radiotherapy through the alteration of expression or activity of INSR. Additional embodiments may also be generally directed to altering the expression and/or activity of INSR in other animal systems as well as all homologs and variants thereof.

As described below, the present invention features compositions and methods for altering the expression or activity of one or more of a CPR-4, Cathepsin B (CTSB), CEP-1, p53, DAF-2, insulin/IGF receptor (INSR), PDK-1, and/or PDK1 kinase peptide or fragment thereof, for the treatment or prevention of diseases and conditions associated with the effects of radiation exposure, particularly RIBE.

In one aspect, the invention provides a method of ameliorating the effects of radiation exposure, including RIBE, on a cell, the method involving contacting the cell that has been irradiated with an agent that selectively alters the expression or activity of one or more of CPR-4, Cathepsin B (CTSB), CEP-1, p53, DAF-2, insulin/IGF receptor (INSR), PDK-1, and/or PDK1 kinase in the cell relative to an untreated control cell, thereby ameliorating the effects of radiation exposure or RIBE on the cell. In another aspect, the invention provides a method of ameliorating the effects of radiation exposure, including RIBE, on a cell, the method involving contacting the cell that has not been irradiated, with an agent that selectively alters the expression or activity of one or more of CPR-4, Cathepsin B (CTSB), CEP-1, p53, DAF-2, insulin/IGF receptor (INSR), PDK-1, and/or PDK1 kinase in the cell relative to an untreated control cell, thereby ameliorating the effects of radiation exposure or RIBE on the cell.

In yet another aspect, the invention provides a method of ameliorating the effects of radiation exposure on a subject (e.g., in a cell, tissue, or organ in a mammalian subject), the method involving administering to the subject an agent that selectively alters the expression or activity of one or more of a receptor of CPR-4, Cathepsin B (CTSB), CEP-1, p53, DAF-2, insulin/IGF receptor (INSR), PDK-1, and/or PDK1 kinase in a cell relative to an untreated control cell, thereby ameliorating the effects of radiation exposure, and in particular RIBE on the subject.

In yet another aspect, the invention provides a method of ameliorating the effects of radiation exposure on a subject (e.g., in a cell, tissue, or organ in a mammalian subject), the method involving administering to the subject an agent that selectively alters the expression or activity of one or more signal pathways involving: CPR-4, Cathepsin B (CTSB), CEP-1, p53, DAF-2, insulin/IGF receptor (INSR), PDK-1, and/or PDK1 kinase in the subject relative to an untreated control subject, thereby ameliorating the effects of radiation exposure, and in particular RIBE on the subject.

In yet another aspect, the invention provides a method of ameliorating the effects of radiation exposure on a subject (e.g., in a cell, tissue, or organ in a mammalian subject), the method involving administering to the subject an agent that selectively alters the expression or activity of one or more of CPR-4, Cathepsin B (CTSB), CEP-1, p53, DAF-2, insulin/IGF receptor (INSR), PDK-1, and/or PDK1 kinase in a subject relative to an untreated control subject, thereby ameliorating the effects of radiation exposure, and in particular RIBE on the subject.

Another aspect of the current invention provides compositions and methods for disrupting, altering, and/or inhibiting the expression of one or more of a CPR-4; CTSB; CEP-1; DAF-2; p53, Insulin/IGF receptors, PDK-1, and/or PDK1 kinase genes or their homologs/orthologs thereof. Another aspect of the current invention provides compositions and methods for disrupting, altering and/or inhibiting the expression of one or more of a CPR-4; CTSB; CEP-1; DAF-2; p53, Insulin/IGF receptors, PDK-1, and/or PDK1 kinase genes or their homologs/orthologs thereof, for the treatment or prevention of diseases and conditions associated with the effects of radiation exposure, particularly RIBE. In various embodiments, one or more target genes may be altered through CRISPR/Cas-9, Transcription activator-like effector nucleases (TALAN) or Zinc (Zn2+) finger nuclease systems.

In yet another embodiment, the inventive technology may include one or more markers that may be used for diagnostic purposes, as well as for therapeutic, drug screening and patient/tumor radiotherapy efficacy/susceptibility purposes as well as other purposes described herein. In certain embodiments, these markers may include markers for predicting radiosensitivity or radioresistance in a patient, cell, tissue, tumor and the like. Markers may include, but not be limited to CPR-4; CTSB; CEP-1; DAF-2; p53, Insulin/IGF receptors, PDK-1, and/or PDK1 kinase.

Another aspect of the invention may include the use of specific CTSB inhibitors to alleviate and/or interfere with RIBE induced by radiation exposure. In one preferred embodiment, such inhibitors may include: 1) CA074 [N-(1-3-trans-propylcarbamoyloxirane-2-carbonyl)-1-isoleucyl-1-proline], a selective inhibitor of CTSB; 2) CA074 methyl ester (CA074Me), a membrane-permeant proinhibitor for intracellular cathepsin B; and 3) E64 which is an epoxide that can irreversibly inhibit a wide range of cysteine peptidases, including cathepsin B. In one embodiment, an effective amount of one or more of the aforementioned CTSB inhibitors or derivatives may be administered to a patient prior to, during or after radiotherapy. Additional aspects of the invention may include methods and systems for therapeutic drug screens for novel inhibitors of RIBE. Analogs, and other compounds that are included in the invention include, but are not limited to: E-64, E-64a, E-64b, E-64c, E-64d, CA-074, CA-074 Me, CA-030, CA-028, Z-Phe-Phe-FMK, H-Arg-Lys-Leu-Trp-NH2, N-(1-Naphthalenylsulfonyl)-Ile-Trp-aldehyde, Z-Phe-Tyr(tBu)-diazomethylketone, Z-Phe-Tyr-aldehyde, and combinations thereof.

In one aspect, the invention provides pharmaceutical composition(s) for the treatment of radiation exposure, in particular RIBE, the composition containing an effective amount of one or more agents that selectively alters the expression or activity of one or more of a CPR-4, Cathepsin B (CTSB), CEP-1, p53, DAF-2, insulin/IGF receptor (INSR), PDK-1, and/or PDK1 kinase receptor in a cell, relative to a reference cell.

In another aspect, the invention provides a pharmaceutical composition(s) for the treatment of radiation exposure, in particular RIBE, the composition containing an effective amount of one or more agents that selectively alters the expression or activity of one or more of a CPR-4, Cathepsin B (CTSB), CEP-1, p53, DAF-2, insulin/IGF receptor (INSR), PDK-1, and/or PDK1 kinase peptide or fragment thereof in a cell, relative to a reference cell.

In yet another aspect, the invention provides a kit for treating radiation exposure, in particular RIBE, containing an effective amount of an agent that selectively alters the expression or activity of a CPR-4, Cathepsin B (CTSB), CEP-1, p53, DAF-2, insulin/IGF receptor (INSR), PDK-1, and/or PDK1 kinase receptor; or a CPR-4, Cathepsin B (CTSB), CEP-1, p53, DAF-2, insulin/IGF receptor (INSR), PDK-1, and/or PDK1 kinase peptide or fragment thereof in a cell and instructions for using the kit to treat radiation exposure, and in particular RIBE.

In various embodiments of any of the aspects delineated herein, the agent is an inhibitory nucleic acid molecule that is complementary to at least a portion of a CPR-4, Cathepsin B (CTSB), CEP-1, p53, DAF-2, insulin/IGF receptor (INSR), PDK-1, and/or PDK1 kinase receptor nucleic acid molecule; or a CPR-4, Cathepsin B (CTSB), CEP-1, p53, DAF-2, insulin/IGF receptor (INSR), PDK-1, and/or PDK1 kinase nucleic acid molecule.

In various embodiments of any of the aspects delineated herein, the agent is an antibody or fragment thereof that selectively binds to a CPR-4, Cathepsin B (CTSB), CEP-1, p53, DAF-2, insulin/IGF receptor (INSR), PDK-1, and/or PDK1 kinase receptor; or a CPR-4, Cathepsin B (CTSB), CEP-1, p53, DAF-2, insulin/IGF receptor (INSR), PDK-1, and/or PDK1 kinase peptide. In various embodiments, the antibody may be a monoclonal or polyclonal antibody.

In various embodiments of any of the aspects delineated herein, the agent is a small molecule that selectively binds to a CPR-4, Cathepsin B (CTSB), CEP-1, p53, DAF-2, insulin/IGF receptor (INSR), PDK-1, and/or PDK1 kinase receptor; or a CPR-4, Cathepsin B (CTSB), CEP-1, p53, DAF-2, insulin/IGF receptor (INSR), PDK-1, and/or PDK1 kinase peptide. In various embodiments, the small molecule may be a synthetic.

The invention also provides compositions and methods for the treatment of radiation exposure. As described below, the present invention features compositions and methods for administering a therapeutically effective amount of the compound quercetin, or an analog thereof, to inhibit the activity of a Cathepsin B (CTSB) peptide or fragment thereof, for the treatment or prevention of diseases and conditions associated with the effects of radiation exposure, particularly RIBE.

In one aspect, the invention provides a method of ameliorating the effects of radiation exposure, including RIBE, on a cell, the method involving contacting the cell that has been irradiated with a therapeutically effective amount of the compound quercetin, or an analog thereof, to inhibit activity of a Cathepsin B (CTSB) peptide or fragment thereof, in the cell relative to an untreated control cell, thereby ameliorating the effects of radiation exposure or RIBE on the cell.

In another aspect, the invention provides a method of ameliorating the effects of radiation exposure, including RIBE, on a cell, the method involving contacting the cell that has not been irradiated, with a therapeutically effective amount of the compound quercetin, or an analog thereof, to inhibit activity of a Cathepsin B (CTSB) peptide or fragment thereof, in the cell relative to an untreated control cell, thereby ameliorating the effects of radiation exposure or RIBE on the cell.

In yet another aspect, the invention provides a method of ameliorating the effects of radiation exposure on a subject (e.g., in a cell, tissue, or organ in a mammalian subject), the method involving administering to the subject a therapeutically effective amount of the compound quercetin, or an analog thereof, to inhibit activity of a Cathepsin B (CTSB) peptide or fragment thereof, in a subject relative to an untreated control subject, thereby ameliorating the effects of radiation exposure, and in particular RIBE on the subject.

In yet another aspect, the invention provides a method of ameliorating the effects of radiation exposure on a subject (e.g., in a cell, tissue, or organ in a mammalian subject), the method involving administering to the subject a therapeutically effective amount of the compound quercetin, or an analog thereof, prior to the administration of a dose of radiation, whether for therapeutic or diagnostic reasons, to inhibit activity of a Cathepsin B (CTSB) peptide or fragment thereof, in a subject, thereby ameliorating the effects of radiation exposure, and in particular RIBE on the subject.

In yet another aspect, the invention provides a method of ameliorating the effects of radiation exposure on a subject (e.g., in a cell, tissue, or organ in a mammalian subject), the method involving administering to the subject a therapeutically effective amount of the compound quercetin, or an analog thereof, to inhibit activity of a Cathepsin B (CTSB) peptide or fragment thereof, in a subject after the administration of a dose of radiation, or when symptoms of RIBE begin to manifest, thereby ameliorating the effects of radiation exposure, and in particular RIBE on the subject.

In one aspect, the invention provides pharmaceutical composition(s) for the treatment of radiation exposure, in particular RIBE, the composition containing an effective amount of one or more agents that selectively reduce the expression or activity of one or more of Cathepsin B (CTSB) peptides in a cell, relative to a reference cell. In a preferred embodiment, the pharmaceutical composition(s) may include a therapeutically effective amount of the compound quercetin, or an analog thereof, and/or a pharmaceutically acceptable salt.

In yet another aspect, the invention provides a kit for treating radiation exposure, in particular RIBE, containing an effective amount of an agent that selectively reduce the expression or activity of one or more of Cathepsin B (CTSB) peptides in a cell, relative to a reference cell. In a preferred embodiment, the pharmaceutical composition(s) may include a therapeutically effective amount of the compound quercetin, or an analog thereof, and/or a pharmaceutically acceptable salt.

Additional embodiments of the current inventive technology may include, but are not limited to:

1. A method for ameliorating radiation-induced bystander effects in a patient caused by exposure to radiation comprising administering to the patient a therapeutically effective amount of an agent that inhibits the activity or expression of protein CPR-4.
2. A method for ameliorating radiation-induced bystander effects in a patient caused by exposure to radiation as described in clause 1, wherein said agent is selected from the group consisting of: a CPR-4 synthetic inhibitor, a chemical, a nucleic acid molecule, an antibody or a biologically active fragment thereof, and an aptamer.
3. A method for ameliorating radiation-induced bystander effects in a patient caused by exposure to radiation as described in clause 2, wherein said nucleic acid molecule is selected from the group consisting of: an anti-sense oligonucleotide, an RNAi construct, a DNA enzyme, and a ribozyme that specifically inhibits the expression or activity of CPR-4.
4. A method for ameliorating radiation-induced bystander effects in a patient caused by exposure to radiation as described in clause 2, wherein said antibody or a biologically active fragment thereof comprises an antibody or a biologically active fragment thereof that specifically binds to CPR-4.
5. A method for ameliorating radiation-induced bystander effects in a patient caused by exposure to radiation as described in clause 2, wherein said aptamer comprises an aptamer that specifically binds to CPR-4.
6. A method for ameliorating radiation-induced bystander effects in a patient caused by exposure to radiation as described in clause 1-5, wherein said agent is administered to the subject in a pharmaceutical composition.
7. A method for ameliorating radiation-induced bystander effects in a patient caused by exposure to radiation as described in clause 1, wherein the radiation therapy is combined with an anti-cancer therapy.
8. A method for ameliorating radiation-induced bystander effects in a patient caused by exposure to radiation as described in clause 7, wherein the anticancer therapy is selected from the group consisting of surgery and chemotherapy.
9. A method for ameliorating radiation-induced bystander effects in a patient caused by exposure to radiation as described in clause 1, wherein the agent is administered prior to the administration of the radiotherapy.
10. A method for ameliorating radiation-induced bystander effects in a patient caused by exposure to radiation as described in clause 1, wherein the agent is administered along with the administration of the radiotherapy.
11. A method for ameliorating radiation-induced bystander effects in a patient caused by exposure to radiation comprising administering to the patient a therapeutically effective amount of an agent that inhibits the secretion of protein CPR-4 from a cell.

12. A method for ameliorating radiation-induced bystander effects in a patient caused by exposure to radiation as described in clause 11, wherein said agent is selected from the group consisting of: a CPR-4 synthetic inhibitor, a nucleic acid molecule, an antibody or a biologically active fragment thereof, and an aptamer.

13. A method for ameliorating radiation-induced bystander effects in a patient caused by exposure to radiation as described in clause 12, wherein said nucleic acid molecule is selected from the group consisting of: an anti-sense oligonucleotide, an RNAi construct, a DNA enzyme, and a ribozyme that specifically inhibits the expression or activity of CPR-4.

14. A method for ameliorating radiation-induced bystander effects in a patient caused by exposure to radiation as described in clause 12, wherein said antibody or a biologically active fragment thereof comprises an antibody or a biologically active fragment thereof that specifically binds to CPR-4 and prevents secretion from said cell.

15. A method for ameliorating radiation-induced bystander effects in a patient caused by exposure to radiation as described in clause 12, wherein said aptamer comprises an aptamer that specifically binds to CPR-4 and prevents secretion from said cell.

16. A method for ameliorating radiation-induced bystander effects in a patient caused by exposure to radiation as described in clause 11-15, wherein said agent is administered to the subject in a pharmaceutical composition.

17. A method for ameliorating radiation-induced bystander effects in a patient caused by exposure to radiation as described in clause 11, wherein the radiation therapy is combined with an anti-cancer therapy.

18. A method for ameliorating radiation-induced bystander effects in a patient caused by exposure to radiation as described in clause 17, wherein the anti-cancer therapy is selected from the group consisting of surgery and chemotherapy.

19. A method for ameliorating radiation-induced bystander effects in a patient caused by exposure to radiation as described in clause 11, wherein the agent is administered prior to the administration of the radiotherapy.

20. A method for ameliorating radiation-induced bystander effects in a patient caused by exposure to radiation as described in clause 11, wherein the agent is administered along with the administration of the radiotherapy.

21. A method for ameliorating radiation-induced bystander effects in a patient caused by exposure to radiation, comprising administering to the patient a therapeutically effective amount of an agent that inhibits the activity or expression of protein Cathepsin B (CTSB).

22. A method for ameliorating radiation-induced bystander effects in a patient caused by exposure to radiation as described in clause 21, wherein said agent is selected from the group consisting of: a Cathepsin B (CTSB) synthetic inhibitor, a nucleic acid molecule, an antibody or a biologically active fragment thereof, and an aptamer.

23. A method for ameliorating radiation-induced bystander effects in a patient caused by exposure to radiation as described in clause 22, wherein said nucleic acid molecule is selected from the group consisting of: an anti-sense oligonucleotide, an RNAi construct, a DNA enzyme, and a ribozyme that specifically inhibits the expression or activity of Cathepsin B (CTSB).

24. A method for ameliorating radiation-induced bystander effects in a patient caused by exposure to radiation as described in clause 22, wherein said antibody or a biologically active fragment thereof comprises an antibody or a biologically active fragment thereof that specifically binds to Cathepsin B (CTSB).

25. A method for ameliorating radiation-induced bystander effects in a patient caused by exposure to radiation as described in clause 22, wherein said aptamer comprises an aptamer that specifically binds to Cathepsin B (CTSB).

26. A method for ameliorating radiation-induced bystander effects in a patient caused by exposure to radiation as described in clause 21-25, wherein said agent is administered to the subject in a pharmaceutical composition.

27. A method for ameliorating radiation-induced bystander effects in a patient caused by exposure to radiation as described in clause 21, wherein the radiation therapy is combined with an anti-cancer therapy.

28. A method for ameliorating radiation-induced bystander effects in a patient caused by exposure to radiation as described in clause 27, wherein the anti-cancer therapy is selected from the group consisting of surgery and chemotherapy.

29. A method for ameliorating radiation-induced bystander effects in a patient caused by exposure to radiation as described in clause 21, wherein the agent is administered prior to the administration of the radiotherapy.

30. A method for ameliorating radiation-induced bystander effects in a patient caused by exposure to radiation as described in clause 21, wherein the agent is administered along with the administration of the radiotherapy.

31. A method for ameliorating radiation-induced bystander effects in a patient caused by exposure to radiation comprising administering to the patient a therapeutically effective amount of an agent that inhibits the activity or expression of protein CEP-1.

32. A method for ameliorating radiation-induced bystander effects in a patient caused by exposure to radiation as described in clause 31, wherein said agent is selected from the group consisting of: a CEP-1 synthetic inhibitor, a chemical, a nucleic acid molecule, an antibody or a biologically active fragment thereof, and an aptamer.

33. A method for ameliorating radiation-induced bystander effects in a patient caused by exposure to radiation as described in clause 32, wherein said nucleic acid molecule is selected from the group consisting of: an anti-sense oligonucleotide, an RNAi construct, a DNA enzyme, and a ribozyme that specifically inhibits the expression or activity of CEP-1.

34. A method for ameliorating radiation-induced bystander effects in a patient caused by exposure to radiation as described in clause 32, wherein said antibody or a biologically active fragment thereof comprises an antibody or a biologically active fragment thereof that specifically binds to CEP-1.

35. A method for ameliorating radiation-induced bystander effects in a patient caused by exposure to radiation as described in clause 32, wherein said aptamer comprises an aptamer that specifically binds to CEP-1.
36. A method for ameliorating radiation-induced bystander effects in a patient caused by exposure to radiation as described in clause 31-35, wherein said agent is administered to the subject in a pharmaceutical composition.
37. A method for ameliorating radiation-induced bystander effects in a patient caused by exposure to radiation as described in clause 31, wherein the radiation therapy is combined with an anti-cancer therapy.
38. A method for ameliorating radiation-induced bystander effects in a patient caused by exposure to radiation as described in clause 37, wherein the anti-cancer therapy is selected from the group consisting of surgery and chemotherapy.
39. A method for ameliorating radiation-induced bystander effects in a patient caused by exposure to radiation as described in clause 31, wherein the agent is administered prior to the administration of the radiotherapy.
40. A method for ameliorating radiation-induced bystander effects in a patient caused by exposure to radiation as described in clause 31, wherein the agent is administered along with the administration of the radiotherapy.
41. A method for ameliorating radiation-induced bystander effects in a patient caused by exposure to radiation comprising administering to the patient a therapeutically effective amount of an agent that inhibits the activity or expression of protein DAF-2.
42. A method for ameliorating radiation-induced bystander effects in a patient caused by exposure to radiation as described in clause 41, wherein said agent is selected from the group consisting of: a DAF-2 synthetic inhibitor, a nucleic acid molecule, an antibody or a biologically active fragment thereof, and an aptamer.
43. A method for ameliorating radiation-induced bystander effects in a patient caused by exposure to radiation as described in clause 42, wherein said nucleic acid molecule is selected from the group consisting of: an anti-sense oligonucleotide, an RNAi construct, a DNA enzyme, and a ribozyme that specifically inhibits the expression or activity of DAF-2.
44. A method for ameliorating radiation-induced bystander effects in a patient caused by exposure to radiation as described in clause 42, wherein said antibody or a biologically active fragment thereof comprises an antibody or a biologically active fragment thereof that specifically binds to DAF-2.
45. A method for ameliorating radiation-induced bystander effects in a patient caused by exposure to radiation as described in clause 42, wherein said aptamer comprises an aptamer that specifically binds to DAF-2.
46. A method for ameliorating radiation-induced bystander effects in a patient caused by exposure to radiation as described in clause 41-45, wherein said agent is administered to the subject in a pharmaceutical composition.
47. A method for ameliorating radiation-induced bystander effects in a patient caused by exposure to radiation as described in clause 41, wherein the radiation therapy is combined with an anti-cancer therapy.
48. A method for ameliorating radiation-induced bystander effects in a patient caused by exposure to radiation as described in clause 47, wherein the anti-cancer therapy is selected from the group consisting of surgery and chemotherapy.
49. A method for ameliorating radiation-induced bystander effects in a patient caused by exposure to radiation as described in clause 41, wherein the agent is administered prior to the administration of the radiotherapy.
50. A method for ameliorating radiation-induced bystander effects in a patient caused by exposure to radiation as described in clause 41, wherein the agent is administered along with the administration of the radiotherapy.
51. A method for ameliorating radiation-induced bystander effects in a patient caused by exposure to radiation comprising administering to the patient a therapeutically effective amount of an agent that inhibits the activity or expression of protein PDK-1.
52. A method for ameliorating radiation-induced bystander effects in a patient caused by exposure to radiation as described in clause 51, wherein said agent is selected from the group consisting of: a PDK-1 synthetic inhibitor, a nucleic acid molecule, an antibody or a biologically active fragment thereof, and an aptamer.
53. A method for ameliorating radiation-induced bystander effects in a patient caused by exposure to radiation as described in clause 52, wherein said nucleic acid molecule is selected from the group consisting of: an anti-sense oligonucleotide, an RNAi construct, a DNA enzyme, and a ribozyme that specifically inhibits the expression or activity of PDK-1.
54. A method for ameliorating radiation-induced bystander effects in a patient caused by exposure to radiation as described in clause 52, wherein said antibody or a biologically active fragment thereof comprises an antibody or a biologically active fragment thereof that specifically binds to PDK-1.
55. A method for ameliorating radiation-induced bystander effects in a patient caused by exposure to radiation as described in clause 52, wherein said aptamer comprises an aptamer that specifically binds to PDK-1.
56. A method for ameliorating radiation-induced bystander effects in a patient caused by exposure to radiation as described in clause 51-55, wherein said agent is administered to the subject in a pharmaceutical composition.
57. A method for ameliorating radiation-induced bystander effects in a patient caused by exposure to radiation as described in clause 51, wherein the radiation therapy is combined with an anti-cancer therapy.
58. A method for ameliorating radiation-induced bystander effects in a patient caused by exposure to radiation as described in clause 57, wherein the anti-cancer therapy is selected from the group consisting of surgery and chemotherapy.
59. A method for ameliorating radiation-induced bystander effects in a patient caused by exposure to radiation as described in clause 51, wherein the agent is administered prior to the administration of the radiotherapy.

60. A method for ameliorating radiation-induced bystander effects in a patient caused by exposure to radiation as described in clause 51, wherein the agent is administered along with the administration of the radiotherapy.
61. A method for ameliorating radiation-induced bystander effects comprising the step of contacting at least one cell with an agent that selectively alters the expression or activity of one or more of a CPR-4, Cathepsin B (CTSB), CEP-1, p53, DAF-2, insulin/IGF receptor(s), PDK-1 and/or PDK1 kinase receptor in the cell, thereby ameliorating the effects of radiation exposure on the cell.
62. A method for ameliorating radiation-induced bystander effects comprising the step of contacting the cell with an agent that selectively alters the expression or activity of one or more of a CPR-4, Cathepsin B (CTSB), CEP-1, p53, DAF-2, insulin/IGF receptor(s), PDK-1 and/or PDK1 kinase peptide in the cell, thereby ameliorating the effects of radiation exposure on the cell.
63. A method for ameliorating radiation-induced bystander effects as described in clause 61, wherein the effect of radiation exposure is direct or indirect.
64. A method for ameliorating radiation-induced bystander effects as described in clause 63, wherein the cell is not exposed to radiation.
65. A method for ameliorating radiation-induced bystander effects as described in clause 63, wherein the cell is contacted with a cell or product of a cell that has been exposed to radiation.
66. A method for ameliorating radiation-induced bystander effects as described in clause 63, wherein the cell is in the vicinity or at a distance of and not in direct contact with a cell that has been exposed to radiation.
67. A method for ameliorating radiation-induced bystander effects as described in clause 61, wherein the cell and cell exposed to radiation are present in a subject.
68. A method for ameliorating radiation-induced bystander effects as described in clause 61, further comprising the step of ameliorating RIBE in a human.
69. A method for ameliorating radiation-induced bystander effects as described in clause 61, wherein the agent is an inhibitory nucleic acid molecule that is complementary to at least a portion of a CPR-4, Cathepsin B (CTSB), CEP-1, p53, DAF-2, insulin/IGF receptor(s), PDK-1 and/or PDK1 kinase nucleic acid molecule.
70. A method for ameliorating radiation-induced bystander effects as described in clause 69, wherein the inhibitory nucleic acid molecule is selected from the group consisting of an antisense molecule, an siRNA, an shRNA, other RNAi construct, a ribozyme, or a DNA product.
71. A method for ameliorating radiation-induced bystander effects as described in clause 61, wherein the agent is an antibody or fragment thereof that selectively binds to a CPR-4, Cathepsin B (CTSB), CEP-1, p53, DAF-2, insulin/IGF receptor(s), PDK-1 and/or PDK1 kinase receptor; or a CPR-4, Cathepsin B (CTSB), CEP-1, p53, DAF-2, insulin/IGF receptor(s), PDK-1 and/or PDK1 kinase peptide.
72. A method for ameliorating radiation-induced bystander effects as described in clause 71, wherein the antibody is a monoclonal or polyclonal antibody.
73. A method for ameliorating radiation-induced bystander effects as described in clause 61, wherein the method reduces RIBE.
74. A method for ameliorating radiation-induced bystander effects as described in clause 61, wherein the method increases the effectiveness of radiotherapy in a cancer subject.
75. A method for ameliorating radiation-induced bystander effects as described in clause 61, wherein the method reduces resistance of cancer cells to chemotherapy.
76. A method for ameliorating radiation-induced bystander effects comprising the step of contacting at least one cell with an agent that selectively alters the expression or activity of one or more of a CPR-4, Cathepsin B (CTSB), CEP-1, p53, DAF-2, insulin/IGF receptor(s), PDK-1 and/or PDK1 kinase peptide in the cell, thereby ameliorating the effects of radiation exposure on the cell.
77. A method for ameliorating radiation-induced bystander effects comprising the step of contacting the cell with an agent that selectively alters the expression or activity of one or more of a CPR-4, Cathepsin B (CTSB), CEP-1, p53, DAF-2, insulin/IGF receptor(s), PDK-1 and/or PDK1 kinase receptor in the cell, thereby ameliorating the effects of radiation exposure on the cell.
78. A method for ameliorating radiation-induced bystander effects as described in clause 76, wherein the effect of radiation exposure is direct or indirect.
79. A method for ameliorating radiation-induced bystander effects as described in clause 78, wherein the cell is not exposed to radiation.
80. A method for ameliorating radiation-induced bystander effects as described in clause 78, wherein the cell is contacted with a cell or product of a cell that has been exposed to radiation.
81. A method for ameliorating radiation-induced bystander effects as described in clause 78, wherein the cell is in the vicinity or at a distance of and not in direct contact with a cell that has been exposed to radiation.
82. A method for ameliorating radiation-induced bystander effects as described in clause 76, wherein the cell and cell exposed to radiation are present in a subject.
83. A method for ameliorating radiation-induced bystander effects as described in clause 76, wherein the effect of radiation exposure comprises RIBE.
84. A method for ameliorating radiation-induced bystander effects as described in clause 76, wherein the agent is an inhibitory nucleic acid molecule that is complementary to at least a portion of a CPR-4, Cathepsin B (CTSB), CEP-1, p53, DAF-2, insulin/IGF receptor(s), PDK-1 and/or PDK1 kinase nucleic acid molecule.
85. A method for ameliorating radiation-induced bystander effects as described in clause 84, wherein the inhibitory nucleic acid molecule is selected from the group consisting of an antisense molecule, an RNAi, an siRNA, an shRNA, a ribozyme, other RNAi construct, or a DNA product.
86. A method for ameliorating radiation-induced bystander effects as described in clause 76, wherein the agent is an antibody or fragment thereof that selectively binds to a CPR-4, Cathepsin B (CTSB), CEP-1, p53, DAF-2, insulin/IGF receptor(s), PDK-1 and/or PDK1 kinase receptor; or a CPR-4, Cathepsin B (CTSB), CEP-1, p53, DAF-2, insulin/IGF receptor(s), PDK-1 and/or PDK1 kinase peptide.
87. A method for ameliorating radiation-induced bystander effects as described in clause 86, wherein the antibody is a monoclonal or polyclonal antibody.
88. A method for ameliorating radiation-induced bystander effects as described in clause 76, wherein the method reduces RIBE.
89. The A method for ameliorating radiation-induced bystander effects as described in clause 76, wherein the method increases the effectiveness of radiotherapy in a cancer subject.
90. A method for ameliorating radiation-induced bystander effects as described in clause 76, wherein the method increases the effectiveness of chemotherapy in a cancer subject.
91. A method for ameliorating radiation-induced bystander effects as described in clause 76, wherein the method reduces resistance of cancer cells to chemotherapy.
92. A method of ameliorating the effects of radiation exposure in a subject, the method comprising administering to the subject an agent that selectively alters the expression or activity of one or more of a CPR-4, Cathepsin B (CTSB), CEP-1, p53, DAF-2, insulin/IGF receptor(s), PDK-1 and/or PDK1 kinase peptide in a subject thereby, ameliorating the radiation-induced bystander effects in the subject.
93. A method of ameliorating the effects of radiation exposure in a subject, the method comprising administering to the subject an agent that selectively alters the expression or activity of one or more of a CPR-4, Cathepsin B (CTSB), CEP-1, p53, DAF-2, insulin/IGF receptor(s), PDK-1 and/or PDK1 kinase receptor in a subject, thereby ameliorating the radiation-induced bystander effects in the subject.
94. A method of ameliorating the effects of radiation exposure in a subject, the method comprising administering to the subject an agent that selectively alters the expression or activity of one or more of a CPR-4, Cathepsin B (CTSB), CEP-1, p53, DAF-2, insulin/IGF receptor(s), PDK-1 and/or PDK1 kinase oligonucleotide in a subject, thereby ameliorating the radiation-induced bystander effects in the subject.
95. A method of ameliorating the effects of radiation exposure in a subject, the method comprising administering to the subject an agent that selectively alters the expression or activity of one or more of a CPR-4, Cathepsin B (CTSB), CEP-1, p53, DAF-2, insulin/IGF receptor(s), PDK-1 and/or PDK1 kinase ribonucleotide in a subject, thereby ameliorating the radiation-induced bystander effects in the subject.
96. A method of ameliorating the effects of radiation exposure in a subject, as described in clause 92, wherein the radiation exposure is direct or indirect.
97. A method of ameliorating the effects of radiation exposure in a subject, as described in clause 96, wherein the cell is not exposed to radiation.
98. A method of ameliorating the effects of radiation exposure in a subject, as described in clause 96, wherein the cell is contacted with a cell that has been exposed to radiation.
99. A method of ameliorating the effects of radiation exposure in a subject, as described in clause 96, wherein the cell is in the vicinity or at a distance of and not in direct contact with a cell that has been exposed to radiation.
100. A method of ameliorating the effects of radiation exposure in a subject, as described in clause 98, wherein the cell and cell exposed to radiation are present in the subject.
101. A method of ameliorating the effects of radiation exposure in a subject, as described in clause 92, wherein the effect of radiation exposure comprises RIBE.
102. A method of ameliorating the effects of radiation exposure in a subject, as described in clause 92, wherein the agent is an inhibitory nucleic acid molecule that is complementary to at least a portion of a CPR-4, Cathepsin B (CTSB), CEP-1, p53, DAF-2, insulin/IGF receptor(s), PDK-1 and/or PDK1 kinase receptor nucleic acid molecule; or a CPR-4, Cathepsin B (CTSB), CEP-1, p53, DAF-2, insulin/IGF receptor(s), PDK-1 and/or PDK1 kinase nucleic acid molecule.
103. A method of ameliorating the effects of radiation exposure in a subject, as described in clause 102, wherein the inhibitory nucleic acid molecule is selected from the group consisting of an antisense molecule, an RNAi, an siRNA, an shRNA, a ribozyme, other RNAi construct, or a DNA product.
104. A method of ameliorating the effects of radiation exposure in a subject, as described in clause 92, wherein the agent is an antibody or fragment thereof that selectively binds to a CPR-4, Cathepsin B (CTSB), CEP-1, p53, DAF-2, insulin/IGF receptor(s), PDK-1 and/or PDK1 kinase receptor; or an CPR-4, Cathepsin B (CTSB), CEP-1, p53, DAF-2, insulin/IGF receptor(s), PDK-1 and/or PDK1 kinase peptide.
105. A method of ameliorating the effects of radiation exposure in a subject, as described in clause 104, wherein the antibody is a monoclonal or polyclonal antibody.
106. A method of ameliorating the effects of radiation exposure in a subject, as described in clause 92, wherein the method reduces RIBE.
107. A method of ameliorating the effects of radiation exposure in a subject, as described in clause 92, wherein the method increases the effectiveness of radiotherapy in a cancer subject.
108. A method of ameliorating the effects of radiation exposure in a subject, as described in clause 92, wherein the method increases the effectiveness of chemotherapy in a cancer subject.
109. A method of ameliorating the effects of radiation exposure in a subject, as described in clause 92, wherein the method reduces resistance of cancer cells to chemotherapy.
110. A pharmaceutical composition for the treatment of radiation exposure, the composition comprising a therapeutically-effective amount of one or more agents that selectively alters the expression or activity of a CPR-4, Cathepsin B (CTSB), CEP-1, p53, DAF-2, insulin/IGF receptor(s), PDK-1 and/or PDK1 kinase peptide in a cell, thereby ameliorating the radiation-induced bystander effects in the subject.
111. A pharmaceutical composition for the treatment of radiation exposure, the composition comprising a therapeutically-effective amount of one or more agents that selectively alters the expression or activity of a CPR-4, Cathepsin B (CTSB), CEP-1, p53, DAF-2, insulin/IGF receptor(s), PDK-1 and/or PDK1 kinase receptor in a cell, thereby ameliorating the radiation-induced bystander effects in the subject.

112. The pharmaceutical composition of clause 110 wherein at least one agent is an inhibitory nucleic acid molecule siRNA that is complementary to at least a portion of a CPR-4, CTSB, CEP-1, p53, DAF-2, PDK-1 and/or PDK1 kinase receptor nucleic acid molecule; or a CPR-4, Cathepsin B (CTSB), CEP-1, p53, DAF-2, insulin/IGF receptor(s), PDK-1 and/or PDK1 kinase nucleic acid molecule.

113. The pharmaceutical composition of clause 112, wherein the inhibitory nucleic acid molecule is selected from then group consisting of an antisense molecule, an siRNA, an shRNA, a ribozyme, other RNAi construct, or a DNA product.

114. The pharmaceutical composition of clause 111, wherein at least one agent is an antibody or fragment thereof that selectively binds to a CPR-4, Cathepsin B (CTSB), CEP-1, p53, DAF-2, insulin/IGF receptor(s), PDK-1 and/or PDK1 kinase receptor; CPR-4, Cathepsin B (CTSB), CEP-1, p53, DAF-2, insulin/IGF receptor(s), PDK-1 and/or PDK1 kinase peptide.

115. The pharmaceutical composition of clause 114, wherein the antibody is monoclonal or polyclonal.

116. The pharmaceutical composition of clause 110, wherein the agent alters cell death, reduces DNA damage, or increases DNA repair in the subject.

117. The pharmaceutical composition of clause 110, wherein the method reduces RIBE in a patient.

118. The pharmaceutical composition of clause 110, wherein the composition increases the effectiveness of radiotherapy in a cancer subject in a patient.

119. The pharmaceutical composition of clause 110, wherein the composition increases the effectiveness of chemotherapy in a cancer subject in a patient.

120. The pharmaceutical composition of clause 110, wherein the composition reduces resistance of cancer cells to chemotherapy in a patient.

121. A kit for treating radiation exposure comprising an effective amount of an agent that selectively alters the expression or activity of a CPR-4, Cathepsin B (CTSB), CEP-1, p53, DAF-2, insulin/IGF receptor(s), PDK-1 and/or PDK1 kinase receptor; or a CPR-4, Cathepsin B (CTSB), CEP-1, p53, DAF-2, insulin/IGF receptor(s), PDK-1 and/or PDK1 kinase peptide in a cell and instructions for using the kit to treat radiation exposure.

122. The kit of clause 121, wherein the agent is an inhibitory nucleic acid molecule that is complementary to at least a portion of a CPR-4, Cathepsin B (CTSB), CEP-1, p53, DAF-2, insulin/IGF receptor(s), PDK-1 and/or PDK1 kinase receptor nucleic acid molecule; or a CPR-4, Cathepsin B (CTSB), CEP-1, p53, DAF-2, insulin/IGF receptor(s), PDK-1 and/or PDK1 kinase nucleic acid molecule.

123. The kit of clause 122, wherein the inhibitory nucleic acid molecule is selected from the group consisting of an antisense molecule, an siRNA, an shRNA, a ribozyme, other RNAi construct, or a DNA product.

124. The kit of clause 121, wherein the agent is an antibody or fragment thereof that selectively binds CPR-4, Cathepsin B (CTSB), CEP-1, p53, DAF-2, insulin/IGF receptor(s), PDK-1 and/or PDK1 kinase receptor; or a CPR-4, Cathepsin B (CTSB), CEP-1, p53, DAF-2, insulin/IGF receptor(s), PDK-1 and/or PDK1 kinase peptide.

125. The kit of clause 124, wherein the antibody is monoclonal or polyclonal.

126. The kit of clause 121, wherein the method reduces RIBE in a patient.

127. The kit of clauses 121, wherein the kit increases the effectiveness of radiotherapy in a patient.

128. The kit of clauses 121, wherein the kit increases the effectiveness of chemotherapy in a patient 129. The kit of clauses 121, wherein the kit reduces resistance of cancer cells to chemotherapy in a patient.

130. A method of ameliorating the effects of radiation exposure in a subject, the method comprising selectively altering the expression of one or more of the following: CPR-4, Cathepsin B, CEP-1, p53, DAF-2, insulin/IGF receptors, PDK-1 and/or PDK1 kinase.

131. A method of ameliorating the effects of radiation exposure in a subject as described in clause 130 wherein said method comprises selectively altering the expression of CPR-4; Cathepsin B (CTSB); CEP-1; p53, DAF-2; insulin/IGF receptor(s), PDK-1 and/or PDK1 kinase in a patient through a system selected from the group consisting of: a CRISPR/Cas-9 system, a TALEN system, or a Zinc Finger Nuclease system.

132. A method of ameliorating the effects of radiation exposure in a subject as described in clause 130 wherein said subject is a human.

133. A method of ameliorating the effects of radiation exposure in a subject as described in clause 131 wherein said method of selectively altering the expression of CPR-4; Cathepsin B (CTSB); CEP-1; p53, DAF-2; insulin/IGF receptor(s), PDK-1 and/or PDK1 kinase through CRISPR/Cas-9 comprises the steps of exposing a subject to:
  at least one CRISPR-associated endonuclease and an isolated nucleic acid encoding a CRISPR-associated endonuclease; and
  at least one of a guide RNA and an isolated nucleic acid encoding a guide RNA, wherein the guide RNA is complementary to a target nucleic acid sequence in a cell.

134. A method of ameliorating the effects of radiation exposure in a subject as described in clause 133 wherein said CRISPR-associated endonuclease is Cas-9 endonuclease.

135. A method of ameliorating the effects of radiation exposure in a subject as described in clause 134 wherein said target nucleic acid sequence comprises a target nucleic acid sequence in CPR-4; Cathepsin B (CTSB); CEP-1; p53, DAF-2; insulin/IGF receptor(s) PDK-1, or PDK1 kinase.

136. A method of ameliorating the effects of radiation exposure in a subject as described in clause 135 wherein said target nucleic acid sequence in CPR-4; Cathepsin B (CTSB); CEP-1; p53, DAF-2; insulin/IGF receptor(s), PDK-1 and/or PDK1 kinase comprises a target sequence associated with a biological activity.

137. A method of ameliorating the effects of radiation exposure in a subject as described in clause 136, wherein said biological activity comprises a RIBE inducing biological activity.

138. A method for ameliorating radiation-induced bystander effects in a patient caused by exposure to radiation comprising administering to the patient a therapeutically effective amount of an agent that alters the activity or expression of RIBE inducing proteins.

139. A method for ameliorating radiation-induced bystander effects in a patient caused by exposure to radiation as described in clause 138, wherein said agent is a selective inhibitor of Cathepsin B (CTSB).

140. A method for ameliorating radiation-induced bystander effects in a patient caused by exposure to radiation as described in clause 139, wherein said selective inhibitor of Cathepsin B (CTSB) is CA074 [N-(1-3-trans-propylcarbamoyloxirane-2-carbonyl)-1-isoleucyl-1-proline].

141. A method for ameliorating radiation-induced bystander effects in a patient caused by exposure to radiation as described in clause 138, wherein said agent is a membrane-permeant proinhibitor for intracellular Cathepsin B (CTSB).

142. A method for ameliorating radiation-induced bystander effects in a patient caused by exposure to radiation as described in clause 141, wherein said membrane-permeant proinhibitor for intracellular Cathepsin B (CTSB) is CA074 methyl ester.

143. A method for ameliorating radiation-induced bystander effects in a patient caused by exposure to radiation as described in clause 138, wherein said agent is an epoxide that inhibits cysteine peptidases.

144. A method for ameliorating radiation-induced bystander effects in a patient caused by exposure to radiation as described in clause 143, wherein said epoxide that inhibits cysteine peptidases is E64.

145. A method for ameliorating radiation-induced bystander effects in a patient caused by exposure to radiation as described in clauses 138-144 wherein said patient is a human.

146. A method for ameliorating radiation-induced bystander effects in a patient caused by exposure to radiation as described in clauses 138-145 wherein said method exhibits one or more of the following: increases the effectiveness of radiotherapy in said patient; increases the effectiveness of chemotherapy in said patient; reduces resistance of cancer cells to radiotherapy in said patient; reduces resistance of cancer cells to chemotherapy in a patient; increases the patient's tolerance to radiotherapy.

147. A pharmaceutical composition for the treatment of RIBE, the composition comprising an effective amount one or more agents that selectively alters the expression or activity of Cathepsin B (CTSB).

148. A pharmaceutical composition for the treatment of RIBE as described in clause 147 wherein said one or more agents selectively inhibit and/or reduce the expression or activity of Cathepsin B (CTSB).

149. A pharmaceutical composition for the treatment of RIBE as described in clause 148 wherein said agent is selected from the group consisting of: E64, CA074, CA074 methyl ester, and their derivatives.

150. A method for determining if a cancer patient is predicted to respond to the administration of radiation therapy, the method comprising:
   detecting in a sample of cells from a patient, a level of gene expression of a marker gene or plurality of marker genes selected from the group consisting of:
   i. a marker gene having at least 85% sequence identify with Cathepsin B (CTSB) gene, or homologs or variants thereof;
   ii. a marker gene having at least 85% sequence identify with CPR-4 gene, or homologs or variants thereof;
   iii. a marker gene having at least 85% sequence identify with CEP-1 gene, or homologs or variants thereof;
   iv. a marker gene having at least 85% sequence identify with p53 gene, or homologs or variants thereof;
   v. a marker gene having at least 85% sequence identify with DAF-2 gene, or homologs or variants thereof;
   vi. a marker gene having at least 85% sequence identify with human Insulin/IGF Receptor (INSR) gene, or homologs or variants thereof;
   vii. a marker gene having at least 85% sequence identify with human PDK1 kinase gene, or homologs or variants thereof;
   viii. a polynucleotide which is fully complementary to at least a portion of a marker gene of i-vii;
   ix. polypeptides encoded by the marker genes of i-vii; and
   x. fragments of polypeptides of ix.
   wherein the expression levels of the markers are indicative of whether the patient will respond to the administration of radiation therapy.

151. The method of clause 150, wherein the presence of the marker or the plurality of markers is determined by detecting the presence of a polypeptide prior to radiotherapy, during radiotherapy and/or after radiotherapy.

152. The method of clause 150, wherein said patient is a human.

153. The method of clause 150, wherein said sample of cells is selected from the group consisting of: a non-cancerous cell, a cancer cell, a pre-cancerous cell, a tissue, and an organ.

154. A method for determining if a cancer patient is predicted to respond to the administration of radiation therapy, the method comprising:
   detecting in a sample of cells from a patient, a level of gene expression of a marker gene or plurality of marker genes selected from the group consisting of:
   i. a marker gene having at least 85% sequence identify with Cathepsin B (CTSB) gene, or homologs or variants thereof;
   ii. a marker gene having at least 85% sequence identify with CPR-4 gene, or homologs or variants thereof;
   iii. a marker gene having at least 85% sequence identify with CEP-1 gene, or homologs or variants thereof;
   iv. a marker gene having at least 85% sequence identify with p53 gene, or homologs or variants thereof;
   v. a marker gene having at least 85% sequence identify with DAF-2 gene, or homologs or variants thereof;
   vi. a marker gene having at least 85% sequence identify with human Insulin/IGF Receptor (INSR) gene, or homologs or variants thereof;
   vii. a marker gene having at least 85% sequence identify with human PDK1 kinase gene, or homologs or variants thereof;
   viii. a polynucleotide which is fully complementary to at least a portion of a marker gene of i-vii;
   ix. polypeptides encoded by the marker genes of i-vii; and
   x. fragments of polypeptides of ix.
   wherein the expression levels of the markers are indicative of whether the patient is susceptible to develop RIBE.

155. The method of clause 153, wherein the presence of the marker or the plurality of markers is determined by detecting the presence of a polypeptide prior to radiotherapy, during radiotherapy and/or after radiotherapy.

156. The method of clause 154, wherein said patient is a human.

157. The method of clause 154, wherein said sample of cells is selected from the group consisting of: a non-cancerous cell, a cancer cell, a pre-cancerous cell, a tissue, and organ.

158. A method of assessing the efficacy or effectiveness of a radiation treatment being administered to a cancer subject, the method comprising comparing:
the expression level of a marker measured in a first sample obtained from the subject at a time $t_o$, wherein the marker is selected from the group consisting of:
   i. a marker gene having at least 85% sequence identify with Cathepsin B (CTSB) gene, or homologs or variants thereof;
   ii. a marker gene having at least 85% sequence identify with CPR-4 gene, or homologs or variants thereof;
   iii. a marker gene having at least 85% sequence identify with CEP-1 gene, or homologs or variants thereof;
   iv. a marker gene having at least 85% sequence identify with p53 gene, or homologs or variants thereof;
   v. a marker gene having at least 85% sequence identify with DAF-2 gene, or homologs or variants thereof;
   vi. a marker gene having at least 85% sequence identify with human Insulin/IGF Receptor (INSR) gene, or homologs or variants thereof;
   vii. a marker gene having at least 85% sequence identify with human PDK1 kinase gene, or homologs or variants thereof;
   viii. a polynucleotide which is fully complementary to at least a portion of a marker gene of i-vii;
   ix. polypeptides encoded by the marker genes of i-vii; and
   x. fragments of polypeptides of ix.
the level of the marker in a second sample obtained from the subject at time $t_1$; and,
wherein a change in the level of the marker in the second sample relative to the first sample is an indication that the radiation treatment is effective for treating cancer in the subject.

159. The method of clause 158, wherein the time $t_o$ is before the treatment has been administered to the subject, and the time $t_1$ is after the treatment has been administered to the subject.

160. The method of clause 158, wherein said patient is a human.

161. The method of clause 158, wherein said sample of cells is selected from the group consisting of: a non-cancerous cell, a cancer cell, a pre-cancerous cell, a tissue, and organ.

162. A method of assessing the efficacy or effectiveness of a radiation treatment being administered to a cancer subject, the method comprising comparing:
the expression level of a marker measured in a first sample obtained from the subject at a time $t_o$, wherein the marker is selected from the group consisting of:
   xi. a marker gene having at least 85% sequence identify with Cathepsin B (CTSB) gene, or homologs or variants thereof;
   xii. a marker gene having at least 85% sequence identify with CPR-4 gene, or homologs or variants thereof;
   xiii. a marker gene having at least 85% sequence identify with CEP-1 gene, or homologs or variants thereof;
   xiv. a marker gene having at least 85% sequence identify with p53 gene, or homologs or variants thereof;
   xv. a marker gene having at least 85% sequence identify with DAF-2 gene, or homologs or variants thereof,
   xvi. a marker gene having at least 85% sequence identify with human Insulin/IGF Receptor (INSR) gene, or homologs or variants thereof;
   xvii. a marker gene having at least 85% sequence identify with human PDK1 kinase gene, or homologs or variants thereof,
   xviii. a polynucleotide which is fully complementary to at least a portion of a marker gene of i-vii;
   xix. polypeptides encoded by the marker genes of i-vii; and
   xx. fragments of polypeptides of ix.
the level of the marker in a second sample obtained from the subject at time $t_1$; and,
wherein a change in the level of the marker in the second sample relative to the first sample is an indication of whether the patient is susceptible to develop RIBE.

163. The method of clause 162, wherein the time $t_o$ is before the treatment has been administered to the subject, and the time $t_1$ is after the treatment has been administered to the subject.

164. The method of clause 163, and further comprising comparing successive radiotherapy treatments each comprising a higher dose of radiation.

165. The method of clause 164, and further comprising administering the optimal level of radiation to a patient, the optimal level being a level that will be a therapeutically effective dose and will induce no or limited RIBE effects in said patient.

166. The method of clause 165, wherein said patient is a human.

167. The method of clause 162, wherein said sample of cells is selected from the group consisting of: a non-cancerous cell, a cancer cell, a pre-cancerous cell, a tissue, and organ.

168. A method of screening for novel therapeutic inhibitors of RIBE comprising:
generating a RIBE-inducible transgenic nematode;
placing said transgenic nematode on a growth media containing one or more potential therapeutic target compounds; and
selecting target compounds that inhibit RIBE by selecting target compounds that decrease embryonic lethality and/or larval arrest in said transgenic nematode progeny.

169. The method of clause 168, wherein said step of generating a RIBE-inducible transgenic nematode comprises the step of generating a Pmyo-2::CPR-4::mCherry transgenic nematode or its equivalent or a transgenic nematode expressing CPR-4, CPR-4::mCherry, or its equivalent under the control of a *C. elegans* promoter.

170. The method of clause 168, wherein said selected potential therapeutic target compounds are further confirmed to inhibit RIBE through localized irradiation testing.
171. A method of screening for novel therapeutic inhibitors of RIBE comprising:
   generating a RIBE-inducible transgenic nematode;
   introducing one or more potential therapeutic target compounds to said transgenic nematode; and
   conducting localized irradiation testing on said transgenic nematode and/or its progeny.
172. The method of clause 171, wherein said step of generating a RIBE-inducible transgenic nematode comprises the step of generating a Pmyo-2::CPR-4::mCherry transgenic nematode or its equivalent.
173. The method of clause 171, and further comprising the step of:
   placing said transgenic nematode and/or it progeny on a growth media containing one or more potential therapeutic target compounds; and
   selecting target compounds that inhibit RIBE by selecting target compounds that decrease embryonic lethality and/or larval arrest in said transgenic nematode progeny.
174. A novel composition, method and/or system as described in any clause presented herein wherein said CPR-4; Cathepsin B (CTSB); CEP-1; p53, DAF-2; insulin/IGF receptor(s) PDK-1 or PDK1 kinase peptide comprise a homolog and/or ortholog and/or variant and/or fragment.
175. A method of screening for novel therapeutic modulators of RIBE comprising:
   generating a RIBE-inducible transgenic animal in an animal model;
   placing said transgenic animal on a growth media containing one or more potential therapeutic target compounds; and
   selecting target compounds that affect RIBE by selecting target compounds that affect some phenotypes, including embryonic lethality, larval arrest, genomic DNA damage, or other scorable phenotypes in said transgenic animal progeny.
176. A method of screening for novel therapeutic modulators of RIBE as described in clause 175 wherein said animal model is selected from the group consisting of: C. elegans, Drosophila, Zebrafish or other animal models.

Other features and advantages of the invention will be apparent from the figures, detailed description, and from the claims.

BRIEF DESCRIPTION OF THE FIGURES

This patent application file contains at least one drawing executed in color. Copies of this patent application publication with color drawing(s) will be provided by the Office upon request and payment of the necessary fee. Further, the above and other aspects, features, and advantages of the present disclosure will be better understood from the following detailed descriptions taken in conjunction with the accompanying figures, all of which are given by way of illustration only, and are not limiting the presently disclosed embodiments, in which.

MODE(S) FOR CARRYING OUT THE INVENTION(S)

Figure 1:
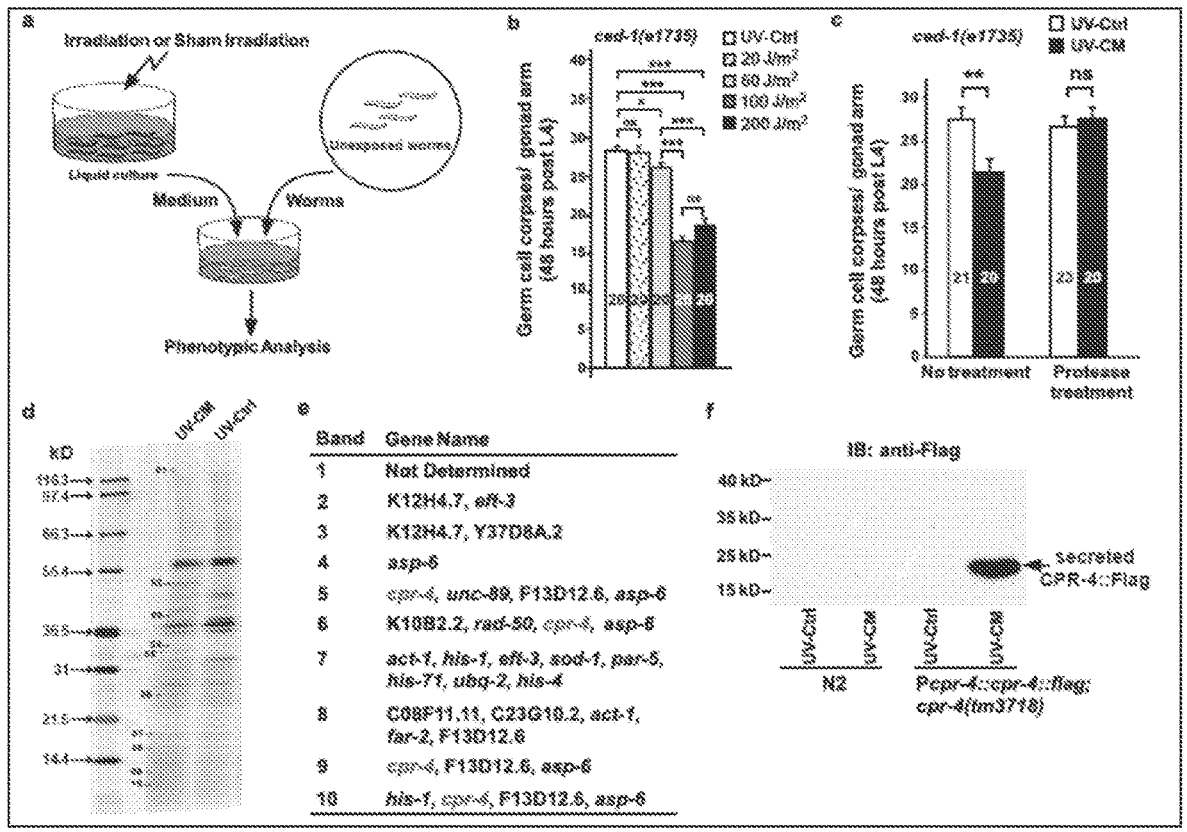
FIG. 1: Identification of the RIBE factor. (1a). Schematic presentation of the RIBE assay in C. elegans. (1b-c). Here ced-1(e1735) L4 larvae were cultured in UV-CM from N2 animals irradiated at the indicated dosage (b) or UV-CM (100 J/m$^2$) treated with Trypsin protease (50 ng/μL)(c). Germ cell corpses were scored after 48 hours. Data are mean±s.e.m. The numbers of gonad arms scored are indicated inside the bars. *P<0.05, P<0.01, *P<0.001, "ns", non-significant, two-sided, unpaired t test. (1d-e). Mass spectrometry analysis. Concentrated>10 kD UV-CM and UV-Ctrl fractions were resolved on SDS polyacrylamide gel (PAGE) and silver stained (d). Protein identities in bands unique to UV-CM (marked by numbers) are shown (e). (1f). CPR-4::Flag was secreted into UV-CM from Pcpr-4::cpr-4::flag animals. UV-CM and UV-Ctrl (1 μg/μL) were resolved on SDS PAGE and detected by immunoblotting (IB).

In one preferred embodiment, the present inventors have identified a novel and highly conserved cysteine protease CPR-4, a human cathepsin B homolog, as the first RIBE factor that induces multiple, typical RIBE effects, including apoptosis inhibition and increased cell proliferation, lethality, and stress response. In mammals, for example, it has been observed that cathepsin B is secreted from lysosomes to exert extracellular activities, including regulation of apoptosis, and plays roles in neoplastic and inflammatory disease states. Recent studies have also shown that extracellular cathepsin B enhances breast cancer resistance to drug-induced apoptosis during chemotherapy. Thus, CPR-4 and human cathepsin B (CTSB), among others discussed below, is both a novel biomarker of outcome prior to or following radiation therapy and a potential therapeutic target for improving the effects of radiation therapy.

The present inventors have further demonstrated radiation induced increases in cpr-4 transcription and CPR-4 protein production and secretion through a p53/CEP-1-dependent mechanism. The secreted CPR-4 then induces multiple RIBE responses, either directly or indirectly, through regulating the activity of the DAF-2 insulin/IGF receptor that is critical for multiple conserved signaling pathways, from aging, stress response, metabolism, to apoptosis. More specifically, the present inventors have shown that CPR-4 is secreted from animals or cells irradiated with ultraviolet (UV) or ionizing gamma rays (IR), and is a major factor in the conditioned medium that leads to inhibition of cell death and increased embryonic lethality in unirradiated animals.

The present inventors describe novel mechanisms, whereby CPR-4 causes these effects and stress responses at unexposed sites distal to the irradiated tissue. More specifically, the present inventors describe the pathway activity of CPR-4 being regulated by cep-1, a p53 tumor suppressor gene homolog, in response to radiation. The present inventors further describe the activity of CPR-4 as acting through DAF-2, an insulin-like growth factor receptor and its downstream PDK kinase to exert RIBE. The present inventors have also described a human cathepsin B (CTSB) cysteine protease that is also involved in RIBE responses in human cells. Specifically, it has been demonstrated that expression of Cathepsin B (CTSB) is upregulated in response to irradiation, and that it is also involved in UV-induced bystander effects in human cells.

The identification of cathepsin B; CPR-4; p53; cep-1; DAF-2; other insulin-like growth factor receptors; PDK-1 kinase, other PDK kinases, and the associated signal transduction pathways as novel mediators of RIBE in both human and animal systems, may provide new targets and/or markers for therapeutic development of methods that can enhance the efficacy of targeted cell killing and reduce or prevent side effects caused by radiation and radiotherapy.

As such, the inventive technology further relates to the generation of novel compositions and therapeutic methods to inhibit the target molecules and molecular pathways that give rise to RIBE in humans and other animals. Specifically, the inventive technology includes the identification and inhibition of one or more of the following mediators of RIBE: Cathepsin B (CTSB); CPR-4; p53; CEP-1; DAF-2; other insulin-like growth factor receptors; PDK-1 kinase, other PDK kinases; and their associated signal transduction pathways, including such predecessor and successor RIBE mediators (herein generally referred to as: targets, target peptide, target polynucleotide, target oligonucleotide, target polypeptide, target molecule(s), marker, biomarker, target marker). Additional embodiments may further include, identification and inhibition of one or more homologs or variants of the above identified RIBE mediators. In one preferred embodiment, the inventions identification and inhibition of Cathepsin B (CTSB), and/or its homolog CPR-4 by quercetin, isoquercetin and/or other quercetin analogs or derivatives.

These clinical and pharmaceutical applications, in particular the use of quercetin, isoquercetin and/or other quercetin analogs or derivatives as therapeutic agents to treat and/or prevent RIBE, may enhance the efficacy of targeted cell killing, and may reduce or prevent deleterious side effects caused by radiation and radiotherapy. Certain other embodiments of the invention may include diagnostics applications to quickly and effectively screen for new drugs that can enhance the efficacy of targeted cell killing and reduce or prevent side effects caused by radiation and radiotherapy and used for radioprotection. Such applications may be especially advantages for persons undergoing radiation therapy for cancer that may be at risk for RIBE. In addition, such therapeutic methods may be used to directly treat RIBE in patients exposed to radiation, prophylactically prior to a planned radiotherapy event, or in instances where the risk of radiation exposure may be high.

In one preferred embodiment, the present invention further relates to a therapeutic agent for the treatment and/or prevention of RIBE which comprises an active ingredient of quercetin and/or quercetin analogs/derivatives, more specifically, to a therapeutic agent for RIBE comprising an active ingredient of a quercetin and/or quercetin analog represented by the following general formula (I) shown below, and/or pharmaceutically acceptable salts or carriers wherein, R1 is gentiotriose, glucopyranose, O-arabinofuranose, O-diglucopyranose, O-galactopyranose, O-galactoside-gallate, O-gentiobiose, O-glucopyranose, O-glucuronide, O-neohesperidose, O-rhamnopyranose, O-rutinose, O-sophorose, O-xylopyranose, OCH3, OH, rhamnogentiobiose, rhamnoglucose or sulfate;

R2 is OH or O-glucopyranose;

R3 is OCH3, OH, O-glucopyrariose, O-glucuronopyranose or glucopyranose;

R4 is OCH3 or OH; and

R5 is OCH3, OH, O-glucopyranose or O-glucose.

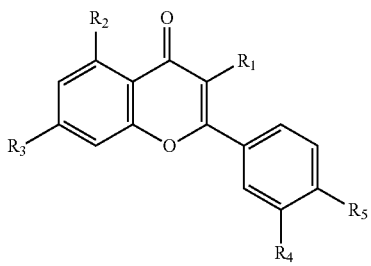

(I)

Among the quercetin analog/derivatives included in the current invention represented by general formula (I), well-known compounds are classified as follows: (i) a derivative group of the formula I wherein R2 to R5 are OH and R1 varies, includes quercetin where R1 is OH, avicularoside where R1 is O- -L-arabinofuranose, guiajaverin where R1 is O-arabinopyranose, hyperoside where R1 is O-β-D-galactopyranose, isohyperoside where R1 is O-β-D-galactopyranose, isoquercitrin where R1 is O-glucopyranose, multinoside A where Rx is O-[β-D-glucopyranosyl-(1-4)-α-L-rhamnopyranose], multinoside A acetate where Rx is (6-O-acetyl) -β-D-glucopyranosyl-(1-4)-α-L-rhamnopyranose, quercitrin where R1 is O- -L-rhamnopyranose, rutin where R1 is O-β-D-rutinose, quercetin-3-O-(2"-O-β-D-glucopyranosyl)-α-L-rhamnopyranoside where R1 is O-(2"-O-β-D-glucopyranosyl) -α-L-rhamnopyranose, quercetin-3-O-(6"-O-galloyl)-glucopyranoside where R1 is O-(6"-O-galloyl)-glucopyranose, quercetin-3-O-(6'''-O-β-coumaroyl-β-D-glucopyranosyl-(1-2)-α-L-rhamnopyranoside) where R1 is O-(6'''-O-β-coumaroyl-β-D-glucopyranosyl-(1-2) -α-L-rhamnopyranose, quercetin-3-O-D-glucopyranosyl-(1-6) -β-D-glucopyranosyl-(1-4) -α-L-rhamnopyranoside where Rx is O-D-glucopyranosyl-(1-6) -β-D-glucopyranosyl-(1-4) -α-L-rhamnopyranose, quercetin-3-O-[2"-O-6'''-O-β-(7 ''''-O-β-D-glucopyranosyl) coumaroyl-β-D-glucopyranosyl]-α-L-rhamnopyranoside where Rx is O-[2"-O-6'''-O-β-(7''''-O-β-D-glucopyranosyl) coumaroyl-β-D-glucopyranosyl]-α-L-rhamnopyranose, quercetin-3-O-[6'''-β-coumaroyl-β-D-glucopyranosyl-β-(1-4)-rhamnopyranoside] where R1 is O-[6'''-β-coumaroyl-β-D-glucopyranosyl-β-(1-4)-rhamnopyranose], quercetin-3-O-[α-L-rhamnopyranosyl (1-2) -α-L-rhamnopyranosyl-(1-6)-β-D-glucopyranoside] where Rx is O-[α-L-rhamnopyranosyl (1-2) -α-L-rhamnopyranosyl-(1-6) -β-D-glucopyranose], quercetin-3-O-[α-rhamnopyranosyl (1-4)-L-rhamnopyranosyl (1-6) β-D-galactopyranoside] where R1 is O-[α-rhamnopyranosyl (1-4) α-L-rhamnopyranosyl (1-6) β-D-galactopyranose], quercetin-3-O-[α-rhamnopyranosyl-(1-2)]-[β-glucopyranosyl-(1-6)]-β-D-galactopyranoside where R1 is O-[α-rhamnopyranosyl-(1-2)]-[β-glucopyranosyl-(1-6)]-β-D-galactopyranose, quercetin-3-O-[α-rhamnopyranosyl-(1-4) -α-rhamnopyranosyl- (1-6)-β-galactopyranoside] where Rx is O-[α-rhamnopyranosyl-(1-4) -α-rhamnopyranosyl-(1-6)-β-galactopyranose], quercetin-3-O-α-L-rhamnopyranosyl-(1-2)-β-D-galactopyranoside where R1 is O-α-L-rhamnopyranosyl-(1-2) -β-D-galactopyranose, quercetin-3-O-β-D-diglucopyranoside where R__ is O-β-D-diglucopyranose, quercetin-3-O-β-D-galactoside-2"-gallate where R1 is O-β-D-galactoside-2"-gallate, quercetin-3-O-β-D-glucopyranoside-(1-6) -β-D-galactopyranose, quercetin-3-O-β-D-glucopyranose-(1-6)-β-D-galactopyranose, quercetin-3-O-β-D-glucopyranosyl-(1-3) -α-L-rhamnopyranosyl-(1-6) -β-D-galactopyranoside where Rx is O-β-D-glucopyranosyl-(1-3) -α-L-rhamnopyranosyl-(1-6) -β-D-galactopyranose, quercetin-3-O-β-D-glucuronide where R1 is O-β-D-glucuronide, quercetin-3-O-β-D-xylopyranoside where R1 is O-β-D-χylopyranose, quercetin-3-O-diglucospyranoside where R1 is O-diglucospyranose, quercetin-3-O-gentiobioside where R1 is O-gentiobiose, quercetin-3-O-glucopyranos.ylgalactopyranoside where R1 is O-glucopyranosylgalactopyranose, quercetin-3-O-neohesperidoside where R1 is O-neohesperidose, quercetin-3-O-sophoroside where Rx is O-sophorose, quercetin-3-gentiotrioside where R1 is gentiotriose, quercetin-3-methyl ether where Rx is OCH3, quercetin-3-rhamnogentiobioside where R1 is rhamnogentiobiose, quercetin-3-rhamnoglucoside where Rx is rhamnoglucose, and quercetin-3-sulfate where Rx is sulfate; (ii) a derivative group of the formula I wherein Rx is —OH, three functional groups out of R2 to R5 are —OH, and the rest one functional group varies, includes isorhamnetin where R4 is OCH3, quercimeritrin where R3 is O-β-D-glucopyranose, rhamnetin where R3 is OCH3, quercetin-5-O-β-D-glucopyranoside where R2 is O-β-D-glucopyranose, quercetin-7-O-β-D-glucuronopyranoside where R3 is O-β-D-glucuronopyranose, and spireaoside where R5 is O-glucose; (iii) a derivative group of the formula I wherein three functional groups out of Rx to R5 are OH and the rest two functional groups vary, includes rhamnazin where R3 and R4 are OCH3 quercetin-3', 4'-di-methyl ether where R4 and R5 are OCH3 quercetin-3, 3'-dimethyl ether where Rx and R4 are OCH3, quercetin-3, 7-dimethyl ether where Rx and R3 are OCH3, quercetin-3-O-[2"-O-(6'''-O-β-coumaroyl) -β-D-glucopyranosyl]-α-L-rhamnopyranosyl-7-O-β-D-glucopyranoside where Rx is O-[2"-O-(6'''-O-β-coumaroyl) -β-D-glucopyranosyl]-α-L-rhamnopyranose and R3 is O-β-D-glucopyranose, quercetin-3-O-[2"-O-6'''-O-β-(7''''-O-β-D-glucopyranosyl) coumaroyl-β-D-glucopyranosyl]-α-L-rhamnopyranoside-7-O-β-D-glucopyranoside where Rx is O-[2"-O-6"-O-β-(7''''-O-β-D-glucopyranosyl) coumaroyl-β-D-glucopyranosyl]-α-L-rhamnopyranose and R3 is O-β-D-glucopyranose, quercetin-3-O-rutinoside-7-O-β-D-glucopyranoside where Rx is O-rutinose and R3 is O-β-D-glucopyranose, quercetin-3-O-α-L-arabinopyranosyl-7-O-β-D-glucopyranoside where R is O-α-L-arabinopyranosyl and R3 "O-β-D-glucopyranose, quercetin-7-O-β-D-glucopyranoside-3-O-sophoroside where R1 is O-sophorose and R3 is O-β-D-glucopyranose, quercetin-3-O-galactopyranosyl-7-O-diglucopyranoside where R is O-galactopyranose and R3 is O-glucopyranose, quercetin-3-O-glucopyranosyl-7-diglucopyranoside where Rx is O-glucopyranose and R3 is O-glucopyranose, quercetin-3, 7-diglucopyranoside where Rx is glucopyranose and R3 is glucopyranose, quercetin-3-gentiobiosyl-7-glucopyranoside where R is gentiobiose and R3 is glucopyranose, and quercetin-3, 4'-di-O-β-D-glucopyranoside where R and R5 are O-β-D-glucopyranose; and (iv) a derivative group of the formula I wherein more than three functional groups vary, includes quercetin-3, 4', 7-trimethyl ether where Rx, R3 and R5 are OCH3; and R2 and R4 are OH, and quercetin-3, 3', 4', 7-tetramethyl ether where Rx, R3, R4 and R5 are OCH3, and R2 is OH.

In one preferred embodiment, the invention further relates to a therapeutic agent for RIBE which comprises an active ingredient of quercetin, more specifically, to a therapeutic agent for RIBE comprising an active ingredient of a quercetin represented by the following formula (II) which effectively inhibits the activity of human cathepsin B (CTSB).

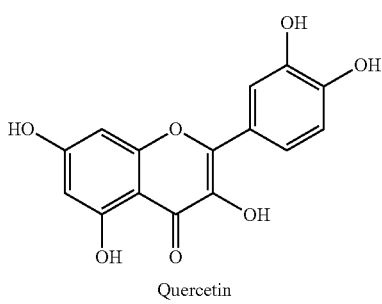

Quercetin

In another preferred embodiment, the invention further relates to a therapeutic agent for RIBE which comprises an active ingredient of isoquercetin, more specifically, to a therapeutic agent for RIBE comprising an active ingredient of a isoquercetin compound represented by the following formula (III) which effectively inhibits the activity of human cathepsin B (CTSB).

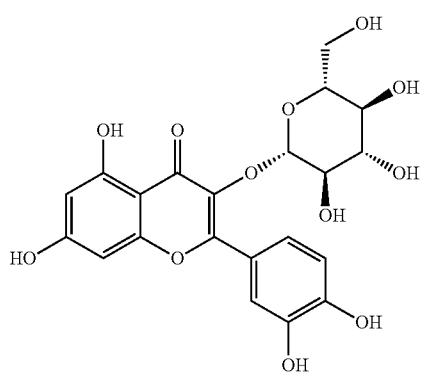

Isoquercitrin

Quercetin having same OH groups in Rx to R5 of the above general formula (I) is a phenolic compound found in over 4000 kinds of plants in nature and is known as one of the phytoestrogens. It has a molecular formula of CX5HXOO7 with resonance structures and a molecular weight of 302.33 g/mole and also known as vitamin P following the chemical structure identification in 1936. Quercetin is a rutin, a glycoside wherein sugar is linked via β-linkage and widely distributed in plants such as clover flower, pollen of common ragweed, and shell and stem of various plants, as well as in onion, kale, broccoli, lettuce, tomato, and apple. Quercetin has been verified not only to play an important role in maintenance of capillary wall integrity and capillary resistance (see: Gabor et al., Plant Flavonoids in Biology and Medicine II: Biochemical, Cellular, and Medical Properties, 280: 1-15, 1988; Havsteen et al., Biochemical Pharmacology, 32:1141-1148, 1983; all of which are hereby incorporated in their entirety by reference) but also to have antioxidation activity, vitamin P activity, ultraviolet absorbing activity, antihypertensive activity, antiarrhythmic activity, antiinflammatory activity, antiallergic activity, anticholesteremic activity, suppressive activity on liver toxicity, and therapeutic effect on infertility, thus, it may be expected to use quercetin widely in foods, medical and pharmaceutical products, and cosmetics. However, there has been no report on the use of quercetin for prevention and treatment of RIBE. The therapeutic agent for RIBE of the invention comprising an active ingredient of quercetin derivative is illustrated herein.

Figure 22:
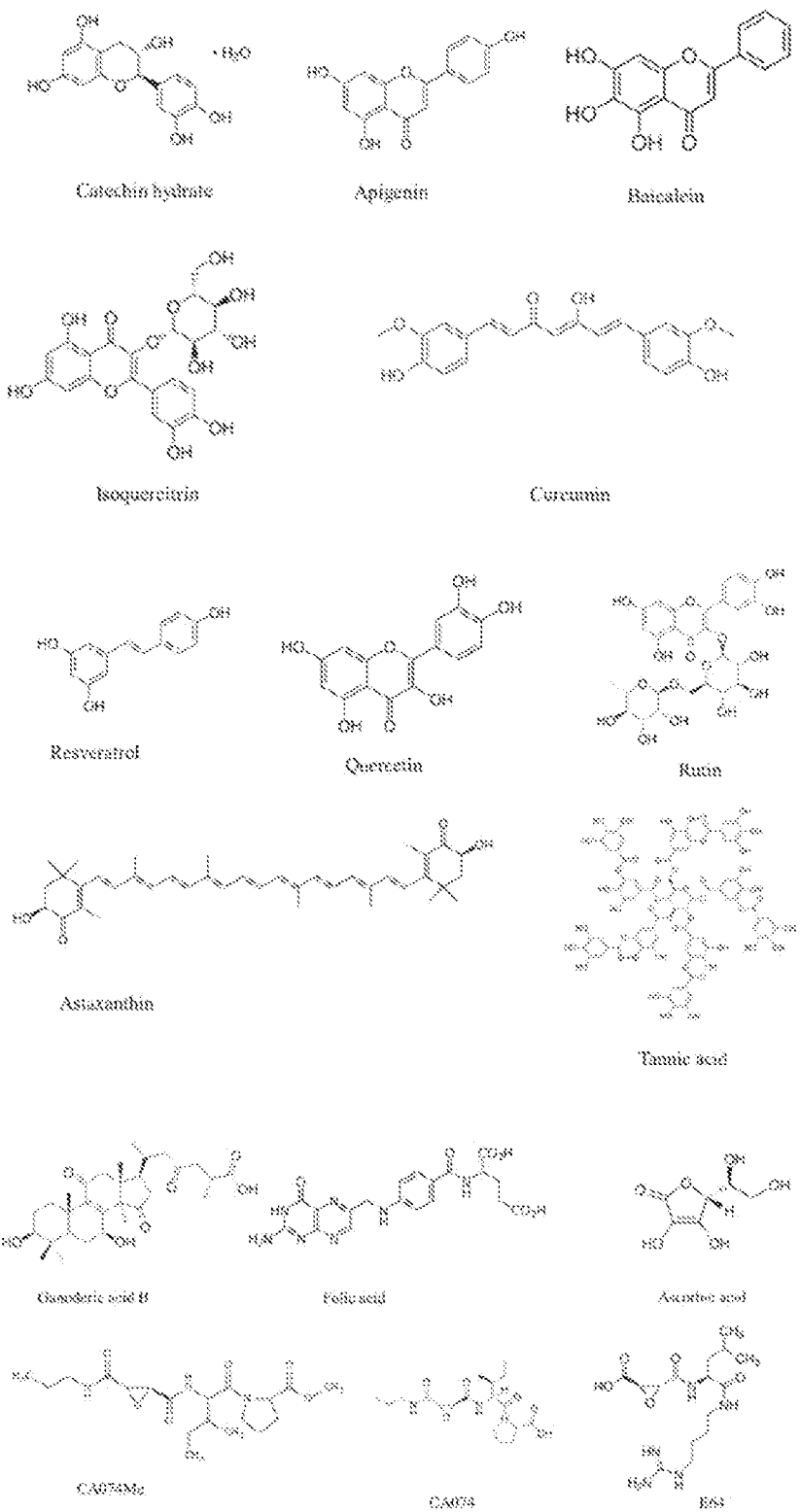
FIG. 22: Chemical Structure of screened compounds.
Figure 23:
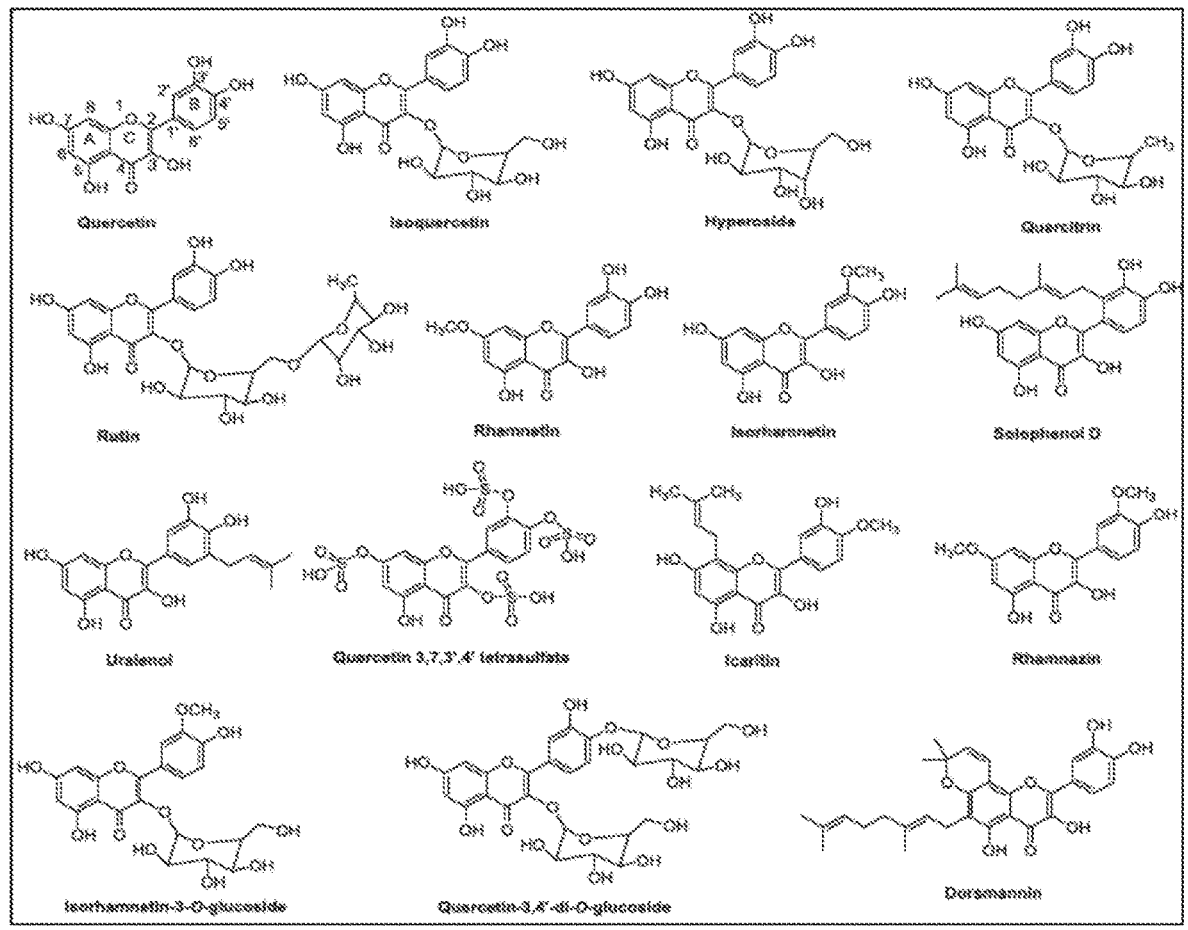
FIG. 23: Chemical Structure of quercetin and a plurality of quercetin analogs.

Additional compounds that may inhibit the activity of Cathepsin B, and/or inhibit or modulate RIBE in humans may include those identified in FIG. 22 or 23. For example, in another preferred embodiment, the invention further relates to a therapeutic agent for RIBE which comprises an active ingredient of E64, more specifically, to a therapeutic agent for RIBE comprising an active ingredient of a E64 compound represented by the following formula (IV) which may effectively inhibits the activity of human cathepsin B (CTSB).

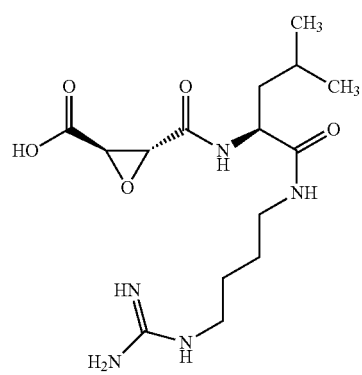

In another preferred embodiment, the invention further relates to a therapeutic agent for RIBE which comprises an active ingredient of CA074, more specifically, to a therapeutic agent for RIBE comprising an active ingredient of a CA074 compound represented by the following formula (V) which may effectively inhibits the activity of human cathepsin B (CTSB).

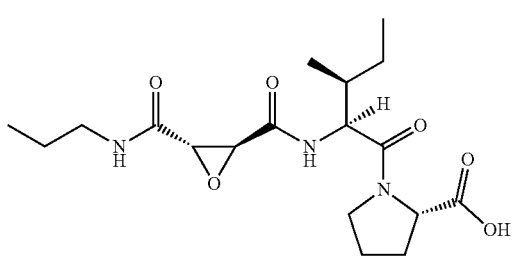

In another preferred embodiment, the invention further relates to a therapeutic agent for RIBE which comprises an active ingredient of CA074, more specifically, to a therapeutic agent for RIBE comprising an active ingredient of a CA074 compound represented by the following formula (VI) which may effectively inhibits the activity of human cathepsin B (CTSB).

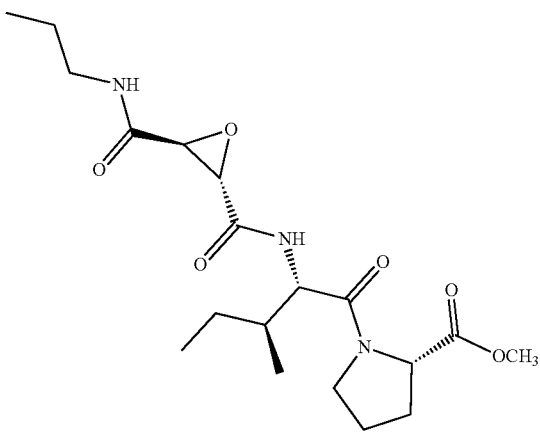

(VI)

As noted above, there has been no report on the use of any of the compounds or analogs of the compounds identified herein for prevention and treatment of RIBE. The therapeutic agent for RIBE of the invention comprising an active ingredient of quercetin derivative is illustrated herein. Analogs and/or derivative, the terms being generally interchangeable, are also included specifically in the inventive technology.

In order to evaluate the effects of quercetin and it analogs/derivatives on the activity of human cathepsin B (CTSB), the present inventors compared the effect of quercetin and its analog isoquercetin, and have found that both quercetin and isoquercetin inhibit the activity of CTSB, and as a result, inhibit and/or disrupt the propagation of RIBE in response to radiation exposure.

In a preferred embodiment, one or more quercetin, isoquercetin and/or other quercetin analogs/derivatives as described herein, as part of a therapeutic method and/or compositions for the treatment, prevention or amelioriation of RIBE, may be mixed with pharmaceutically acceptable excipients including binders such as polyvinylpyrrolidone, hydroxypropylcellulose, etc., disintegrating agents such as calcium carboxymethylcellulose, sodium glycolate starch, etc., diluting agents such as corn starch, lactose, soybean oil, crystalline cellulose, mannitol, etc., lubricating agents such as magnesium stearate, talc, etc., sweeteners such as sucrose, fructose, sorbitol, aspartame, etc., stabilizing agents such as sodium carboxymethylcellulose, α- or β-cyclodextrin, vitamin C, citric acid, white wax, etc, preservatives such as paraoxymethylbenzoate, paraoxypropylbenzoate, sodium benzoate, etc., and aromatics such as ethylvanillin, masking flavor, flavonomenthol, herb flavor, etc. to prepare pharmaceutical formulations for oral or parenteral administration such as tablets, capsules, soft capsules, liquids, ointments, pills, powders, suspensions, emulsions, syrups, suppositories or injections. For parenteral administration of the pharmaceutical preparation of the invention, subcutaneous, intravenous, intramuscular or intraperitoneal injection may be employed. For parenteral administration, quercetin derivative may be mixed with stabilizer or buffer in water to prepare solution or suspension which can be produced as single-dose formulations of ampule or vial.

In one embodiment, a therapeutically effective amount of quercetin, isoquercetin, or an analog thereof, as a therapeutic agent for the treatment of RIBE maybe be 2 to 20 mg/kg, preferably 8 to 12 mg/kg, which may be administered to the patient more than once a day depending on the patient's age, gender, degree of seriousness, way of administration, or purpose of prevention. However, alternative embodiments may include, between 0.01 to 1000 mg/kg, below 1 mg/kg or above 100 mg/kg. It should be noted that the term quercetin, as referred to herein, and specifically when discussed as a therapeutic agent/compound for the treatment of RIBE or RIBE-related symptoms/effects and the like, may mean quercetin, isoquercetin, an analog/derivative of quercetin or a mixture or combination of quercetin, isoquercetin, and/or analog/derivative of quercetin or other compounds identified herein.

A therapeutically effective amount of quercetin, isoquercetin, or an analog thereof, as a therapeutic agent for the treatment of RIBE to be included in the composition of the present invention can be determined using as a guide an enzyme-treated rutin intake of 0.1 to 20 g, preferably 0.3 to 10 g, per individual per day. The aforementioned amount can also be determined to give an intake of, for example, 0.002 to 400 mg/kg, more preferably 0.006 to 200 mg/kg, per kg body weight. Alternatively, the aforementioned amount can be determined to be in the range of 0.001 to 95% by weight, preferably 0.01 to 80% by weight, based on the total weight of the composition.

The terminology used herein is for describing embodiments and is not intended to be limiting. As used herein, the singular forms "a," "and" and "the" include plural referents, unless the content and context clearly dictate otherwise. Thus, for example, a reference to "a target molecule" may include a combination of two or more such target molecules. Unless defined otherwise, all scientific and technical terms are to be understood as having the same meaning as commonly used in the art to which they pertain.

As used herein, a biological marker ("biomarker" or "marker") is a characteristic that is objectively measured and evaluated as an indicator of normal biologic processes, pathogenic processes, or pharmacological responses to therapeutic interventions, consistent with NIH Biomarker Definitions Working Group (1998). Markers can also include patterns or ensembles of characteristics indicative of particular biological processes. The biomarker measurement can increase or decrease to indicate a particular biological event or process. In addition, if the biomarker measurement typically changes in the absence of a particular biological process, a constant measurement can indicate occurrence of that process.

The target molecules or markers of this invention may be used for diagnostic and prognostic purposes, as well as for therapeutic, drug screening and patient stratification purposes (e.g., to group patients into a number of "subsets" for evaluation), as well as other purposes described herein.

The present invention includes all compositions and methods relying on correlations between the reported markers and the radiosensitivity or radioresistance of cancer cells. Such methods include methods for determining whether a cancer patient or tumor is predicted to respond to administration of radiation therapy, as well as methods for assessing the efficacy of a radiation therapy. Additional methods may include determining whether a cancer patient or tumor is predicted to respond to administration of radiation therapy by exhibiting RIBE-mediated effects in the patient, as well as the level or severity of the RIBE-mediated effects as possibly correlated to the location, amount and type of irradiation. Such diagnostic information may be used to more effectively treat or kill, for example, cancerous cells while reducing or ameliorating RIBE to normal unexposed cells predicted to respond to administration of radiation therapy. This diagnostic activity may be done in vivo, or ex vivo.

Further included are methods for improving the efficacy of a radiation therapy by administering to a subject a therapeutically effective amount of an agent that alters the activity or expression of a biomarker, such as CTSB. In this context, the term "effective" is to be understood broadly to include reducing or alleviating the signs or symptoms of RIBE, improving the clinical course of RIBE, enhancing killing of cancerous cells, or reducing any other objective or subjective indicia of RIBE. Different drugs, doses and delivery routes can be evaluated by performing the method using different drug administration conditions. The markers may also be used as pharmaceutical compositions or in kits. The markers may also be used to screen candidate compounds that modulate their expression.

In one embodiment, the invention may include methods and systems for a novel diagnostic assay for RIBE utilizing one or more markers expression in response to irradiation. In this preferred embodiment, cells and/or tissue from a patient may be extracted, for example through a biopsy. These cells/tissue may be cancerous or non-cancerous in nature and may be taken from a plurality of different locations on the patient. These cells may be exposed to varying levels of radiation. The expression levels of one or more markers, such as CTSB, in response to irradiation may be measured and quantified. This measurement may demonstrate the cells and/or patients susceptible to RIBE and the threshold at which point RIBE-mediating markers/targets are expressed, begin to be expressed and the levels at which they are expressed. As demonstrated in FIG. 16, in this example, the levels of the CTSB expression in response to irradiation in treatment showed differential expression based on the level of radiation exposure, as well as cell type. In this embodiment, a diagnostic assay may be performed on the cells or tissue of a patient prior to, during and after radiotherapy to optimize radiotherapy treatments to achieve maximal cancer cell killing and minimize side effects, such as RIBE. For example, a patient or cancerous cell that exhibits a high threshold for RIBE markers/mediators may tolerate higher and longer exposure to radiotherapy, and vice versa. In this manner, radiotherapy procedures may be customized to accommodate the patient's sustainability to RIBE and/or other side-effects.

In certain embodiments of the inventive technology, target or market proteins, such as CPR-4 or CTSB, may encompass the "full protein," or one or more protein fragments. The methods of the present invention may be used to evaluate fragments of the listed molecules as well as molecules that contain an entire listed molecule, or at least a significant portion thereof (e.g., measured unique epitope), and modified versions of the proteins. Accordingly, such fragments, larger molecules and modified versions are included within the scope of the invention. For example, the target molecules CTSB; CPR-4; p53; CEP-1; DAF-2; other insulin-like growth factor receptors; PDK-1 kinase, other PDK kinases; and their associated signal transduction pathways may include a target protein, protein fragment, epitope, catalytic site, signaling site, localization site and the like.

The present invention includes all compositions and methods relying on correlations between the reported target molecules, such as CPR-4 and CTSB and the radiosensitivity (or radioresistance) of cancer cells. The present invention includes all compositions and methods relying on correlations between the reported target molecules, such as CPR-4 and CTSB and the radiosensitivity (or radioresistance) of cancer cells and the administration of quercetin or an analog thereof as a therapeutic agent for the treatment of RIBE. Such methods include methods for determining whether a cancer patient is predicted to respond to administration of radiation therapy, as well as methods for assessing the efficacy of a radiation therapy. Additional embodiment, include methods for determining whether a cancer patient is predicted to respond to administration of quercetin, and/or a quercetin analog, as well as methods for assessing the efficacy of the administration of quercetin, and/or a quercetin analog as therapy for RIBE. In one embodiment, expression of CTSB may be measured and/or characterized such that it may be a predictor of clinical outcome in patients prior to receiving radiotherapy, or patients that have severe RIBE possibly resulting in resistance to chemotherapy. Further included, are methods for improving the efficacy of a radiation therapy by administering to a subject a therapeutically effective amount of quercetin, isoquercetin and/or a quercetin analog that inhibits the activity or expression of one or more target molecules, such as CTSB.

Further included, are methods for improving the efficacy of a radiation therapy by administering to a subject a therapeutically effective amount of an agent that alters the activity or expression of one or more target molecules, such as CPR-4, Cathepsin B (CTSB), CEP-1, p53, DAF-2, insulin/IGF receptor (INSR), PDK-1 and/or PDK1 kinase. In this context, the term. In this context, the term "effective" or "therapeutically effective" is to be understood broadly to include reducing or alleviating the signs or symptoms of RIBE, improving the clinical course of RIBE, or reducing any other objective or subjective indicia of the RIBE. It also includes reducing or alleviating the signs or symptoms of cancer, improving the clinical course of the disease, or reducing any other objective or subjective indicia of the disease, decreasing cancer cell resistance to chemotherapy, increasing tolerance of normal non-targeted cells for chemotherapy or radiotherapy treatments, or increasing the effectiveness of chemotherapy and/or radiotherapy. Different drugs, doses and delivery routes can be evaluated by performing the method using different drug administration conditions. The molecular targets may also be used as pharmaceutical compositions or in kits. The targets may also be used to screen candidate compounds that modulate their expression.

Additional embodiments of the invention include methods for improving the efficacy of chemotherapy by administering to a subject a therapeutically effective amount of an agent that alters the activity or expression of one or more target molecules, such as CPR-4, Cathepsin B (CTSB), CEP-1, p53, DAF-2, insulin/IGF receptor (INSR), PDK-1 and/or PDK1 kinase. In this context, the term "effective" is to be understood broadly to include reducing a patient's resistance to chemotherapeutic agents, reducing or alleviating the signs or symptoms of cancer, improving the clinical course of the disease, or reducing any other objective or subjective indicia of the disease. Different drugs, doses and delivery routes can be evaluated by performing the method using different drug administration conditions. The molecular targets may also be used as pharmaceutical compositions or in kits. The targets may also be used to screen candidate compounds that modulate their expression.

As used in this application the terms alter, or altering the expression or activity of one or more targets may include reduction in the expression or biological activity of a target, such as CTSB or CPR-4. In additional embodiments, the term alters, or altering the expression or activity of one or more targets may include increase in the expression or biological activity of a target, such as CTSB or CPR-4 or other components in the signal pathways. In these embodiments, activity or biological activity may include altering the enzymatic activity of a target protein or mRNA, for example. Additional embodiments may include altering the shape or conformation of a target protein such that its activity is reduced or increased. In yet further embodiments, the terms alter, or altering the expression or activity of one or more targets may include reduction or increases in up- or down-stream targets or other receptors or molecules involved in a signal pathway. In this embodiment, altering the expression or activity of a target may amplify and/or suppress one or more corresponding signal pathways and their constituent components. In additional embodiments, the terms alter, or altering the expression or activity of one or more targets may include increasing or decreasing binding affinities with other molecules or receptors, as well as changes in the targets ability to be secreted or its movement within a cell, tissue, organ or organism. Such altering of secretion may also be accomplished through selective or general blocking of secretion-dependent molecules and/or signal pathways and/or cell-/membrane-transporters.

It is expected that the target molecules described herein will be measured and/or used in combination with other signs, symptoms and clinical tests of cancer, such as skin examination, dermoscopy, lymph node examination, chest x-ray, CT scan of the chest, head, abdomen, or pelvis, magnetic resonance imaging (MRI), and/or serum lactate dehydrogenase blood tests. Measurement and/or use of the target molecules of the invention along with any other targets known in the art, including those not specifically listed herein, falls within the scope of the present invention.

As used herein, the phrase "gene expression" or "protein expression," such as the level of "ctsb gene expression," or "the level of CTSB protein expression," includes any information pertaining to the amount of gene transcript or protein present in a sample, in a cell, in a patient, secreted in a sample, and secreted from a cell as well as information about the rate at which genes or proteins are produced or are accumulating or being degraded (e.g., reporter gene data, data from nuclear runoff experiments, pulse-chase data etc.). Certain kinds of data might be viewed as relating to both gene and protein expression. For example, protein levels in a cell are reflective of the level of protein as well as the level of transcription, and such data is intended to be included by the phrase "gene or protein expression information." Such information may be given in the form of amounts per cell, amounts relative to a control gene or protein, in unitless measures, etc.; the term "information" is not to be limited to any particular means of representation and is intended to mean any representation that provides relevant information. The term "expression levels" refers to a quantity reflected in or derivable from the gene or protein expression data, whether the data is directed to gene transcript accumulation or protein accumulation or protein synthesis rates, etc.

As used herein, a compound is referred to as "isolated" when it has been separated from at least one component with which it is naturally associated. For example, a metabolite can be considered isolated if it is separated from contaminants including polypeptides, polynucleotides and other metabolites. Isolated molecules can be either prepared synthetically or purified from their natural environment. Standard quantification methodologies known in the art can be employed to obtain and isolate the molecules of the invention.

Homologs and alleles of the target molecules or proteins of the invention can be identified by conventional techniques. As used herein, a homolog to a polypeptide is a polypeptide from a human or other animal that has a high degree of structural similarity to the identified polypeptides. Identification of human and other organism homologs of polypeptide targets identified herein will be familiar to those of skill in the art.

Polypeptides encoded by the target molecule genes identified herein may reflect a single polypeptide or complex or polypeptides. Accordingly, in another embodiment, the invention provides a polypeptide that is a fragment, precursor, successor or modified version of a protein target molecule described herein. In another embodiment, the invention includes a protein target molecule that comprises a foregoing fragment, precursor, successor or modified polypeptide. As used herein, a "fragment" of a polypeptide refers to a single amino acid or a plurality of amino acid residues comprising an amino acid sequence that has at least 5 contiguous amino acid residues, at least 10 contiguous amino acid residues, at least 20 contiguous amino acid residues or at least 30 contiguous amino acid residues of a sequence of the polypeptide. As used herein, a "fragment" of poly- or oligonucleotide refers to a single nucleic acid or to a polymer of nucleic acid residues comprising a nucleic acid sequence that has at least 15 contiguous nucleic acid residues, at least 30 contiguous nucleic acid residues, at least 60 contiguous nucleic acid residues, or at least 90% of a sequence of the polynucleotide. In some embodiment, the fragment is an antigenic fragment, and the size of the fragment will depend upon factors such as whether the epitope recognized by an antibody is a linear epitope or a conformational epitope. Thus, some antigenic fragments will consist of longer segments while others will consist of shorter segments, (e.g. 5, 6, 7, 8, 9, 10, 11 or 12 or more amino acids long, including each integer up to the full length of the polypeptide). Those skilled in the art are well versed in methods for selecting antigenic fragments of proteins.

In some embodiments, a target molecule, such as CPR-4, Cathepsin B, CEP-1, p53, DAF-2, insulin/IGF receptors, PDK-1 and PDK1 kinase, is a member of one or more biological pathways. As used herein, the term "precursor" or "successor" refers to molecules that precede or follow the target polypeptide or polynucleotide in the biological pathway. Thus, once a polypeptide target or polynucleotide target is identified as a member of one or more biological pathways, the present invention can include additional precursor or successor members of the biological pathway. Such identification of biological pathways and their members is within the skill of one in the art.

Additionally, the present invention includes polypeptides that have substantially similar sequence identity to the target polypeptide molecules of the present invention. As used herein, two polypeptides have "substantial sequence identity" when there is at least about 70% sequence identity, at least about 80% sequence identity, at least about 90% sequence identity, at least about 95% sequence identity, at least about 99% sequence identity, and preferably 100% sequence identity between their amino acid sequences, or when polynucleotides encoding the polypeptides are capable of forming a stable duplex with each other under stringent hybridization conditions. For example, conservative amino acid substitutions may be made in polypeptides to provide functionally equivalent variants of the foregoing target polypeptides, i.e., the variants may or may not retain the functional capabilities of the polypeptides. As used herein, a "conservative amino acid substitution" refers to an amino acid substitution that does not alter the relative charge or size characteristics of the protein in which the amino acid substitution is made. Variants can be prepared according to methods for altering polypeptide sequence known to one of ordinary skill in the art such as are found in references that compile such methods.

As used herein, the term "gene" or "polynucleotide" refers to a single nucleotide or a polymer of nucleic acid residues of any length. The polynucleotide may contain deoxyribonucleotides, ribonucleotides, and/or their analogs and may be double-stranded or single stranded. A polynucleotide can comprise modified nucleic acids (e.g., methylated), nucleic acid analogs or non-naturally occurring nucleic acids and can be interrupted by non-nucleic acid residues. For example, a polynucleotide includes a gene, a gene fragment, cDNA, isolated DNA, mRNA, tRNA, rRNA, isolated RNA of any sequence, recombinant polynucleotides, primers, probes, plasmids, and vectors. Included within the definition are nucleic acid polymers that have been modified, whether naturally or by intervention.

In another embodiment, the invention provides polynucleotides that have substantial sequence similarity to a target polynucleotide molecule that is described herein. Two polynucleotides have "substantial sequence identity" when there is at least about 70% sequence identity, at least about 80% sequence identity, at least about 90% sequence identity, at least about 95% sequence identity or at least 99% sequence identity between their amino acid sequences or when the polynucleotides are capable of forming a stable duplex with each other under stringent hybridization conditions. Such conditions are well known in the art. As described above with respect to polypeptides, the invention includes polynucleotides that are allelic variants, the result of SNPs, or that in alternative codons to those present in the native materials as inherent in the degeneracy of the genetic code.

In some embodiments of the invention, the methods comprise detecting in a sample from a patient, a level of gene expression of one or more target molecules, wherein the expression levels of the target are indicative of whether the patient will respond to the administration of radiation therapy and/or be more or less resistant to RIBE processes. In another embodiment, the methods comprise detecting in a sample from a patient, a level of protein activity, such as CTSB activity, wherein the activity levels of the target is indicative of whether the patient will respond to the administration of radiation therapy and/or be more or less resistant to RIBE processes. In another embodiment, the methods comprise detecting in a sample from a patient, a gene sequence, such as the CTSB gene, wherein the sequence of the target gene is indicative of whether the patient will respond to the administration of radiation therapy and/or be more or less resistant to RIBE processes.

For example, in one embodiment, CTSB protein may include SEQ ID NO. 1:

```
MWQLWASLCCLLVLANARSRPSFHPLSDELVNYVNKRNTTWQAGHNFY

NVDMSYLKRLCGTFLGGPKPPQRVMFTEDLKLPASFDAREQWPQCPTI

KEIRDQGSCGSCWAFGAVEAISDRICIHTNAHVSVEVSAEDLLTCCGS

MCGDGCNGGYPAEAWNFWTRKGLVSGGLYESHVGCRPYSIPPCEHHVN

GSRPPCTGEGDTPKCSKICEPGYSPTYKQDKHYGYNSYSVSNSEKDIM

AEIYKNGPVEGAFSVYSDFLLYKSGVYQHVTGEMMGGHAIRILGWGVE

NGTPYWLVANSWNTDWGDNGFFKILRGQDHCGIESEVVAGIPRTDQYW

EKI
```

SEQ ID NO. 1, also include all homologs of the same, which include nucleic acid sequences that may generate this protein sequence and those with at least 80% homology thereof.

As used herein, the term "sample" includes a sample from any bodily fluid or tissue (e.g., serum, plasma, blood, cerebrospinal fluid, urine, saliva, cancer tissue, healthy tissue). As used herein, the terms "patient," "subject" includes "a subject or patient who has cancer" and "a cancer patient or subject" "a radiosensitive patient" "a patient in need of radio therapy" "person exposed to radiation" and "a person that may be exposed to radiation" are intended to refer to subjects who have been diagnosed with cancer, have received radiotherapy, are currently receiving radiotherapy, may receive radiotherapy in the future, or have been or may in the future be exposed to some level of radiation. A "subject" is any organism of interest, generally a mammalian subject, such as a mouse, nematode and preferably a human subject.

The target molecules and therapeutic compositions of the invention are useful for predicting RIBE processes resulting from radiation exposure and/or radiotherapy. The target molecules and therapeutic compositions of the invention are also useful for determining if radiotherapy may be an effective treatment for cancer or other disease condition. The target molecules and therapeutic compositions of the invention are useful for predicting the outcome of radiation in multiple cancer types, including without limitation, bladder cancer, lung cancer, head and neck cancer, glioma, gliosarcoma, anaplastic astrocytoma, medulloblastoma, lung cancer, small cell lung carcinoma, cervical carcinoma, colon cancer, rectal cancer, chordoma, throat cancer, Kaposi's sarcoma, lymphangiosarcoma, lymphangioendotheliosarcoma, colorectal cancer, endometrium cancer, ovarian cancer, breast cancer, pancreatic cancer, prostate cancer, renal cell carcinoma, hepatic carcinoma, bile duct carcinoma, choriocarcinoma, seminoma, testicular tumor, Wilms' tumor, Ewing's tumor, bladder carcinoma, angiosarcoma, endotheliosarcoma, adenocarcinoma, sweat gland carcinoma, sebaceous gland sarcoma, papillary sarcoma, papillary adenosarcoma, cystadenosarcoma, bronchogenic carcinoma, medullary carcinoma, mastocytoma, mesotheliorma, synovioma, melanoma, leiomyosarcoma, rhabdomyosarcoma, neuroblastoma, retinoblastoma, oligodentroglioma, acoustic neuroma, hemangioblastoma, memngioma, pinealoma, ependymoma, craniopharyngioma, epithelial carcinoma, embryonal carcinoma, squamous cell carcinoma, base cell carcinoma, fibrosarcoma, myxoma, myxosarcoma, liposarcoma, chondrosarcoma, osteogenic sarcoma, and leukemia.

The present invention also encompasses reagents, compounds, agents or molecules which specifically bind the target molecules, such as CTSB, whether they be polypeptides or polynucleotides. As used herein, the term "specifically binding," refers to the interaction between binding pairs (e.g., an antibody and an antigen or aptamer and its target). In some embodiments, the interaction has an affinity constant of at most 10-6 moles/liter, at most 10-7 moles/liter, or at most 10-8 moles/liter. In other embodiments, the phrase "specifically binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen binding fragment thereof in the absence of the antigen is considered to be background. Binding can be measured using a variety of methods standard in the art including enzyme immunoassays (e.g., ELISA), immunoblot assays, etc.).

The molecules that may bind to one or more of the inventions targets include antibodies, aptamers and antibody derivatives or fragments. As used herein, the term "antibody" refers to an immunoglobulin molecule capable of binding an epitope present on an antigen. The term is intended to encompass not only intact immunoglobulin molecules such as monoclonal and polyclonal antibodies, but also bi-specific antibodies, humanized antibodies, chimeric antibodies, anti-idiopathic (anti-ID) antibodies, single-chain antibodies, Fab fragments, F(ab') fragments, fusion proteins and any modifications of the foregoing that comprise an antigen recognition site of the required specificity.

As used herein, an aptamer is a non-naturally occurring nucleic acid molecule or peptide having a desirable action on a target, including, but not limited to, binding of the target, catalytically changing the target, reacting with the target in a way which modifies/alters the target or the functional activity of the target, covalently attaching to the target as in a suicide inhibitor, facilitating the reaction between the target and another molecule. In one embodiment, the antibodies, antibody derivatives or fragments, or aptamers specifically bind to a component that is a fragment, modification, precursor or successor of one or more target molecules.

Another aspect of the invention provides compositions comprising the target molecules, a binding molecule that is specific for the target (e.g., an antibody or an aptamer), an inhibitor of the target, or other molecule that can increase or decrease the level or activity of the target molecule, such CTSB, through the administration of quercetin, isoquercetin, or an analog thereof. Such compositions may be pharmaceutical compositions formulated for use as a therapeutic. Alternatively, the invention provides a composition that comprises a component that is a fragment, modification, precursor, or successor of a target molecule that comprises a foregoing component. In another embodiment, the invention provides a composition that comprises an antibody or aptamer that specifically binds to a target polypeptide or a molecule that comprises a foregoing antibody or aptamer. In some embodiments, the level of the target molecules may be determined using a standard immunoassay, such as sandwiched ELISA using matched antibody pairs and chemiluminescent detection.

In an alternative embodiment of the invention, a method is provided for assessing the efficacy or effectiveness of a radiation treatment being administered to a patient, preferably a cancer patient. The method is performed by obtaining a first sample, such as serum or tissue, from the subject at a certain time (to); measuring the level of at least one of the target molecules or precursors or successors in the biological sample; and comparing the measured level with the level measured with respect to a sample obtained from the subject at a later time (t1). Depending upon the difference between the measured levels, it can be seen whether the target level has increased, decreased, or remained constant over the interval (trto). Subsequent sample acquisitions and measurements can be performed as many times as desired over a range of times t2 to tn. If a target molecule maintains a consistent level or level of activity, or only raises to within a pre-determined threshold that has been shown to be indicative of RIBE, it would indicate that the radiation therapy has not resulted in RIBE or significant RIBE processes and the amount and/or duration of radiation exposure may be increased or modified. On the other hand, an increase in the target molecule level, such as CTSB, above a pre-determined threshold that has been shown to be indicative of RIBE, it would indicate that the radiation therapy has or will resulted in RIBE or significant RIBE processes and the amount and/or duration of radiation exposure may be decreased or modified.

In another aspect, the invention provides methods for improving the response of a cancer patient to radiation therapy, preventing RIBE or alleviating RIBE after radiation therapy or radiation exposure. The methods comprise administering a therapeutically effective amount of at least one agent, such as quercetin, isoquercetin, or an analog thereof and/or E64, CA074, or CA074Me and their analogs, that inhibits the activity of CTSB and any homolog or variant of the same. In some embodiments, the agent may be administered prophylactically, prior to the administration of the radiation therapy i.e. prior to administering or commencing the radiation therapy. In some embodiments, the agent may be administered simultaneously with or at the same time as the administration of the radiotherapy or after radiotherapy at the onset of detectable RIBE.

As used herein, the term "agent" means a chemical or biological molecule such as a simple or complex organic molecule, a peptide, a polypeptide or protein, or a nucleic acid molecule that can inhibit the expression or activity of a target molecule, such as CPR-4, Cathepsin B (CTSB), CEP-1, p53, DAF-2, insulin/IGF receptors, PDK-1, and PDK1 kinase and any homolog or variant proteins and any homolog or variant proteins. Such molecules may be purchased commercially or synthesized using methods known in the art. Suitable organic molecules to be used as agents may include drugs, synthetic or naturally occurring, that are capable of inhibiting the activity of the target molecule. The term "agent" may also mean the compound(s) quercetin, isoquercetin, or an analog/derivative thereof.

In some embodiments, the agent may be a polypeptide or protein. In one aspect, the protein is an antibody specifically reactive with a target protein or polypeptide, such as CPR-4, Cathepsin B (CTSB), CEP-1, p53, DAF-2, insulin/IGF receptors, PDK-1, and PDK1 kinase and any homolog or variant proteins, that is effective for decreasing a biological activity of the target protein or polypeptide. For example, by using immunogens derived from a target protein or polypeptide, e.g., based on the cDNA sequences, anti-protein/anti-peptide antisera or monoclonal antibodies can be made by standard protocols.

A mammal, such as a mouse, a hamster or rabbit can be immunized with an immunogenic form of the target (e.g., CPR-4, Cathepsin B (CTSB), CEP-1, p53, DAF-2, insulin/IGF receptors, PDK-1, and PDK1 kinase and any homolog or variant proteins protein or polypeptide or an antigenic fragment which is capable of eliciting an antibody response, or a fusion protein). Techniques for conferring immunogenicity on a protein or peptide include conjugation to carriers or other techniques well known in the art. An immunogenic portion of a target protein or polypeptide, such as CPR-4, can be administered in the presence of adjuvant. The progress of immunization can be monitored by detection of antibody titers in plasma or serum. Standard ELISA or other immunoassays can be used with the immunogen as antigen to assess the levels of antibodies.

In a preferred embodiment, the subject antibodies are immunospecific for antigenic determinants of a target protein or polypeptide, such as Cathepsin B (CTSB), of a mammal. In one example, following immunization of an animal with an antigenic preparation of CPR-4 or CTSB protein or polypeptide, anti-CPR-4 or anti-CTSB antisera can be obtained and, if desired, polyclonal anti-CPR-4 or anti-CTSB antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Again, such techniques are well known in the art. Hybridoma cells can be screened immunochemically for production of antibodies specifically reactive with a mammalian CPR-4 or CTSB protein or polypeptide and monoclonal antibodies isolated from a culture comprising such hybridoma cells.

In certain preferred embodiments, an antibody of the invention is a monoclonal antibody, and in certain embodiments the invention makes available methods for generating novel antibodies. For example, a method for generating a monoclonal antibody that binds specifically to a CPR-4, or CTSB protein or polypeptide may comprise administering to a mouse an amount of an immunogenic composition comprising the CPR-4, or CTSB protein or polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the CPR-4 or CTSB protein or polypeptide. Once obtained, a hybridoma can be propagated in a cell culture, optionally in culture conditions where the hybridoma-derived cells produce the monoclonal antibody that binds specifically to the CPR-4, or CTSB protein or polypeptide. The monoclonal antibody may be purified from the cell culture. One characteristic that influences the specificity of an antibody:antigen interaction is the affinity of the antibody for the antigen. Although the desired specificity may be reached with a range of different affinities, generally preferred antibodies will have an affinity (a dissociation constant) of about 10-6, 10-7, 10-8, 10-9 or less.

In some embodiments, the agent may be a nucleic acid molecule. In certain aspects, the nucleic acid molecule may be RNAi, ribozyme, antisense, DNA enzyme or other nucleic acid-related compositions for manipulating (typically decreasing) a targets expression or activity. This may include altered expression of targets such as CPR-4, CTSB or any other target molecule singly or in combination. (It should be noted, that while preferred embodiments may use CPR-4 or CTSB as an exemplary model, this is not way limiting on the many target molecules that comprise the current invention.) Some embodiments of the invention make use of materials and methods for effecting knockdown of target genes, such as CPR-4 and/or CTSB genes, by means of RNA interference (RNAi). RNAi is a process of sequence-specific post-transcriptional gene repression which can occur in eukaryotic cells. In general, this process involves degradation of an mRNA of a particular sequence induced by double-stranded RNA (dsRNA) that is homologous to that sequence. Any selected gene may be repressed by introducing a dsRNA which corresponds to all or a substantial part of the mRNA for that gene. It appears that when a long dsRNA is expressed, it is initially processed by a ribonuclease III into shorter dsRNA oligonucleotides of as few as 21 to 22 base pairs in length.

Accordingly, RNAi may be effected by introduction or expression of relatively short homologous dsRNAs. The double stranded oligonucleotides used to effect RNAi are preferably less than 30 base pairs in length and, more preferably, comprise about 25, 24, 23, 22, 21, 20, 19, 18 or 17 base pairs of ribonucleic acid. Optionally the dsRNA oligonucleotides of the invention may include 3' overhang ends. Exemplary 2-nucleotide 3' overhangs may be composed of ribonucleotide residues of any type and may even be composed of 2'-deoxythymidine resides, which lowers the cost of RNA synthesis and may enhance nuclease resistance of siRNAs in the cell culture medium and within transfected cells (see Elbashi et al. (2001) Nature 411: 494-8).

Longer dsRNAs of 50, 75, 100 or even 500 base pairs or more may also be utilized in certain embodiments of the invention. Exemplary concentrations of dsRNAs for effecting RNAi are about 0.05 nM, 0.1 nM, 0.5 nM, 1.0 nM, 1.5 nM, 25 nM or 100 nM, although other concentrations may be utilized depending upon the nature of the cells treated, the patient, the level of radiation exposure by the patient, the gene target and other factors readily discernable the skilled artisan. Exemplary dsRNAs may be synthesized chemically or produced in vitro or in vivo using appropriate expression vectors. Exemplary synthetic RNAs include 21 nucleotide RNAs chemically synthesized using methods known in the art (e.g. Expedite RNA phophoramidites and thymidine phosphoramidite (Proligo, Germany).

Synthetic oligonucleotides are preferably deprotected and gel-purified using methods known in the art (see e.g. Elbashir et al. (2001) Genes Dev. 15: 188-200). Longer RNAs may be transcribed from promoters, such as T7 RNA polymerase promoters, known in the art. A single RNA target, placed in both possible orientations downstream of an in vitro promoter, will transcribe both strands of the target to create a dsRNA oligonucleotide of the desired target sequence. Any of the above RNA species will be designed to include a portion of nucleic acid sequence represented in a target gene, such as, for example, a nucleic acid that hybridizes, under stringent and/or physiological conditions, to a CPR-4 mRNA, or a CTSB mRNA and a complement thereof in certain embodiments.

The specific sequence utilized in design of the oligonucleotides may be any contiguous sequence of nucleotides contained within the expressed gene message of the target. Programs and algorithms, known in the art, may be used to select appropriate target sequences. In addition, optimal sequences may be selected utilizing programs designed to predict the secondary structure of a specified single stranded nucleic acid sequence and allowing selection of those sequences likely to occur in exposed single stranded regions of a folded mRNA. Methods and compositions for designing appropriate oligonucleotides may be found, for example, in U.S. Pat. No. 6,251,588, the contents of which are incorporated herein by reference.

Messenger RNA (mRNA) is generally thought of as a linear molecule which contains the information for directing protein synthesis within the sequence of ribonucleotides, however studies have revealed a number of secondary and tertiary structures that exist in most mRNAs. Secondary structure elements in RNA are formed largely by Watson-Crick type interactions between different regions of the same RNA molecule. Important secondary structural elements include intramolecular double stranded regions, hairpin loops, bulges in duplex RNA and internal loops. Tertiary structural elements are formed when secondary structural elements come in contact with each other or with single stranded regions to produce a more complex three-dimensional structure. A number of researchers have measured the binding energies of a large number of RNA duplex structures and have derived a set of rules which can be used to predict the secondary structure of RNA (see e.g Jaeger et al. (1989) Proc. Natl. Acad. Sci. USA 86:7706 (1989); and Turner et al. (1988) Annu. Rev. Biophys. Biophys. Chern. 17:167). The rules are useful in identification of RNA structural elements and, in particular, for identifying single stranded RNA regions which may represent preferred segments of the mRNA to target for silencing RNAi, ribozyme or antisense technologies. Accordingly, preferred segments of the mRNA target can be identified for design of the RNAi mediating dsRNA oligonucleotides as well as for design of appropriate ribozyme and hammerhead ribozyme compositions related to the targets of the invention.

The dsRNA oligonucleotides may be introduced into the cell by transfection with an heterologous target gene using carrier compositions such as liposomes, which are known in the art as described by the manufacturer for adherent cell lines. Transfection of dsRNA oligonucleotides for targeting endogenous genes may be carried out using Oligofectamine. Transfection efficiency may be checked using fluorescence microscopy for mammalian cell lines after co-transfection of hGFP-encoding pAD3 (Kehlenback et al. (1998) J Cell Biol 141: 863-74). The effectiveness of the RNAi may be assessed by any of a number of assays following introduction of the dsRNAs. These include Western blot analysis using antibodies which recognize the CPR-4 or CTSB gene product following sufficient time for turnover of the endogenous pool after new protein synthesis is repressed, reverse transcriptase polymerase chain reaction and Northern blot analysis to determine the level of existing target mRNA, such as CPR-4 or CTSB. Further compositions, methods and applications of RNAi technology are provided in U.S. Pat. Nos. 6,278,039, 5,723,750 and 5,244,805, which are incorporated herein by reference.

Ribozyme molecules designed to catalytically cleave, for example CPR-4 or CTSB mRNA transcripts can also be used to prevent translation of subject mRNAs and/or expression of CPR-4 or CTSB in multiple animal systems (see, e.g., PCT International Publication W090111364, published Oct. 4, 1990; Sarver et al. (1990) Science 247:1222-1225 and U.S. Pat. No. 5,093,246). Ribozymes are enzymatic RNA molecules capable of catalyzing the specific cleavage of RNA. (For a review, see Rossi (1994) Current Biology 4: 469-471). The mechanism of ribozyme action involves sequence specific hybridization of the ribozyme molecule to complementary target RNA, followed by an endonucleolytic cleavage event. The composition of ribozyme molecules preferably includes one or more sequences complementary to a CPR-4 or CTSB mRNA, and the well-known catalytic sequence responsible for mRNA cleavage or a functionally equivalent sequence (see, e.g., U.S. Pat. No. 5,093,246, which is incorporated herein by reference in its entirety).

In addition to ribozymes that cleave mRNA at site specific recognition sequences, hammerhead ribozymes can also be used to destroy target mRNAs. Hammerhead ribozymes cleave mRNAs at locations dictated by flanking regions that form complementary base pairs with the target mRNA. Preferably, the target mRNA has the following sequence of two bases: 5'-mUG-3'. The construction and production of hammerhead ribozymes is well known in the art and is described more fully in Haseloff and Gerlach ((1988) Nature 334:585-591; and see PCT Appln. No. W089/05852, the contents of which are incorporated herein by reference). Hammerhead ribozyme sequences can be embedded in a stable RNA such as a transfer RNm (tRNA) to increase cleavage efficiency in vivo (Perriman et al. (1995) Proc. Natl. Acad. Sci.mUSA, 92: 6175-79; de Feyter, and Gaudron, Methods in Molecular Biology, Vol. 74, Chapter 43, "Expressing Ribozymes in Plants", Edited by Turner, P. C, Humana Press Inc., Totowa, N.J.). In particular, RNA polymerase HI-mediated expression of tRNA fusion ribozymes are well known in the art (see Kawasaki et al. (1998) Nature 393: 284-9; Kuwabara et al. (1998) Nature Biotechnol. 16: 961-5; and Kuwabara et al. (1998) Mol. Cell 2: 617 27; Koseki et al. (1999) J Virol 73: 1868-77; Kuwabara et al. (1999) Proc Natl Acad Sci USA 96:m1886-91; Tanabe et al. (2000) Nature 406: 473-4). There are typically a number of potential hammerhead ribozyme cleavage sites within a given target cDNA sequence. Preferably the ribozyme is engineered so that the cleavage recognition site is located near the 5' end of the target mRNA—to increase efficiency and minimize the intracellular accumulation of non-functional mRNA transcripts. Furthermore, the use of any cleavage recognition site located in the target sequence encoding different portions of the C-terminal amino acid domains of, for example, long and short forms om target would allow the selective targeting of one or the other form of the target, and thus, have a selective effect on one form of the target gene product. Gene targeting ribozymes necessarily contain a hybridizing region complementary to two regions, each of at least 5 and preferably each 6, 7, 8, 9, 10, 11, 12, 13, 14, 15, 16, 17, 18, 19 or 20 contiguous nucleotides in length of a CPR-4 or CTSB mRNA. In addition, ribozymes possess highly specific endoribonuclease activity, which autocatalytically cleaves the target sense mRNA.

The present invention extends to ribozymes which hybridize to a sense mRNA encoding a CPR-4 or CTSB gene thereby hybridizing to the sense mRNA and cleaving it, such that it is no longer capable of being translated to synthesize a functional polypeptide product. Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target messages and inhibit translation.

Because ribozymes, unlike antisense molecules, are catalytic, a lower intracellular concentration is required for efficiency. A further aspect of the invention relates to the use of the isolated "antisense" nucleic acids to inhibit expression, e.g., by inhibiting transcription and/or translation of a subject CPR-4 or CTSB nucleic acids. The antisense nucleic acids may bind to the potential drug target by conventional base pair complementarity, or, for example, in the case of binding to DNA duplexes, through specific interactions in the major groove of the double helix. In general, these methods refer to the range of techniques generally employed in the art, and include any methods that rely on specific binding to oligonucleotide sequences.

An antisense construct of the present invention can be delivered, for example, as an expression plasmid which, when transcribed in the cell, produces RNA which is complementary to at least a unique portion of the cellular mRNA which encodes a CPR-4 or a CTSB polypeptide. Alternatively, the antisense construct is an oligonucleotide probe, which is generated ex vivo and which, when introduced into the cell causes inhibition of expression by hybridizing with the mRNA and/or genomic sequences of a CPR-4 or a CTSB nucleic acid. Such oligonucleotide probes are preferably modified oligonucleotides, which are resistant to endogenous nucleases, e.g., exonucleases and/or endonucleases, and are therefore stable in vivo. Exemplary nucleic acid molecules for use as antisense oligonucleotides are phosphoramidate, phosphothioate and methylphosphonate analogs of DNA (see also U.S. Pat. Nos. 5,176,996; 5,264, 564; and 5,256,775). Additionally, general approaches to constructing oligomers useful in antisense therapy have been reviewed, for example, by Van der Krol et al. (1988) BioTechniques 6:958-976; and Stein et al. (1988) Cancer Res 48:2659-2668.

Antisense approaches involve the design of oligonucleotides (either DNA or RNA) that are complementary to mRNA encoding a CPR-4 or a CTSB polypeptide. The antisense oligonucleotides may bind to the mRNA transcripts and prevent translation. Absolute complementarity, although preferred, is not required. In the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex. Oligonucleotides that are complementary to the 5' end of the mRNA, e.g., the 5'] untranslated sequence up to and including the AUG initiation codon, should work most efficiently at inhibiting translation. However, sequences complementary to the 3' untranslated sequences of mRNAs have been shown to be effective at inhibiting translation of mRNAs as well.

Therefore, oligonucleotides complementary to either the 5' or 3' untranslated, non-coding regions of a gene could be used in an antisense approach to inhibit translation of that mRNA. Oligonucleotides complementary to the 5' untranslated region of the mRNA should include the complement of the AUG start codon. Antisense oligonucleotides complementary to mRNA coding regions are less efficient inhibitors of translation but could also be used in accordance with the invention. Whether designed to hybridize to the 5', 3' or coding region of mRNA, antisense nucleic acids should be at least six nucleotides in length, and are preferably less that about 100 and more preferably less than about 50, 25, 17 or 10 nucleotides in length.

The antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors), or compounds facilitating transport across the cell membrane (see, e.g., Letsinger et al., 1989, Proc. Natl. Acad. Sci. U.S.A. 86:6553-6556; Lemaitre et al., 1987, Proc. Natl. Acad. Sci. 84:648-652; PCT Publication No. W088/09810, published Dec. 15, 1988) or the blood-brain barrier (see, e.g., PCT Publication No. W089110134, published Apr. 25, 1988), hybridization-triggered cleavage agents. (See, e.g., Krol et al., 1988, BioTechniques 6:958-976) or intercalating agents. (See, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to: 5-fluorouracil, 5-bromouracil, 5-chlorouracil, 5-iodouracil, hypoxanthine, xantine, 4-acetylcytosine, 5-(carboxyhydroxytiethyl) uracil, 5-carboxymethylaminomethyl-2-thiouridine, 5-carboxymethylaminomethyluracil, dihydrouracil, beta-D-galactosylqueosine, inosine, N 6-isopentenyladenine, 1-methylguanine, III methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. The antisense oligonucleotide may also comprise at least one modified sugar moiety selected from the group including but not limited to: arabinose, 2-fluoroarabinose, xylulose, and hexose. The antisense oligonucleotide can also contain a neutral peptide-like backbone. Such molecules are termed peptide nucleic acid (PNA)-oligomers and are described, e.g., in Perry-O'Keefe et al. (1996) Proc. Natl. Acad. Sci. U.S.A. 93:14670 and in Eglom et al. (1993) Nature 365:566. One advantage of PNA oligomers is their capability to bind to complementary DNA essentially independently from the ionic strength of the medium due to the neutral backbone of the DNA. In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

A further aspect of the invention relates to the use of DNA enzymes to inhibit expression of the CPR-4 gene, or the CTSB gene. DNA enzymes incorporate some of the mechanistic features of both antisense and ribozyme technologies. DNA enzymes are designed so that they recognize a particular target nucleic acid sequence, much like an antisense oligonucleotide, however much like a ribozyme they are catalytic and specifically cleave the target nucleic acid. There are currently two basic types of DNA enzymes, and both of these were identified by Santoro and Joyce (see, for example, U.S. Pat. No. 6,110,462). The 10-23 DNA enzyme comprises a loop structure which connect two arms. The two arms provide specificity by recognizing the particular target nucleic acid sequence while the loop structure provides catalytic function under physiological conditions. Briefly, to design an ideal DNA enzyme that specifically recognizes and cleaves a target nucleic acid, one of skill in the art must first identify the unique target sequence. This can be done using the same approach as outlined for antisense oligonucleotides. Preferably, the unique or substantially sequence is a G/C rich of approximately 18 to 22 nucleotides. High G/C content helps insure a stronger interaction between the DNA enzyme and the target sequence. When synthesizing the DNA enzyme, the specific antisense recognition sequence that will target the enzyme to the message is divided so that it comprises the two arms of the DNA enzyme, and the DNA enzyme loop is placed between the two specific arms. Methods of making and administering DNA enzymes can be found, for example, in U.S. Pat. No. 6,110,462. Similarly, methods of delivery of DNA ribozymes in vitro or in vivo include methods of delivery of RNA ribozyme, as outlined in detail above. Additionally, one of skill in the art will recognize that, like antisense oligonucleotide, DNA enzymes can be optionally modified to improve stability and improve resistance to degradation.

Antisense RNA and DNA, ribozyme, RNAi constructs of the invention may be prepared by any method known in the art for the synthesis of DNA and RNA molecules, including techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines. Moreover, various well-known modifications to nucleic acid molecules may be introduced as a means of increasing intracellular stability and half-life. Possible modifications include but are not limited to the addition of flanking sequences of ribonucleotides or deoxyribonucleotides to the 5' and/or 3' ends of the molecule or the use of phosphorothioate or 2' O-methyl rather than phosphodiesterase linkages within the oligodeoxyribonucleotide backbone.

In some embodiments, the agent is an aptamer. Aptamers are nucleic acid or peptide molecules that bind to a specific target molecule. Aptamers can inhibit the activity of the target molecule by binding to it.

A further aspect of the invention relates to the use of DNA editing compositions and methods to inhibit, alter, disrupt expression and/or replace one or more target genes. In various embodiments, one or more target genes may be altered through CRISPR/Cas-9, TALAN or Zinc (Zn2+) finger nuclease systems.

In some embodiments, the agent for altering gene expression is CRISPR-Cas9, or a functional equivalent thereof, together with an appropriate RNA molecule arranged to target one or more target genes, such as cpr-4, ctsb or any homolog/orthologs thereof. For example, one embodiment of the present invention may include the introduction of one or more guide RNAs (gRNAs) to be utilized by CRISPR/Cas9 system to disrupt, replace, or alter the expression or activity of one or more target genes.

In this context, the gene-editing CRISPR/cas-9 technology is an RNA-guided gene-editing platform that makes use of a bacterially derived protein (Cas9) and a synthetic guide RNA to introduce a double strand break at a specific location within the genome. Editing is achieved by transfecting a cell or a subject with the Cas9 protein along with a specially designed guide RNA (gRNA) that directs the cut through hybridization with its matching genomic sequence. By making use of this technology, it is possible to introduce specific genetic alterations in one or more target genes. In some embodiments, this CRISPR/cas-9 may be utilized to replace one or more existing wild-type genes with a modified version, while additional embodiments may include the addition of genetic elements that alter, reduce, increase or knock-out the expression of a target gene such as cpr-4, or ctsb.

In some embodiments, the agent for altering gene expression is a zinc finger, or zinc finger nuclease or other equivalent. The term "zinc finger nuclease" or "zinc finger nuclease as used herein, refers to a nuclease comprising a nucleic acid cleavage domain conjugated to a binding domain that comprises a zinc finger array. In some embodiments, the cleavage domain is the cleavage domain of the type II restriction endonuclease FokI. Zinc finger nucleases can be designed to target virtually any desired sequence in a given nucleic acid molecule for cleavage, and the possibility to design zinc finger binding domains to bind unique sites in the context of complex genomes allows for targeted cleavage of a single genomic site in living cells, for example, to achieve a targeted genomic alteration of therapeutic value. Targeting a double-strand break to a desired genomic locus can be used to introduce frame-shift mutations into the coding sequence of a gene due to the error-prone nature of the non-homologous DNA repair pathway.

Zinc finger nucleases can be generated to target a site of interest by methods well known to those of skill in the art. For example, zinc finger binding domains with a desired specificity can be designed by combining individual zinc finger motifs of known specificity. The structure of the zinc finger protein Zif268 bound to DNA has informed much of the work in this field and the concept of obtaining zinc fingers for each of the 64 possible base pair triplets and then mixing and matching these modular zinc fingers to design proteins with any desired sequence specificity has been described (Pavletich N P, Pabo Colo. (May 1991). "Zinc finger-DNA recognition: crystal structure of a Zif268-DNA complex at 2.1 A". Science 252 (5007): 809-17, the entire contents of which are incorporated herein).

In some embodiments, separate zinc fingers that each recognizes a 3 base pair DNA sequence are combined to generate 3-, 4-, 5-, or 6-finger arrays that recognize target sites ranging from 9 base pairs to 18 base pairs in length. In some embodiments, longer arrays are contemplated. In other embodiments, 2-finger modules recognizing 6-8 nucleotides are combined to generate 4-, 6-, or 8-zinc finger arrays. In some embodiments, bacterial or phage display is employed to develop a zinc finger domain that recognizes a desired nucleic acid sequence, for example, a desired nuclease target site of 3-30 bp in length.

Zinc finger nucleases, in some embodiments, comprise a zinc finger binding domain and a cleavage domain fused or otherwise conjugated to each other via a linker, for example, a polypeptide linker. The length of the linker determines the distance of the cut from the nucleic acid sequence bound by the zinc finger domain. If a shorter linker is used, the cleavage domain will cut the nucleic acid closer to the bound nucleic acid sequence, while a longer linker will result in a greater distance between the cut and the bound nucleic acid sequence. In some embodiments, the cleavage domain of a zinc finger nuclease has to dimerize in order to cut a bound nucleic acid. In some such embodiments, the dimer is a heterodimer of two monomers, each of which comprise a different zinc finger binding domain. For example, in some embodiments, the dimer may comprise one monomer comprising zinc finger domain A conjugated to a FokI cleavage domain, and one monomer comprising zinc finger domain B conjugated to a FokI cleavage domain. In this non-limiting example, zinc finger domain A binds a nucleic acid sequence on one side of the target site, zinc finger domain B binds a nucleic acid sequence on the other side of the target site, and the dimerize FokI domain cuts the nucleic acid in between the zinc finger domain binding sites.

The term "zinc finger," as used herein, refers to a small nucleic acid-binding protein structural motif characterized by a fold and the coordination of one or more zinc ions that stabilize the fold. Zinc fingers encompass a wide variety of differing protein structures (see, e.g., Klug A, Rhodes D (1987). "Zinc fingers: a novel protein fold for nucleic acid recognition". Cold Spring Harb. Symp. Quant. Biol. 52: 473-82, the entire contents of which are incorporated herein by reference). Zinc fingers can be designed to bind a specific sequence of nucleotides, and zinc finger arrays comprising fusions of a series of zinc fingers, can be designed to bind virtually any desired target sequence. Such zinc finger arrays can form a binding domain of a protein, for example, of a nuclease, e.g., if conjugated to a nucleic acid cleavage domain. Different types of zinc finger motifs are known to those of skill in the art, including, but not limited to, Cys2His2, Gag knuckle, Treble clef, Zinc ribbon, Zn2/Cys6, and TAZ2 domain-like motifs (see, e.g., Krishna S S, Majumdar I, Grishin N V (January 2003). "Structural classification of zinc fingers: survey and summary". Nucleic Acids Res. 31 (2): 532-50). Typically, a single zinc finger motif binds 3 or 4 nucleotides of a nucleic acid molecule. Accordingly, a zinc finger domain comprising 2 zinc finger motifs may bind 6-8 nucleotides, a zinc finger domain comprising 3 zinc finger motifs may bind 9-12 nucleotides, a zinc finger domain comprising 4 zinc finger motifs may bind 12-16 nucleotides, and so forth. Any suitable protein engineering technique can be employed to alter the DNA-binding specificity of zinc fingers and/or design novel zinc finger fusions to bind virtually any desired target sequence from 3-30 nucleotides in length (see, e.g., Pabo C O, Peisach E, Grant RA (2001). "Design and selection of novel cys2H is2 Zinc finger proteins". Annual Review of Biochemistry 70: 313-340; Jamieson A C, Miller J C, Pabo C O (2003). "Drug discovery with engineered zinc-finger proteins". Nature Reviews Drug Discovery 2 (5): 361-368; and Liu Q, Segal D J, Ghiara J B, Barbas C F (May 1997). "Design of polydactyl zinc-finger proteins for unique addressing within complex genomes". Proc. Natl. Acad. Sci. U.S.A. 94 (11); the entire contents of each of which are incorporated herein by reference).

Fusions between engineered zinc finger arrays and protein domains that cleave a nucleic acid can be used to generate a "zinc finger nuclease." A zinc finger nuclease typically comprises a zinc finger domain that binds a specific target site within a nucleic acid molecule, and a nucleic acid cleavage domain that cuts the nucleic acid molecule within or in proximity to the target site bound by the binding domain. Typical engineered zinc finger nucleases comprise a binding domain having between 3 and 6 individual zinc finger motifs and binding target sites ranging from 9 base pairs to 18 base pairs in length. Longer target sites are particularly attractive in situations where it is desired to bind and cleave a target site that is unique in a given genome.

In some embodiments, the agent for altering the target gene is a TALEN system or its equivalent. The term TALEN or "Transcriptional Activator-Like Element Nuclease" or "TALE nuclease" as used herein, refers to an artificial nuclease comprising a transcriptional activator like effector DNA binding domain to a DNA cleavage domain, for example, a FokI domain. A number of modular assembly schemes for generating engineered TALE constructs have been reported (Zhang, Feng; et. al. (February 2011). "Efficient construction of sequence-specific TAL effectors for modulating mammalian transcription". Nature Biotechnology 29 (2): 149-53; Geibler, R.; Scholze, H.; Hahn, S.; Streubel, J.; Bonas, U.; Behrens, S. E.; Boch, J. (2011), Shiu, Shin-Han. ed. "Transcriptional Activators of Human Genes with Programmable DNA-Specificity". PLoS ONE 6 (5): e19509; Cermak, T.; Doyle, E. L.; Christian, M.; Wang, L.; Zhang, Y.; Schmidt, C.; Baller, J. A.; Somia, N. V. et al. (2011). "Efficient design and assembly of custom TALEN and other TAL effector-based constructs for DNA targeting". Nucleic Acids Research; Morbitzer, R.; Elsaesser, J.; Hausner, J.; Lahaye, T. (2011). "Assembly of custom TALE-type DNA binding domains by modular cloning". Nucleic Acids Research; Li, T.; Huang, S.; Zhao, X.; Wright, D. A.; Carpenter, S.; Spalding, M. H.; Weeks, D. P.; Yang, B. (2011). "Modularly assembled designer TAL effector nucleases for targeted gene knockout and gene replacement in eukaryotes". Nucleic Acids Research; Weber, E.; Gruetzner, R.; Werner, S.; Engler, C.; Marillonnet, S. (2011). Bendahmane, Mohammed. ed. "Assembly of Designer TAL Effectors by Golden Gate Cloning". PLoS ONE 6 (5): e19722; each of which is incorporated herein by reference).

Those of skill in the art will understand that TALE nucleases can be engineered to target virtually any genomic sequence with high specificity, and that such engineered nucleases can be used in embodiments of the present technology to manipulate the genome of a cell, e.g., by delivering the respective TALEN via a method or strategy disclosed herein under circumstances suitable for the TALEN to bind and cleave its target sequence within the genome of the cell. In some embodiments, the delivered TALEN targets a gene or allele associated with a disease or disorder or a biological process, such as RIBE, or one or more target genes. In some embodiments, delivery of the TALEN to a subject confers a therapeutic benefit to the subject, such as reducing, ameliorating or eliminating RIBE in a patient.

In some embodiments, the target gene of a cell, tissue, organ or organism is altered by a nuclease delivered to the cell via a strategy or method disclosed herein, e.g., CRISPR/cas-9, a TALEN, or a zinc-finger nuclease, or a plurality or combination of such nucleases. In some embodiments, a single- or double-strand break is introduced at a specific site within the genome by the nuclease, resulting in a disruption of the target genomic sequence.

In some embodiments, the target genomic sequence is a nucleic acid sequence within the coding region of a target gene. In some embodiments, the strand break introduced by the nuclease leads to a mutation within the target gene that impairs the expression of the encoded gene product. In some embodiments, a nucleic acid is co-delivered to the cell with the nuclease. In some embodiments, the nucleic acid comprises a sequence that is identical or homologous to a sequence adjacent to the nuclease target site. In some such embodiments, the strand break affected by the nuclease is repaired by the cellular DNA repair machinery to introduce all or part of the co-delivered nucleic acid into the cellular DNA at the break site, resulting in a targeted insertion of the co-delivered nucleic acid, or part thereof. In some embodiments, the insertion results in the disruption or repair of the undesired allele. In some embodiments, the nucleic acid is co-delivered by association to a supercharged protein. In some embodiments, the supercharged protein is also associated to the functional effector protein, e.g., the nuclease. In some embodiments, the delivery of a nuclease to a target cell results in a clinically or therapeutically beneficial alteration of the function of a gene.

In some embodiments, cells from a subject are obtained and a nuclease or other effector protein is delivered to the cells by a system or method provided herein ex vivo. In some embodiments, the treated cells are selected for those cells in which a desired nuclease-mediated genomic editing event has been affected. In some embodiments, treated cells carrying a desired genomic mutation or alteration are returned to the subject they were obtained from.

The term "therapeutically effective amount" of an agent of this invention means an amount effective to improve the response of the patient to radiation therapy having cancer or other disease condition, reducing RIBE after radiation therapy or radiation exposure, decreased cancer resistance to radiation or chemotherapy, improved efficacy of radiation and chemotherapy, increased ability to tolerate higher doses of radiation therapy. Such amounts may comprise from about 0.001 to about 500 mg or even 1000 mg or more of the compound per kilogram of body weight of the subject to which the composition is administered. Therapeutically effective amounts can be administered according to any dosing regimen satisfactory to those of ordinary skill in the art.

For example, an effective dosage for humans includes a dosage of about 50 mg/kg body weight, which would translate to about 3750 mg per day for a 75 kg human. An effective amount of quercetin includes between about 100 mg/day (0.1 g/day) and about 50000 mg/day (50 g/day), preferably between about 1000 mg/day and 30000 mg/day, more preferably between about 1000 mg/day and about 15000 mg/day, yet more preferably 1000 mg/day and about 5000 mg/day. In an exemplary embodiment, quercetin is provided to a human subject in a dosage of between 100 mg and 2000 mg/day. Dosage is related to the body mass, health status, age and the desired effect relative to an individual. Therefore, the dosage may be varied according to the administration schedule, body mass, age or the like. The dosages set forth herein are safe even for an adult of low body mass, e.g. a 100 pound adult. No toxic effects at the highest dosage set forth herein are known. However, the dosages set forth herein are preferably administered at the lower dosages for subjects having a smaller body weight and at higher dosages for subjects having a larger body weight.

In some embodiments, the agent is administered to the subject in a pharmaceutical composition, such as quercetin, isoquercetin, or an analog/derivative thereof and/or E64, CA074, or CA074Me and their analogs, in a preferred embodiment. Thus, also provided herein are pharmaceutical compositions containing agents of the invention and a pharmaceutically-acceptable carrier, which are generally accepted in the art for the delivery of biologically active agents to animals, in particular, humans. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication commensurate with a reasonable benefit/risk ratio.

The agent, which in a preferred embodiment may include quercetin, isoquercetin, or an analog/derivative thereof, may be administered in the form of pharmaceutically acceptable salts or prodrugs. The term "pharmaceutically-acceptable salts" refer to derivatives of the disclosed agents or compounds wherein the agent or parent compound is modified by making acid or base salts thereof. Examples of pharmaceutically acceptable salts include, but are not limited to, mineral or organic acid salts of basic residues such as amines, or alkali or organic salts of acidic residues such as carboxylic acids. Pharmaceutically-acceptable salts include the conventional non-toxic salts or the quaternary ammonium salts of the parent compound formed, for example, from non-toxic inorganic or organic acids. Such conventional nontoxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamolc, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Pharmaceutically acceptable salts are those forms of agents, suitable for use in contact with the tissues of human beings and animals without excessive toxicity, irritation, allergic response, or other problem or complication, commensurate with a reasonable benefit/risk ratio.

Pharmaceutically-acceptable salt forms may be synthesized from the agents that contain a basic or acidic moiety by conventional chemical methods. Generally, such salts are, for example, prepared by reacting the free acid or base forms of these agents with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in at page 1418 of Remington's Pharmaceutical Sciences, 17th ed., Mack Publishing Company, Easton, Pa., 1985.

"Pro-drugs" are intended to include any covalently bonded carriers that release an active parent drug or agent of the present invention in vivo when such prodrug is administered to a mammalian subject. Since prodrugs are known to enhance numerous desirable qualities of pharmaceuticals (i.e., solubility, bioavailability, half-life, manufacturing, etc.) the agents of the present invention may be delivered in prodrug form. Thus, the present invention is intended to cover prodrugs of the presently claimed compounds, methods of delivering the same, and compositions containing the same.

Prodrugs of the present invention are prepared by modifying functional groups present in the agent in such a way that the modifications are cleaved, either in routine manipulation or in vivo, to an active agent. Prodrugs include agents of the present invention wherein an acyl, hydroxy, amino, or sulfhydryl group is bonded to any group that, when the prodrug of the present invention is administered to a mammalian subject, is cleaved to form a free acetyl, hydroxyl, free amino, or free sulfydryl group, respectively. Examples of prodrugs include, but are not limited to, acetate, formate, and benzoate derivatives of alcohol and amine functional groups in the agents of the present invention. It will be appreciated by those skilled in the art that some of the agents having a chiral center may exist in, and may be isolated in, optically active and racemic forms.

In one preferred embodiment, the invention may include pharmaceutical formulations of, for example, quercetin analogs that are capable of acting as prodrugs which can be biologically degraded or broken down to release quercetin within the body after being administered to a patient in need of treatment. Thus, the invention also includes pharmaceutical compositions comprising or containing quercetin analogues or derivatives providing prodrugs made up or formulated for administration in any suitable manner in the course of medical or veterinary treatment, for example parentally (including intravenously, intramuscularly and subcutaneously) or orally. Such compositions containing or incorporating, conveniently in unit dosage form, therapeutically effective non-toxic amounts of the prodrug compound, or the equivalent of therapeutically effective non-toxic amounts of the active drug compound, together possibly with at least one other ingredient providing a compatible pharmaceutically acceptable additive, carrier, diluent or excipient, may be prepared by any of the methods well known in the art of pharmacy as generally described herein.

It is to be understood that the term "agent" of the present invention encompasses any racemic, optically-active, regioisomeric or stereoisomeric form, or mixtures thereof, which possess the therapeutically useful properties described herein. It is well known in the art how to prepare optically active forms (for example, by resolution of the racemic form by recrystallization techniques, by synthesis from optically-active starting materials, by chiral synthesis, or by chromatographic separation using a chiral stationary phase).

It is also to be understood that the scope of this invention encompasses not only the various isomers, which may exist but also the various mixtures of isomers, which may be formed. For example, if the compound of the present invention contains one or more chiral centers, the compound can be synthesized enantioselectively or a mixture of enantiomers and/or diastereomers can be prepared and separated. The resolution of the compounds of the present invention, their starting materials and/or the intermediates may be carried out by known procedures, e.g., as described in the four-volume compendium Optical Resolution Procedures for Chemical Compounds: Optical Resolution Information Center, Manhattan College, Riverdale, N.Y., and in Enantiomers, Racemates and Resolutions, Jean Jacques, Andre Collet and Samuel H. Wilen; John Wiley & Sons, Inc., New York, 1981, which is incorporated in its entirety by this reference.

The resolution of the agents is generally based on the differences in the physical properties of diastereomers by attachment, either chemically or enzymatically, of an enantiomerically pure moiety resulting in forms that are separable by fractional crystallization, distillation or chromatography. The agents, including the salts and prodrugs of these agents, of the present invention may be purchased commercially or may also be prepared in ways well known to those skilled in them art of organic synthesis. It is understood by one skilled in the art of organic synthesis that the functionality present on various portions of the molecule must be compatible with the reagents and reactions proposed. Such restrictions to the substituents, which are compatible with the reaction conditions, will be readily apparent to one skilled in the art and alternate methods must then be used.

Pharmaceutically-acceptable carriers are formulated according to a number of factors well within the purview of those of ordinary skill in the art to determine and accommodate. These include, without limitation: the type and nature of the agent; the subject to which the agent-containing composition is to be administered; the intended route of administration of the composition; and, the therapeutic indication being targeted. Pharmaceutically-acceptable carriers include both aqueous and non-aqueous liquid media, as well as a variety of solid and semi-solid dosage forms. Such carriers can include a number of different ingredients and additives in addition to an active agent such as quercetin, and/or E64, CA074, or CA074Me and their analogs such additional ingredients being included in the formulation for a variety of reasons, e.g., stabilization of the active agent, well known to those of ordinary skill in the art. Descriptions of suitable pharmaceutically-acceptable carriers, and factors involved in their selection, are found in a variety of readily available sources, such as Remington's Pharmaceutical Sciences, 17th ed., Mack Publishing Company, Easton, Pa., 1985. Administration may be, for example, by various parenteral means. Pharmaceutical compositions suitable for parenteral administration include various aqueous media such as aqueous dextrose and saline solutions; glycol solutions are also useful carriers, and preferably contain a water-soluble salt of the active agent, suitable stabilizing compounds, and if necessary, buffering compounds. Anti-oxidizing compounds, such as sodium bisulfite, sodium sulfite, or ascorbic acid, either alone or in combination, are suitable stabilizing compounds; also used are citric acid and its salts, and EDTA. In addition, parenteral solutions can contain preservatives such as benzalkonium chloride, methyl- or propyl-paraben, and chlorobutanol.

Alternatively, compositions may be administered orally in solid dosage forms, such as capsules, tablets and powders; or in liquid forms such as elixirs, syrups, and/or suspensions. Gelatin capsules can be used to contain the active ingredient and a suitable carrier such as, but not limited to, lactose, starch, magnesium stearate, stearic acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

A preferred formulation of the invention is a mono-phasic pharmaceutical composition suitable for parenteral or oral administration, consisting essentially of a therapeutically-effective amount of an agent of the invention, and a pharmaceutically acceptable carrier. Another preferred formulation of the invention is a mono-phasic pharmaceutical composition, consisting essentially of a therapeutically-effective amount of a prodrug of an agent of the invention, and a pharmaceutically acceptable carrier. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as wetting agents, emulsifying agents and dispersing agents. It may also be desirable to include isotonic agents, such as sugars, sodium chloride, and the like in the compositions. In addition, prolonged absorption of the injectable pharmaceutical form may be brought about by the inclusion of agents which delay absorption such as aluminum monosterate and gelatin.

In some cases, in order to prolong the effect of an agent like quercetin, it is desirable to slow the absorption of the agent from subcutaneous or intramuscular injection. This may be accomplished by the use of a liquid suspension of crystalline or amorphous material having poor water solubility. The rate of absorption of the agent then depends upon its rate of dissolution, which in turn may depend upon crystal size and crystalline form. Alternatively, delayed absorption of a parenterally-administered agent is accomplished by dissolving or suspending the agent in an oil vehicle.

Injectable depot forms are made by forming microencapsulated matrices of the agent in biodegradable polymers such as polylactide-polyglycolide. Depending on the ratio of agent to polymer, and the nature of the particular polymer employed, the rate of agent release can be controlled. Examples of other biodegradable polymers include poly (orthoesters) and poly(anhydrides). Depot injectable formulations are also prepared by entrapping the agent in liposomes or microemulsions which are compatible with body tissue. The injectable materials can be sterilized for example, by filtration through a bacterial-retaining filter.

For preparing solid compositions such as tablets, the principal active ingredient is mixed with a pharmaceutical excipient to form a solid preformulation composition containing a homogeneous mixture of an agent, such as quercetin, isoquercetin or an analog, and/or E64, CA074, or CA074Me and their analogs thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg or more of the therapeutic compounds of the present invention. Formulations suitable for oral administration may be in the form of capsules, cachets, pills, tablets, powders, granules or as a solution or a suspension in an aqueous or non-aqueous liquid, or an oil-in-water or water-in-oil liquid emulsions, or as an elixir or syrup, or as pastilles (using an inert base, such as gelatin and glycerin, or sucrose and acacia), and the like, each containing a predetermined amount of an agent of the present invention as an active ingredient. An agent or agents of the present invention may also be administered as bolus, electuary or paste.

In solid dosage forms of the agents for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monosterate; (8) absorbents, such as kaolin and bentonite clay; (9) lubricants, such as talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may be employed as fillers in soft and hard-filled gelatin capsules using such excipients as lactose or milk sugars, as well as high molecular weight polyethylene glycols and the like.

A tablet may be made by compression or molding optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent. The tablets, and other solid dosage forms of the pharmaceutical compositions such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter. These compositions may also optionally contain opacifying agents and may be of a composition that they release the active ingredient only, or preferentially, in a certain portion of the gastrointestinal tract, optionally, in a delayed manner. Examples of embedding compositions which can be used include polymeric substances and waxes. The active ingredient can also be in microencapsulated form. The tablets or pills may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Liquid dosage forms for oral administration of the agents include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents. Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches, drops and inhalants. The active ingredient may be mixed under sterile conditions with a pharmaceutically-acceptable carrier, and with any buffers, or propellants which may be required. The ointments, pastes, creams and gels may contain, in addition to an active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof. Powders and sprays can contain, in addition to an active ingredient, excipients such as lactose, talc, silicic acid, aluminum hydroxide, calcium silicates and polyamide powder or mixtures of these substances. Sprays can additionally contain customary propellants such as chlorofluorohydrocarbons and volatile unsubstituted hydrocarbons, such as butane and propane. Transdermal patches have the added advantage of providing controlled delivery of compounds of the invention to the body. Such dosage forms can be made by dissolving, dispersing or otherwise incorporating one or more agents in a proper medium, such as an elastomeric matrix material.

Absorption enhancers can also be used to increase the flux of the compound across the skin. The rate of such flux can be controlled by either providing a rate-controlling membrane or dispersing the compound in a polymer matrix or gel. Pharmaceutical formulations further include those suitable for administration by inhalation or insufflation or for nasal or intraocular administration. For administration to the upper (nasal) or lower respiratory tract by inhalation, the agents may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide, or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of one or more of the agents and a suitable powder base, such as lactose or starch. The powder composition may be presented in unit dosage form in, for example, capsules or cartridges, or, e.g., gelatin or blister packs from which the powder may be administered with the aid of an inhalator, insufflator or a metered-dose inhaler. For intranasal administration, compounds of the invention may be administered by means of nose drops or a liquid spray, such as by means of a plastic bottle atomizer or metered-dose inhaler.

Drops, such as eye drops or nose drops, may be formulated with an aqueous or nonaqueous base also comprising one or more dispersing agents, solubilizing agents or suspending agents. Liquid sprays are conveniently delivered from pressurized packs. Drops can be delivered by means of a simple eye dropper-capped bottle or by means of a plastic bottle adapted to deliver liquid contents dropwise by means of a specially shaped closure. Any formulations may be presented in unit-dose or multi-dose sealed containers, for example, ampules and vials, and may be stored in a lyophilized condition requiring only the addition of the sterile liquid carrier, for example water for injection, immediately prior to use. Extemporaneous injection solutions and suspensions may be prepared from sterile powders, granules and tablets of the type described above.

The dosage formulations provided by this invention may contain the therapeutic compounds of the invention, either alone or in combination with other therapeutically active ingredients, and pharmaceutically acceptable inert excipients. The dosage formulations may contain one or more of antioxidants, chelating agents, diluents, binders, lubricants/glidants, disintegrants, coloring agents and release modifying polymers. Suitable antioxidants may be selected from amongst one or more pharmaceutically acceptable antioxidants known in the art. Examples of pharmaceutically acceptable antioxidants include butylated hydroxyanisole (BHA), sodium ascorbate, butylated hydroxytoluene (BHT), sodium sulfite, citric acid, malic acid and ascorbic acid. The antioxidants may be present in the dosage formulations of the present invention at a concentration between about 0.001% to about 5%, by weight, of the dosage formulation.

Suitable chelating agents may be selected from amongst one or more chelating agents known in the art. Examples of suitable chelating agents include disodium edetate (EDTA), edetic acid, citric acid and combinations thereof. The chelating agents may be present in a concentration between about 0.001% and about 5%, by weight, of the dosage formulation.

Suitable diluents such as lactose, sugar, cornstarch, modified cornstarch, mannitol, sorbitol, and/or cellulose derivatives such as wood cellulose and microcrystalline cellulose, typically in an amount within the range of from about 20% to about 80%, by weight.

Examples of suitable binders include methyl cellulose, hydroxypropyl cellulose, hydroxypropylmethyl cellulose, polyvinyl pyrrolidone, eudragits, ethyl cellulose, gelatin, gum arabic, polyvinyl alcohol, pullulan, carbomer, pregelatinized starch, agar, tragacanth, sodium alginate, microcrystalline cellulose and the like. Examples of suitable disintegrants include sodium starch glycolate, croscarmellose sodium, crospovidone, low substituted hydroxypropyl cellulose, and the like. The concentration may vary from 0.1% to 15%, by weight, of the dosage form.

Examples of lubricants/glidants include colloidal silicon dioxide, stearic acid, magnesium stearate, calcium stearate, talc, hydrogenated castor oil, sucrose esters of fatty acid, microcrystalline wax, yellow beeswax, white beeswax, and the like. The concentration may vary from 0.1% to 15%, by weight, of the dosage form. Release modifying polymers may be used to form extended release formulations containing the therapeutic compounds of the invention. The release modifying polymers may be either water-soluble polymers, or water insoluble polymers. Examples of water-soluble polymers include polyvinylpyrrolidone, hydroxy propylcellulose, hydroxypropyl methylcellulose, vinyl acetate copolymers, polyethylene oxide, polysaccharides (such as alginate, xanthan gum, etc.), methylcellulose and mixtures thereof. Examples of water insoluble polymers include acrylates such as methacrylates, acrylic acid copolymers; cellulose derivatives such as ethylcellulose or cellulose acetate; polyethylene, and high molecular weight polyvinyl alcohols.

Optionally, the therapeutic methods and compositions, such as quercetin and/or E64, CA074, or CA074Me and their analogs, of the present invention may be combined with other anti-cancer therapies and RIBE treatments. Examples of anti-cancer therapies include traditional cancer treatments such as surgery and chemotherapy, as well as other new treatments. Such other anti-cancer therapies will be expected to act in an additive or synergistic manner with the radiation therapy. This may result in better control of the cancer as well as reducing the need for high dosages and/or allowing for higher doses of therapeutic radiation by reducing RIBE. For example, a wide array of conventional compounds, have been shown to have anti-cancer activities. These compounds have been used as pharmaceutical agents in chemotherapy to shrink solid tumors, prevent metastases and further growth, or decrease the number of malignant cells in leukemic or bone marrow malignancies.

Although chemotherapy has been effective in treating various types of malignancies, many anti-cancer compounds induce undesirable side effects. It has been shown that when two or more different treatments are combined, the treatments may work synergistically and allow reduction of dosage of each of the treatments, thereby reducing the detrimental side effects exerted by each compound at higher dosages. In other instances, malignancies that are refractory to a treatment may respond to a combination therapy of two or more different treatments. Another embodiment of the invention relates to the use of any of the compositions described, such as quercetin, isoquercetin, or an analog thereof, in the preparation of a medicament for improving the response of a cancer patient to radiation therapy and/or decreasing RIBE effects.

The term "including" is used herein to mean, and is used interchangeably with, the phrase "including but not limited to." The term "or" is used herein to mean, and is used interchangeably with, the term "and/or," unless context clearly indicates otherwise.

The invention now being generally described will be more readily understood by reference to the following examples, which are included merely for the purposes of illustration of certain aspects of the embodiments of the present invention. The examples are not intended to limit the invention, as one of skill in the art would recognize from the above teachings and the following examples that other techniques and methods can satisfy the claims and can be employed without departing from the scope of the claimed invention.

The present invention is further illustrated in the following examples, which should not be taken to limit the scope of the invention.

EXAMPLES

Figure 5:
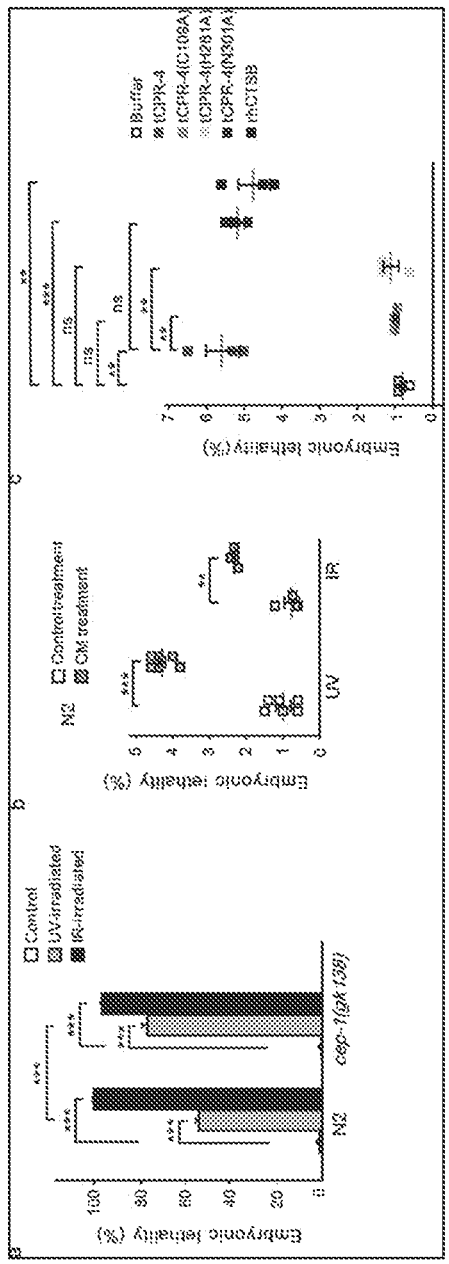
FIG. 5: Conditioned medium generated from UV or ionizing irradiation (IR) and purified tCPR-4 proteins cause embryonic lethality. (5a). The embryonic lethality rate of wild type (N2) or cep-1(gk138) animals after 100 J/m$^2$ UV irradiation or 500 Gy IR compared with sham-irradiation controls. (5b). N2 animals were used to generate UV-CM, UV-control, IR-CM and IR-control, which were used to treat unexposed N2 animals in the embryonic lethality assays. (5c). 2.8 μM of recombinant tCPR-4 proteins (wild-type or mutant), 0.27 μM recombinant human Cathepsin B (rhCTSB), or the buffer control were used to treat N2 animals in the embryonic lethality assays. Total numbers of embryos scored: 1781, 805, 1249, 2645, 596, and 1862 embryos, from the left bar to the right bar in a; 2721, 2484, 880, and 743, from left to right in b; and 979, 875, 929, 939, 907, and 777, from left to right in c. Six independent assays (a, UV-Ctrl and UV-CM in b) and three independent assays (IR-Ctrl and IR-CM in b, c) were performed for each condition. Data are mean±s.e.m. P<0.01, *P<0.001, "ns" is non-significant, two-sided, unpaired t test.

Example 1: This Example Illustrates the Production and Excretion of One or More RIBE Factors in Response to Irradiation The present inventors tested whether C. elegans could serve as an animal model to study RIBE using UV radiation, because UV-induced damage in C. elegans is well characterized. Wild-type (N2) animals cultured in the liquid S-Medium were irradiated with 100 J/m$^2$ UV or sham-irradiated. This UV dosage induced significant embryonic lethality (FIG. 5a), which was exacerbated in cep-1(gk138) animals defective in the C. elegans p53 homolog CEP-1 that is involved in DNA damage repair. The medium used to culture irradiated and sham-irradiated animals was called "UV conditioned medium" (UV-CM) and "UV control" (UV-Ctrl), respectively, and used to treat unexposed animals (FIG. 1a). N2 animals treated with UV-CM showed increased embryonic lethality compared with those treated with UV-Ctrl (FIG. 5b), indicating that UV-CM contains substances capable of inducing damage in unexposed animals. UV-CM also reduced germ cell death in ced-1(e1735) animals, which have many unengulfed apoptotic cells that sensitizes detection of apoptosis, in a manner dependent on the UV dosages (FIG. 1b), reaching maximal death inhibitory activity at 100 J/m$^2$. These results are consistent with published reports that reduced apoptosis or increased survival of unexposed cells is one of the endpoints of RIBE.

Figure 6:
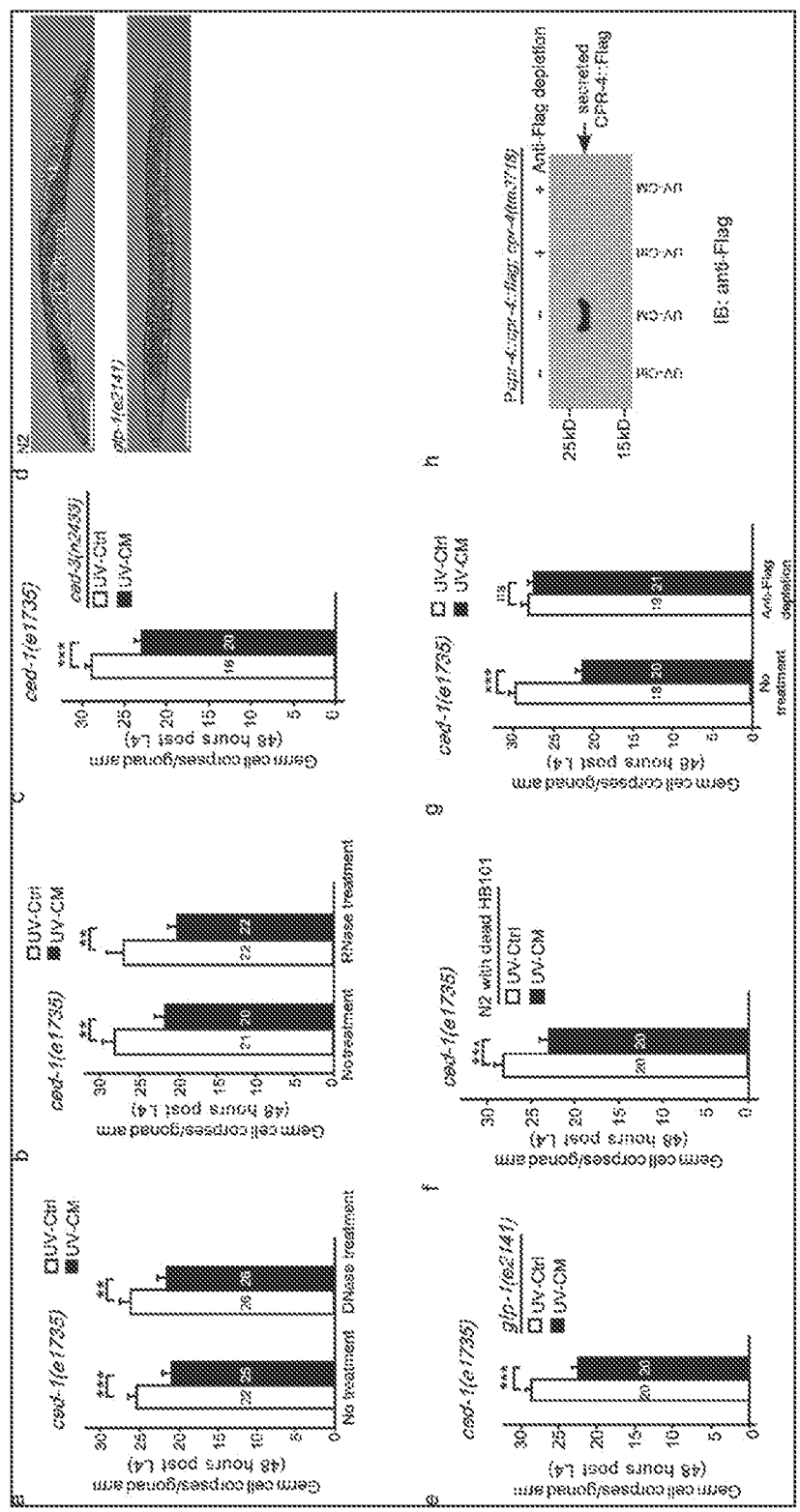
FIG. 6: Characterization of the nature and the source of the RIBE factors. (6a-b). Treatment of UV-CM and UV-Ctrl collected from N2 animals irradiated at 100 J/m$^2$ with RNase (1 µg/µL) or DNase (0.01 Unit/µL) did not alter the apoptosis-inhibitory effect on ced-1(e1735) animals. Germ cell corpses were scored after 48-hour treatment of ced-1(e1735) L4 larvae. (6c, 6e-g). Here ced-1(e1735) L4 larvae were treated with UV-CM and UV-control (0.1 µg/µL) prepared from ced-3(n2433) animals (c), glp-1(e2141ts) animals grown at 25° C. (e), N2 animals fed with formaldehyde-treated HB101 bacteria (f), and Pcpr-4::cpr-4::flag; cpr-4 (tm3718) animals with or without anti-Flag depletion (g), respectively. Data are mean±s.e.m. The numbers of gonad arms scored are indicated inside the bars (a-c, e-g). P<0.01, *P<0.001, "ns", non-significant, two-sided, unpaired t test. (6d). Representative differential interference contrast (DIC) images (at least 10) of N2 and glp-1(e2141) adult animals grown at 25° C. The gonads of the N2 animal with multiple oocytes and fertilized eggs are outlined with dash lines. glp-1(e2141) animal had no visible germline. Scale bars indicate 100 µm. (6h). Immunoblotting analysis of secreted CPR-4::Flag in UV-CM and UV-Ctrl prepared from Pcpr-4::cpr-4::flag; cpr-4(tm3718) animals with or without anti-Flag depletion treatment.

Example 2: This Example Illustrates the Identification of the RIBE Factors as Proteins Generated by Irradiated Cells and not Other Factors The present inventors probed the nature of RIBE factors by treating UV-CM with enzymes that destroy DNA, RNA or proteins. The apoptosis-inhibitory activity in UV-CM was resistant to treatment of DNase or RNase (FIG. 6a, b), but obliterated by the Trypsin protease (FIG. 1c), suggesting that the RIBE factors are proteins. UV-CM collected from cell-death defective ced-3(n2433) animals, germline-deficient glp-1(e2141) animals, or N2 animals fed with dead bacteria retained the death inhibitory activity (FIG. 6c-f), indicating that the RIBE factors are unlikely factors generated by bacteria or byproducts of cell death induced by radiation and can be made without the germline.

Figure 7:
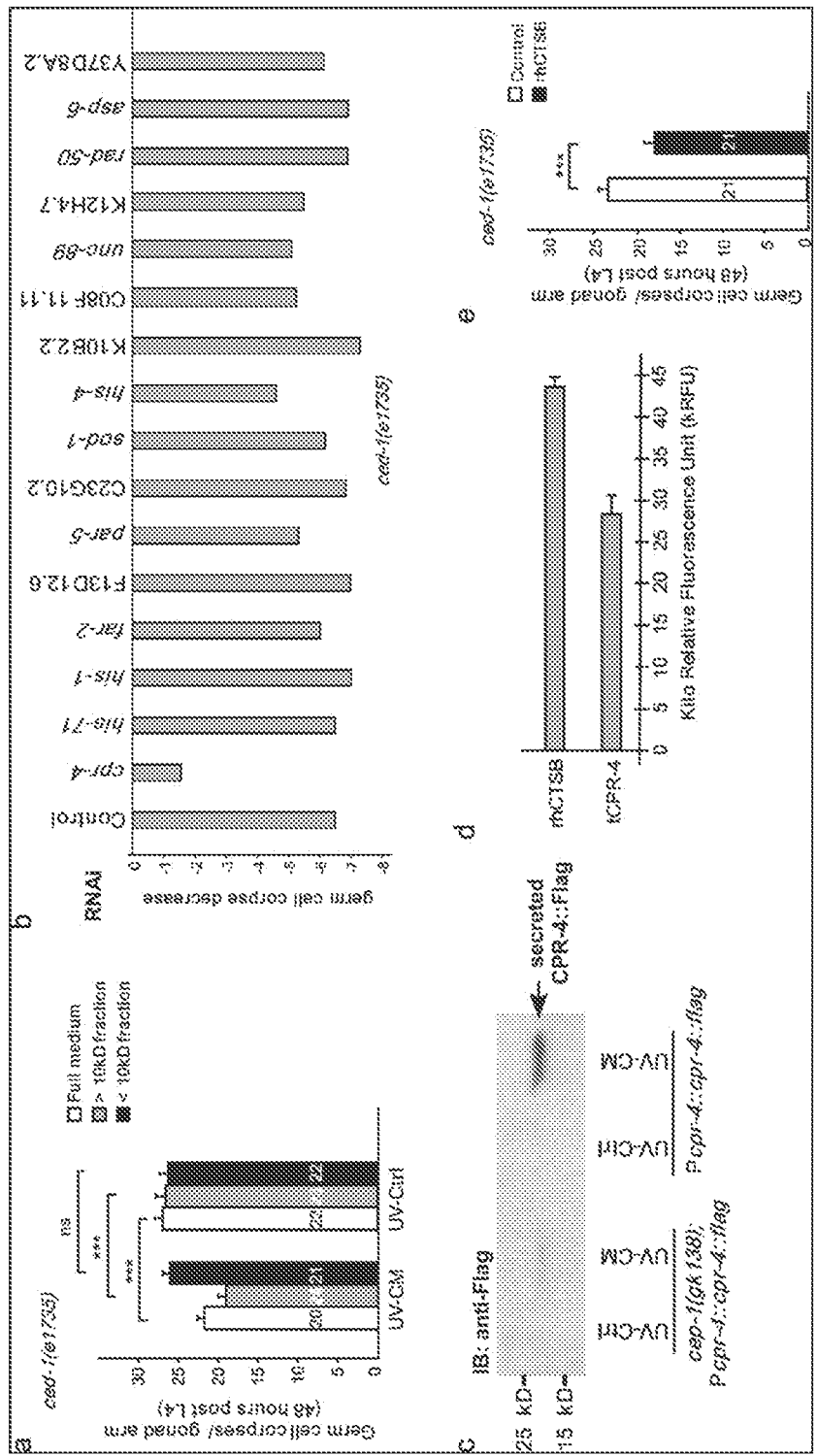
FIG. 7: Identification of CPR-4 as the RIBE factor. (7a). Full medium, >10 kD fraction, and <10 kD fraction of UV-CM and UV-Ctrl derived from N2 animals were used to treat ced-1(e1735) animals in germ cell corpse assays as in FIG. 1b. Data are mean±s.e.m. The numbers of gonad arms scored are indicated inside the bars. (7b). Identification of CPR-4 as the RIBE factor through the RNAi screen. UV-Ctrl and UV-CM prepared from RNAi-treated animals were used to treat ced-1(e1735) animals. The number of germ cell corpse decrease (y axis) was calculated by subtracting the number of average germ cell corpses under UV-Ctrl treatment from that under UV-CM treatment. Among the candidate genes, RNAi of eft-3, ubq-2 and act-1 caused strong embryonic lethality and the present inventors were unable to obtain their UV-CM. RNAi of his-1, his-4 and his-71 caused partial embryonic lethality. 20 gonad arms were scored in each RNAi experiment. (7c). Secretion of CPR-4::Flag into UV-CM was greatly reduced in irradiated cep-1(gk138) animals carrying a single copy integration of Pcpr-4::cpr-4::flag compared with that from irradiated N2 animals carrying the same Pcpr-4::cpr-4::flag transgene. Concentrated UV-CM or UV-control (1 µg/µL) from the indicated strains was subjected to the immunoblotting analysis using an antibody to the Flag epitope. (7d). The protease activity of 0.27 µM recombinant human Cathepsin B (rhCTSB) or 2.8 µM recombinant tCPR-4 protein was measured as in FIG. 2b. Data are mean±s.e.m. (n=6 in each assay). (7e). 0.27 µM of rhCTSB or the buffer control were used to treat ced-1(e1735) animals. Animals cultured in the rhCTSB buffer grew slower than in the tCPR-4 buffer and had less germ cell corpses. Data are mean±s.e.m. (n=21 in each assay). Germ cell corpses were scored after 48-hour treatment (a, b, e). ***P<0.001, "ns", non-significant, two-sided, unpaired t test (a, e).
Figure 8:
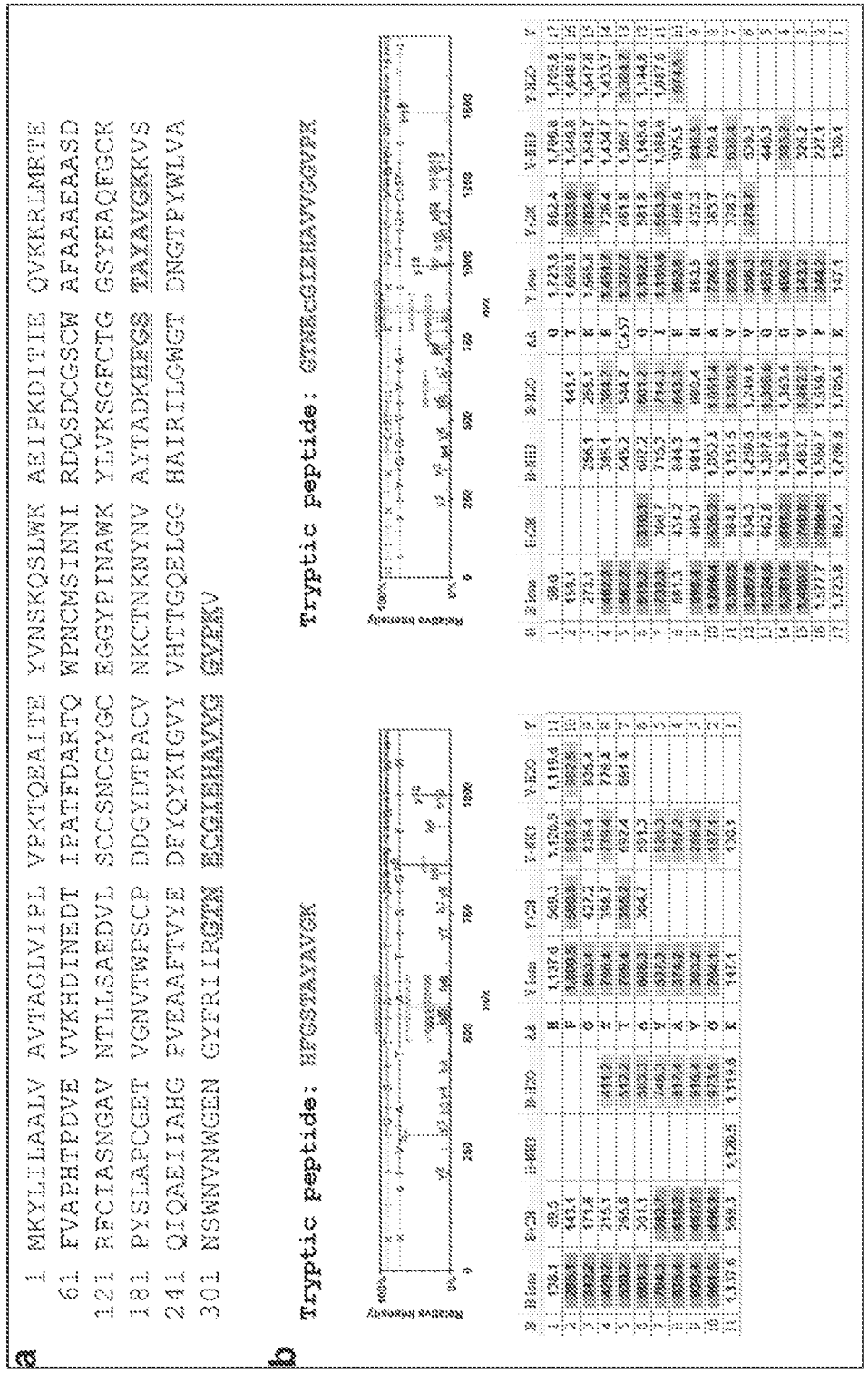
FIG. 8: Representative MS/MS spectra from LTQ-Orbitrap used to confirm the identity of CPR-4 in UV-CM. (8a). Tryptic peptides of protein band 6 in the SDS PAGE gel (FIG. 1d) were analyzed by LC-MS/MS using LTQ-Orbitrap. The amino acid sequences of peptides identified by MS/MS analysis and matched to the amino acid sequences of CPR-4 are underlined and in Red. (8b).—The MS/MS spectra of the two peptides identified in a are shown. The assignments of the fragmented ions observed to specific amino acid residues were performed using the Scaffold 3 search engine, and the search results are shown below the MS/MS spectra. The lower case "c" indicates the carbamidomethyl-modified cysteine residue in the tryptic peptide.

Using 10 kD molecular weight cut-off filter units, the present inventors separated UV-CM into two fractions, one containing proteins likely larger than 10 kD and one with proteins smaller than 10 kD. The RIBE activity appeared in the >10 kD fraction (FIG. 7a), which were resolved on a SDS polyacrylamide gel (FIG. 1d). Protein bands unique to UV-CM were analyzed by mass-spectrometry, from which 19 proteins were identified (FIG. 1e; FIG. 8 and Table 5).

Figure 9:
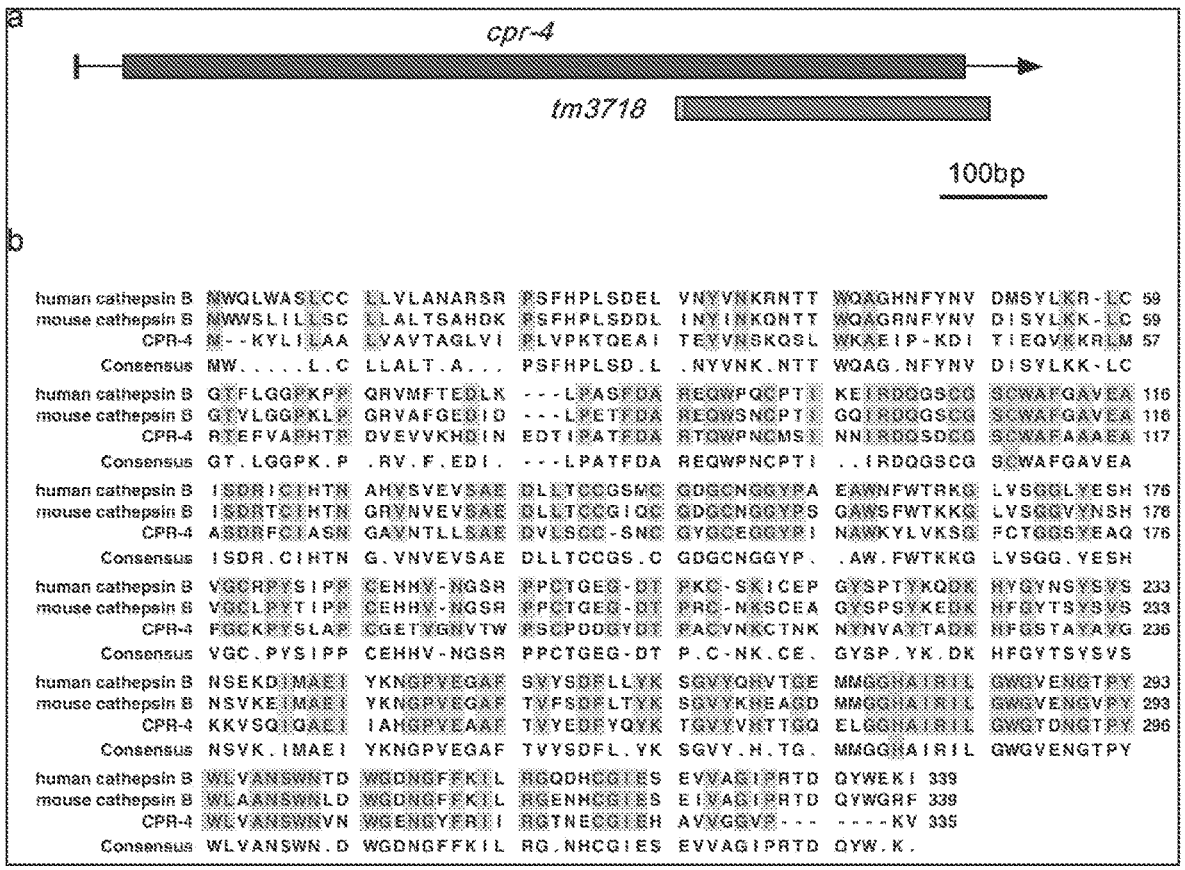
FIG. 9: The cpr-4 deletion mutation and sequence alignment of human and mouse cathepsin B and CPR-4. (9a). A schematic representation of the cpr-4 gene structure and the tm3718 deletion. Exons are depicted as blue boxes and introns and the untranslated region as lines. The red box indicates the region of cpr-4 removed by the 406 bp tm3718 deletion. The green box indicates a 12 bp insertion. (9b). Sequence alignment of human cathepsin B, mouse cathepsin B, and CPR-4. Residues that are identical in all three proteins are shaded in pink. The two catalytic residues are shaded in green, which are the active-site Cysteine residue that serves as a nucleophile and the Histidine residue that acts as a general base to facilitate hydrolysis of the peptide bonds of the substrates, respectively.

Example 3: This Example Illustrates the Identification of CPR-4 as a RIBE Factor The present inventors used RNA interference (RNAi) to examine if one of the 19 genes is responsible for RIBE. UV-CM from cpr-4 RNAi-treated animals displayed a greatly reduced RIBE activity, whereas UV-CM from animals treated with RNAi of other genes retained the RIBE activity (FIG. 7b). cpr-4 encodes a homolog of the mammalian cathepsin B lysosomal protease, which is secreted to act as an extracellular protease. Because a deletion mutation (tm3718) in cpr-4, which removes one third of the CPR-4 protein (FIG. 9a), obliterated the RIBE activity and a single-copy integrated transgene carrying a cpr-4 genomic fragment with a carboxyl terminal Flag tag (Pcpr-4::cpr-4::flag) restored RIBE to cpr-4(tm3718) animals (FIG. 2a), cpr-4 is required for this RIBE activity in UV-CM.

Example 4: This Example Illustrates the Secretion of CPR-4 and that CPR-4-Mediated RIBE are Induced Through a Cep-1 Dependent Mechanism The present inventors examined whether CPR-4 is secreted into the medium upon UV irradiation. CPR-4::Flag was detected in UV-CM, but not in UV-Ctrl, from Pcpr-4::cpr-4::flag animals (FIG. 1f). Immunodepletion of CPR-4::Flag from UV-CM of Pcpr-4::cpr-4::flag; cpr-4(tm3718) animals abolished its RIBE activity (FIG. 6g, h), confirming that secreted CPR-4 is the RIBE factor in UV-CM. Because UV-CM from cep-1(gk138) animals lost the RIBE activity (FIG. 2a) and UV-CM from cep-1(gk138); Pcpr-4::cpr-4::flag animals showed greatly reduced secretion of CPR-4::Flag (FIG. 7c), the CPR-4-mediated RIBE are induced through a cep-1-dependent mechanism, like some reported p53-dependent RIBE in mammals.

Example 5: This Example Illustrates Localized UV Irradiation (LUI) at One Position on an Animal Induces Bystander Effects in Other Areas of the Animal not Exposed to Radiation, and that this Effect is Dependent on Both CPR-4 and CEP-1

Figure 3:
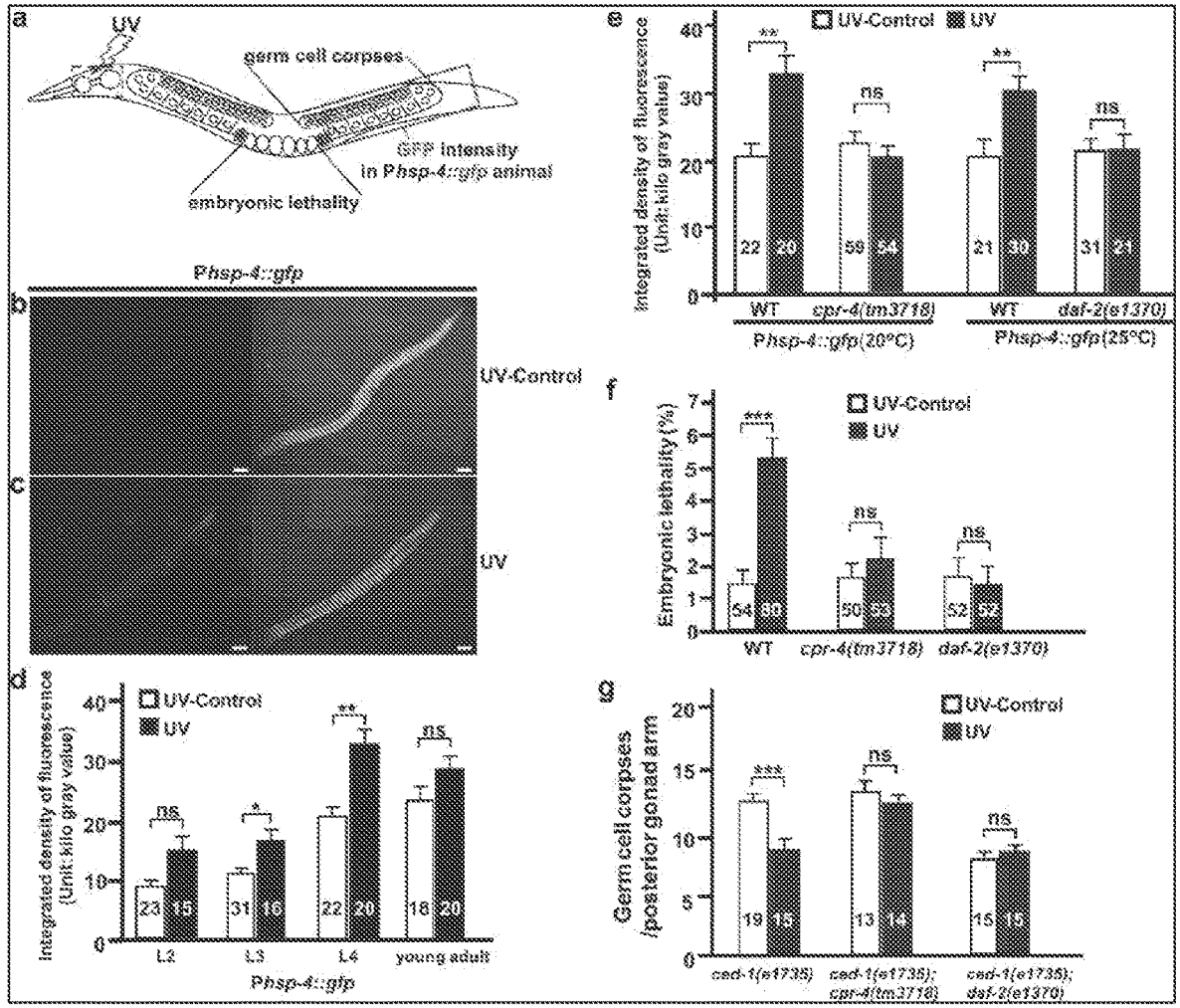
FIG. 3: CPR-4 and DAF-2 mediate RIBE in a localized UV irradiation (LUI) model. (3a). Schematic presentation of an intra-animal model to assay RIBE. The pharyngeal area of the animal was irradiated and RIBE were analyzed in three unexposed areas as indicated. (3b-c). Representative images (at least 20) of Phsp-4::gfp animals with or without LUI. Animal tails to the upper right. Scale bars, 50 μm. (3d). Assays of the Phsp-4::gfp response to LUI at different developmental stages. (3e-g). The indicated strains were analyzed for the Phsp-4::gfp response (e), F1 embryonic lethality (f), and germ cell corpses in posterior gonads (g) 24 hours post LUI. Some experiments in e and all in f were done at 25° C. Data are mean±s.e.m. The numbers of animals (d, e), plates with embryos (f), or gonad arms (g) scored are indicated inside the bars. *P<0.05, P<0.01, *P<0.001, "ns", non-significant, two-sided, unpaired t test (d-g).
Figure 10:
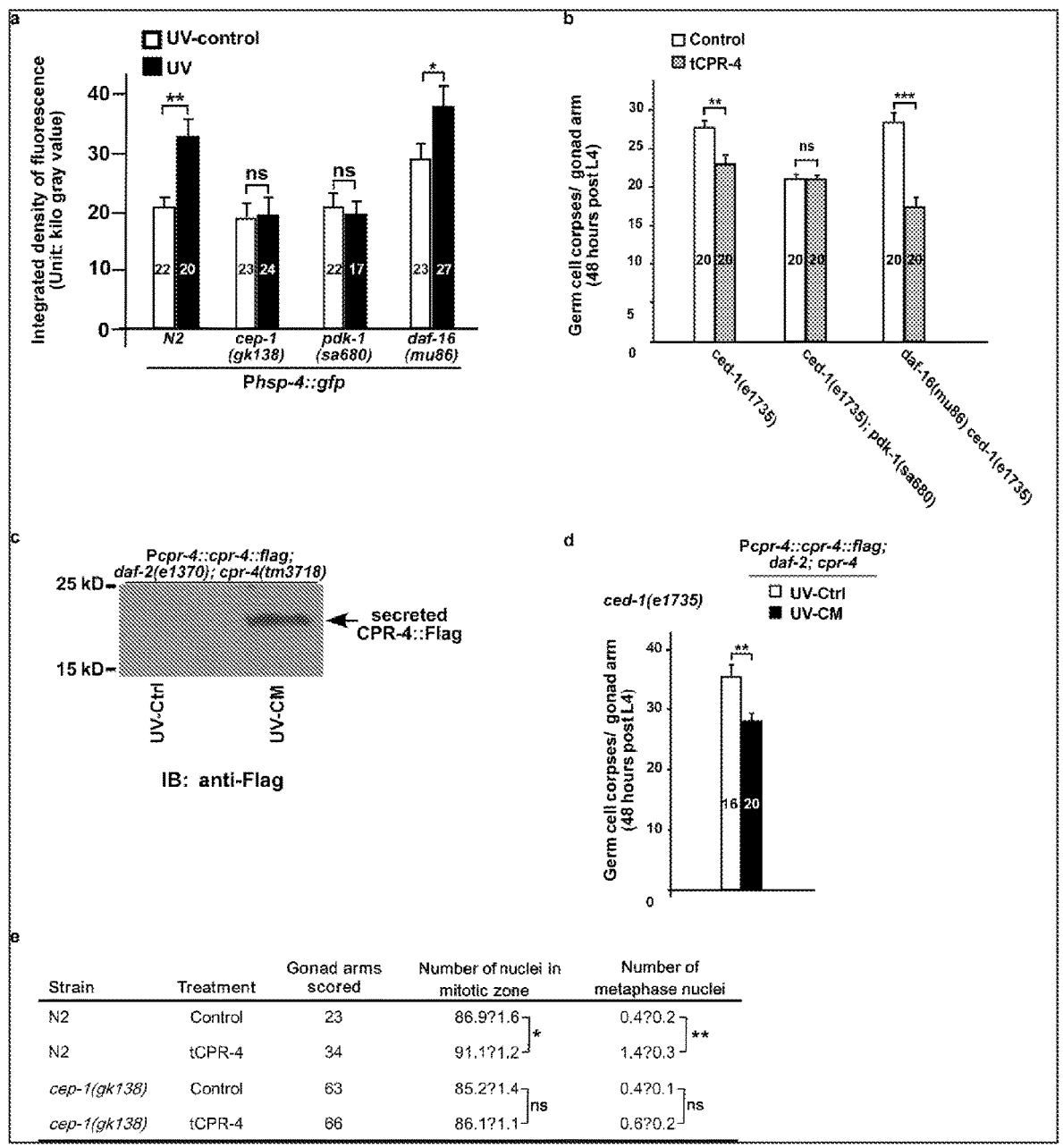
FIG. 10: Analysis of the roles of additional genes in mediating RIBE. (10a). Localized UV irradiation assays. Animals of the indicated genotype were analyzed for the bystander Phsp-4::gfp response 24 hours post localized irradiation at the head region as described in FIG. 3. Data are mean t s.e.m. The numbers of animals scored are indicated inside the bars. (10b). Germ cell corpse assays after tCPR-4 treatment. 2.8 µM recombinant tCPR-4 protein or buffer control was used to treat L4 larvae of the indicated genotype as described in FIG. 4a. Data are mean t s.e.m. The numbers of gonad arms scored are indicated inside the bars. (10c). Immunoblotting analysis of secreted CPR-4::Flag in UV-CM and UV-Ctrl from Pcpr-4::cpr-4::flag; daf-2(e1730); cpr-4(tm3718) animals was done as in FIG. 1f. (10d). Germ cell corpse assays. ced-1(e1735) L4 larvae were treated with UV-CM and UV-control (0.1 µg/µL) prepared from c. Data are mean±s.e.m. The numbers of gonad arms scored are indicated inside the bars. (10e). Germ cell proliferation assays. N2 and cep-1(gk138) L4 larvae were treated in S-Medium containing 2.8 µM of recombinant tCPR-4 or buffer control for 48 hours. The numbers of nuclei and metaphase nuclei in the mitotic zone of the germline were scored. Data are mean±s.e.m. In a, b, d, e, *P<0.05, P<0.01, *P<0.001, "ns", non-significant, two-sided, unpaired t test.

As noted above, RIBE often refer to intra-animal bystander effects. The present inventors tested if localized UV irradiation (LUI) at the head of an animal might induce bystander effects in other areas of the animal not exposed to radiation (FIG. 3a). Using a stress-response reporter, Phsp-4::gfp (zcls4), that also reacts to radiation, the present inventors observed increased GFP expression in multiple unexposed regions of LUI-treated zcls4 animals 24 hours post radiation, including strong GFP expression in the posterior region (FIG. 3b, c). This bystander response was strongest in L4 larvae (FIG. 3d), but lost in cpr-4(tm3718) and cep-1(gk138) mutants (FIG. 3e; FIG. 10a), indicating that both cpr-4 and cep-1 are required for intra-animal RIBE. LUI also led to increased embryonic lethality in unexposed progeny (FIG. 3a, f) and reduced germ cell death in nonirradiated posterior gonads in a cpr-4-dependent manner (FIG. 3a, g), indicating that LUI-induced intra-animal RIBE are similar to inter-animal RIBE induced by UV-CM and that CPR-4 is a bona fide RIBE factor.

Example 6: This Example Illustrates the Identification of a Cathepsin B-Like Protease Activity in CPR-4 and its Participation in Mediating RIBE Activities The present inventors have observed that CPR-4 and cathepsin B are highly conserved and have identical catalytic residues (FIG. 9b), including the active-site Cysteine and a Histidine residue acting as a general base16. Using a cathepsin B-specific fluorogenic substrate, z-Arg-Arg-AMC, the present inventors detected a cathepsin B-like protease activity in UV-CM, but not in UV-Ctrl, from N2 animals (FIG. 2b). This activity was absent in UV-CM from cpr-4(tm3718) animals, greatly reduced in UV-CM from cep-1(gk138) animals, but restored in Pcpr-4::cpr-4::flag; cpr-4(tm3718) animals, confirming that CPR-4 confers this cathepsin B-like activity in UV-CM through a cep-1-dependent mechanism.

The present inventors further tested to see if recombinant CPR-4 recapitulated the RIBE activity. A truncated CPR-4 lacking its signal peptide (residues 1-15), tCPR-4, exhibited a similar protease activity to that of recombinant human cathepsin B (rhCTSB)(FIG. 7d). Mutations altering the conserved catalytic residues, C109A and H281A, abolished the protease activity of tCPR-4 (FIG. 2c), whereas a mutation (N301A) changing a non-catalytic residue did not affect tCPR-4 protease activity. Like UV-CM from N2 animals, tCPR-4, tCPR-4(N301A), and rhCTSB reduced germ cell corpses (FIG. 2d; FIG. 7e) and increased embryonic lethality (FIG. 5c), whereas tCPR-4(H281A) and tCPR-4(C109A) failed to do so, indicating that the CPR-4 protease activity is critical for its RIBE activities.

Example 7: This Example Illustrates that CPR-4 is a Shared RIBE Factor Induced by a Different Radiation Source The present inventors tested conditioned medium from animals irradiated by a different radiation source, ionizing radiation (IR-CM), and its sham-irradiated control (IR-Ctrl). IR-CM from N2 or Pcpr-4::cpr-4::flag; cpr-4(tm3718) animals reduced germ cell corpses in ced-1(e1735) animals, whereas IR-CM from cpr-4(tm3718) or cep-1(gk138) animals had no such activity (FIG. 2e). Likewise, IR-CM, but not IR-Ctrl, from N2 animals caused increased embryonic lethality (FIG. 4b) and contained a cathepsin B-like activity that was lost in IR-CM from cpr-4(tm3718) or cep-1(gk138) animals, but restored in Pcpr-4::cpr-4::flag; cpr-4(tm3718) animals (FIG. 2f). Moreover, secreted CPR-4::Flag was detected in IR-CM, but not in IR-Ctrl, from Pcpr-4::cpr-4::flag animals (FIG. 2g). Therefore, CPR-4 is a shared RIBE factor induced by different radiation sources.

Using quantitative RT-PCR analysis, the present inventors found that the transcription of the cpr-4 gene in N2 animals was elevated by approximately 1.6 fold after UV or IR irradiation, compared with sham-irradiated controls (FIG. 2h). By contrast, cpr-4 transcription in cep-1(gk138) animals was not altered by either radiation. These results indicate that ionizing and non-ionizing radiation increases cpr-4 transcription through a CEP-1-dependent mechanism, leading to synthesis of more CPR-4 proteins and enhanced secretion of CPR-4.

Figure 11:
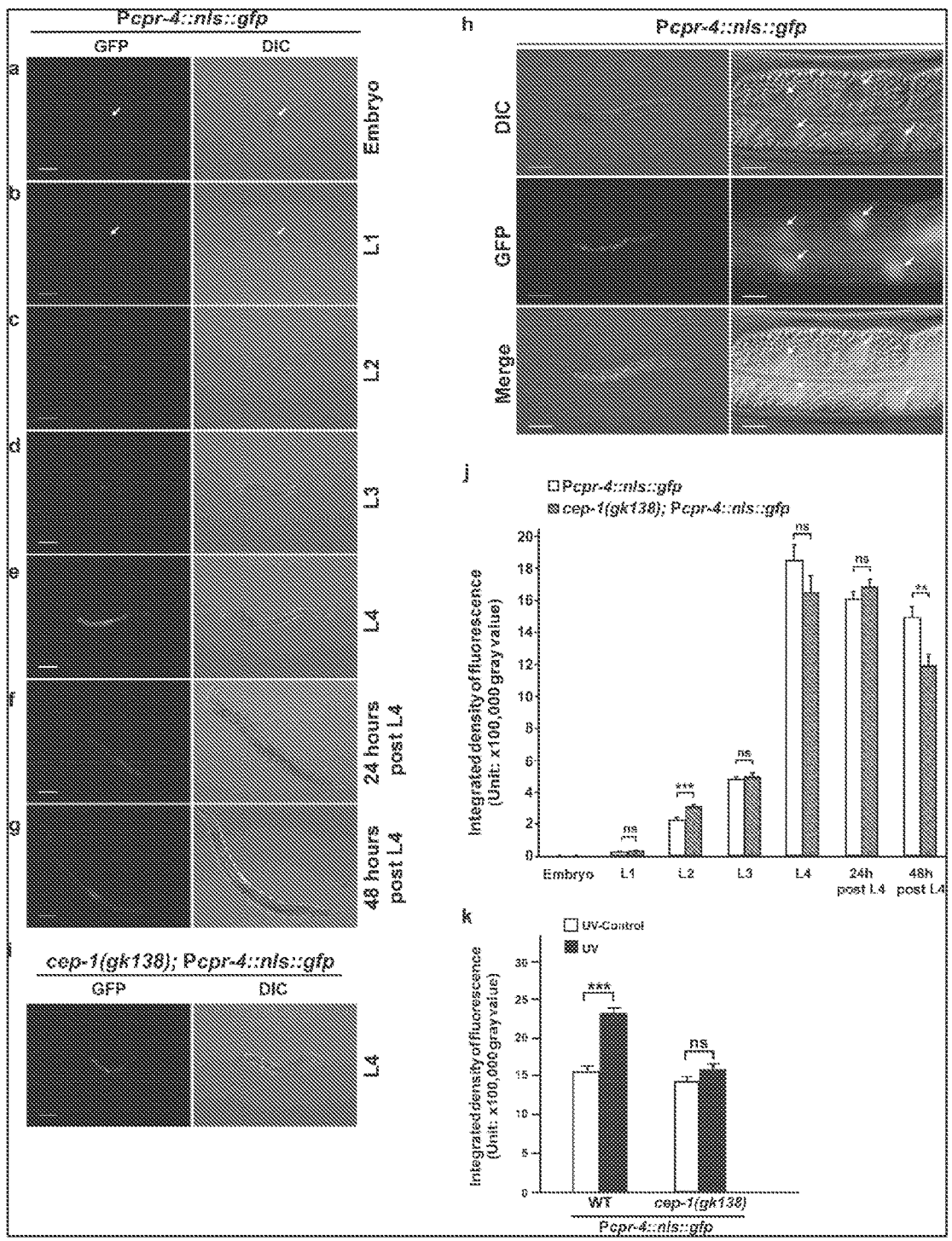
FIG. 11: The expression patterns of cpr-4 in C. elegans. (11a-g, and 7i). Representative GFP and DIC images (at least 15 each) of N2 animals (a-g) or cep-1(gk138) animals (i) carrying a single-copy integration of Pcpr-4::nls::gfp at the indicated developmental stages. Arrows point to the embryo and the L1 larva that showed no or very dim GFP (a, b). Scale bar, 100 µm. (11h). Representative DIC, GFP, and DIC/GFP merged images (at least 15) of a L4 larva carrying the same Pcpr-4::nls::gfp transgene (left column) and corresponding 10-fold magnified images showing GFP expression in intestinal cells (right column). GFP was seen mostly in the nuclei (indicated by arrows). Scale bars, 100 µm (left) and 10 µm (right), respectively. (11j). The intensity of GFP fluorescence in Pcpr-4::nls::gfp and cep-1(gk138); Pcpr-4::nls::gfp animals at different developmental stages was quantified using the Image J software. Data are mean±s.e.m. n=28, 28, 24, 31, 30, 33, 52, 52, 19, 28, 52, 52, 24, and 25 animals scored, from the left bar to the right bar, respectively. The significance of difference between two different strains at the same developmental stage was determined by two-sided, unpaired t test. P<0.01, *P<0.001, "ns", non-significant. (ilk). Quantification of GFP intensity in N2 and cep-1(gk138) animals carrying the same single-copy Pcpr-4::nls::gfp transgene irradiated by UV or sham-irradiated using Image J. Data are mean t s.e.m. n=38, 37, 32, and 30 animals scored, from the left bar to the right bar, respectively. The significance of difference between different conditions was determined by two-sided, unpaired t test. ***P<0.001, "ns", non-significant.

Example 8: This Example Illustrates that CPR-4 is Expressed Through a Cep-1 Dependent Mechanism Using a single-copy insertion transgene carrying a cpr-4 transcriptional fusion with green fluorescent protein (GFP) and a nuclear localization signal (Pcpr-4::nls::gfp), the present inventors examined when and where cpr-4 is expressed. In N2 animals, NLS::GFP expression was not detected in embryos, was observed in the intestine of early stage larvae (L1 to L3), peaked at the L4 larval stage, and declined when animals entered the adulthood (FIG. 7a-h, j). Similar spatiotemporal NLS::GFP expression patterns were observed in cep-1(gk138); Pcpr-4::nls::gfp animals (FIG. 11i, j). When irradiated with UV, N2 animals, but not cep-1(gk138) animals carrying Pcpr-4::nls::gfp, showed elevated NLS::GFP expression (FIG. 11k), confirming that radiation induces increased cpr-4 transcription through a cep-1-dependent mechanism.

Figure 12:
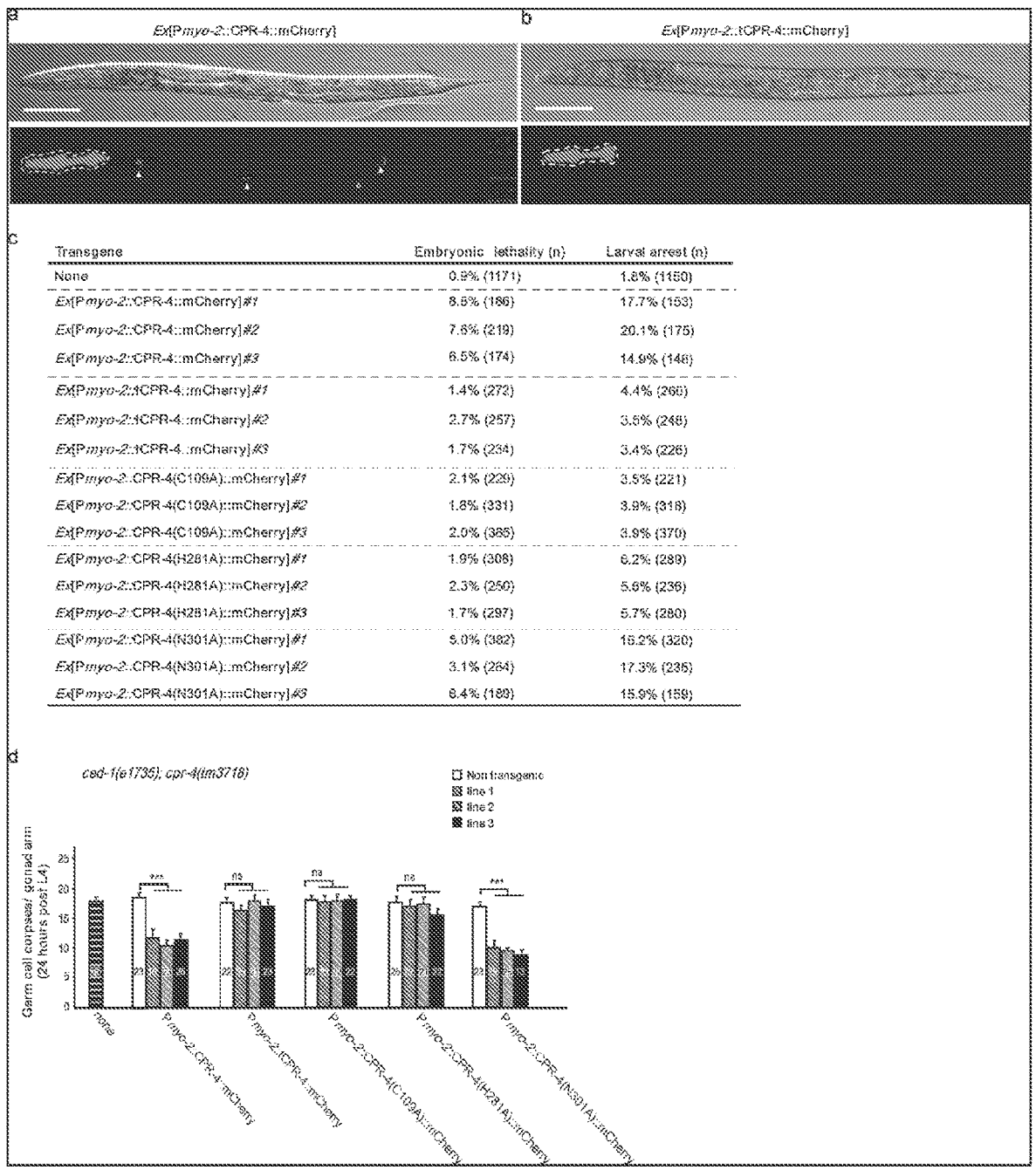
FIG. 12: Pharyngeal expression of CPR-4 results in embryonic lethality, larval arrest, and reduced germ cell death. (12a-b). Representative DIC and mCherry images (at least 10) of adult animals with pharyngeal expression of CPR-4::mCherry (a) and tCPR-4::mCherry (b). White dash lines highlight the edge of the pharynx. Arrowheads indicate cells, including coelomocytes, that had taken up CPR-4::mCherry (a), which was made in and secreted from the pharynx and transported to other parts of the animal, probably through the pseudocoelom, a fluid-filled body cavity. The enlarged images of two pairs of posterior cells with weak fluorescence (indicated by color arrowheads) are shown in dash boxes with corresponding colors. Scale bars, 100 μm. (12c). The percentages of embryonic lethality and larval arrest were scored in embryos or larvae carrying Pmyo-2::CPR-4::mCherry (wild-type or mutant) or Pmyo-2::tCPR-4::mCherry transgenes. Three independent transgenic lines were scored for each construct. The number of newly hatched transgenic L1 larvae scored and the number of transgenic embryos scored are indicated in parentheses. The increased larval arrest seen in Pmyo-2::CPR-4::mCherry transgenic animals was blocked when transgenic animals were treated with cpr-4 RNAi (Table 6), indicating that reducing cpr-4 expression prevents larval arrest. All animals carry the ced-1(e1735) and cpr-4(tm3718) mutations (a-c). (12d). Quantification of germ cell corpses in transgenic animals. L4 ced-1(e1735); cpr-4(tm3718) animals carrying the indicated transgenes were grown on regular NGM plates for 24 hours before examination. Data are mean±s.e.m. The numbers of gonad arms scored are indicated inside the bars. The significance of difference between transgenic and non-transgenic animals was determined by one-way analysis of variance (ANOVA). ***P<0.001, "ns", non-significant.

Example 9: This Example Illustrates the Long-Range Signaling Effects of Secreted CPR-4 In Vivo To investigate the effects of secreted CPR-4 in vivo, the present inventors generated transgenic Pmyo-2::CPR-4:: mCherry animals expressing CPR-4::mCherry specifically in C. elegans pharynx under the control of the myo-2 gene promoter (FIG. 12a). As expected of a secreted protein, CPR-4::mCherry was made in and secreted from the pharynx and taken up by cells in the whole body, including the phagocytic coelomocytes (arrowheads, FIG. 12a). Removal of the CPR-4 signal peptide blocked tCPR-4::mCherry secretion from the pharynx in transgenic animals (FIG. 12b). Like UV-CM, IR-CM or LUI treatment, pharyngeal expression of CPR-4::mCherry increased embryonic lethality, decreased germ cell death, and in addition, caused substantial larval arrest (FIG. 12c, d), which were not seen or greatly attenuated in animals expressing tCPR-4::mCherry or catalytically inactive CPR-4::mCherry proteins. These results from ectopic expression of CPR-4 provide further evidence to support a long-range signaling role of CPR-4 as a RIBE factor.

Figure 4:
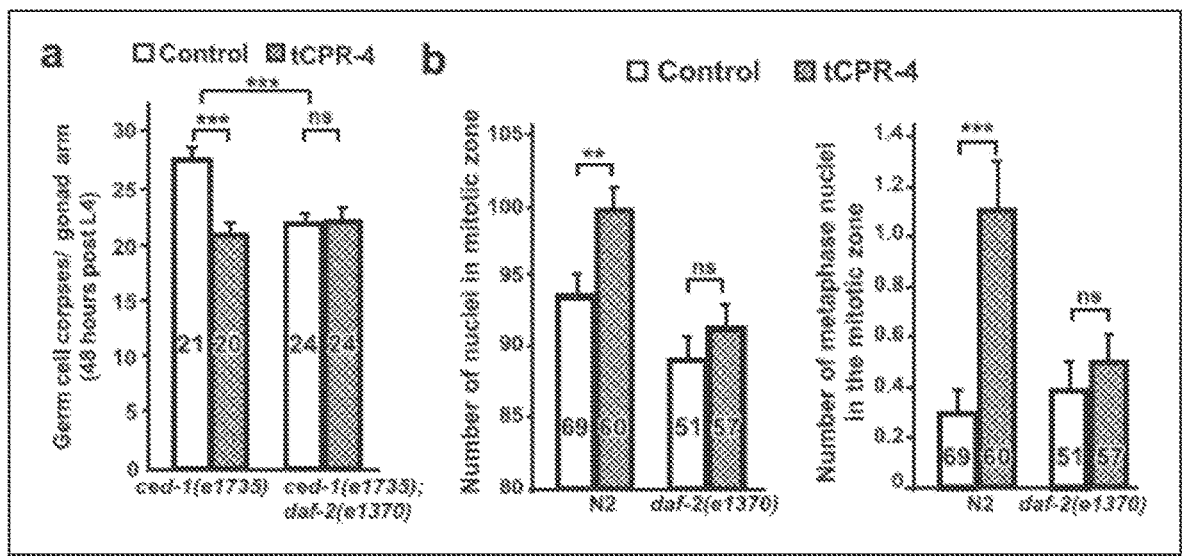
FIG. 4: CPR-4 acts through DAF-2 to exert RIBE. (4a-b). L4 larvae of the indicated strains were treated with 2.8 μM of tCPR-4 or buffer control for 48 hours. Data are mean±s.e.m. The numbers of gonad arms scored are indicated inside the bars. P<0.01, *P<0.001, "ns", non-significant, two-sided, unpaired t test.

Example 10: This Example Illustrates the Various RIBE Effects Mediated by CPR-4 in Non-Irradiated Cells or Animals Given the various RIBE effects mediated by CPR-4, the present inventors investigated how CPR-4 influences unexposed cells or animals through examining genes that affect multiple cellular processes. The daf2 gene, which encodes a C. elegans ortholog of the human insulin/IGF receptor and regulates multiple signaling pathways, was examined, as reduced daf2 activity increases life span and stress resistance and decreases germ, muscle and neuronal cell death induced by genotoxic and hypoxic stresses. Similarly, reduced daf2 function by a temperature-sensitive mutation (e1370) decreased physiological germ cell death (FIG. 4a). Interestingly, purified tCPR-4 did not further reduce germ cell death in the ced-1(e1735); daf2(e1370) mutant (FIG. 4a), suggesting that tCPR-4 and daf-2 act in the same pathway to affect germ cell death. Moreover, tCPR-4 did not reduce germ cell death in ced-1(e1735); pdk-1(sa680) animals, which are defective in the PDK-1 kinase, a key downstream signaling component of DAF-2, but could do so in daf-16(mu86) ced-1(e1735) animals, which lack DAF-16, one of the major transcription factors acting downstream of DAF-2 (FIG. 10b). The present inventors observed similar results using the LUI assays wherein inactivation of daf2 and pdk-1, but not daf-16, prevented increased GFP expression from Phsp-4::gfp in the posterior unexposed regions (FIG. 3e and FIG. 10a) and loss of daf-2 blocked increased embryonic lethality and reduced germ cell death in unexposed tissues (FIG. 3f, g). Because loss of daf-2 did not seem to affect the secretion of CPR-4 into UV-CM or the apoptosis-inhibitory activity of UV-CM (FIG. 10c, d), these results support a model wherein the secreted CPR-4 acts through the DAF-2 insulin/IGF receptor and the PDK-1 kinase, but not the DAF-16 transcription factor, to exert RIBE in unexposed cells.

Example 11: This Example Illustrates that CPR-4 (tCPR-4) Promotes Germ Cell Proliferation Through DAF-2 and CEP-1

Because daf-2 also affects germ cell proliferation, the present inventors examined if tCPR-4 treatment alters germ cell proliferation by scoring the number of nuclei in the germline mitotic region. tCPR-4 treatment of N2 animals resulted in more germ cell nuclei and more metaphase nuclei in the mitotic zone (FIG. 4b), suggesting a stimulating effect. Reduced daf-2 activity or loss of cep-1 blocked increased germ cell proliferation induced by tCPR-4 (FIG. 4b and FIG. 10e), indicating that tCPR-4 promotes germ cell proliferation through DAF-2 and CEP-1.

Figure 2:
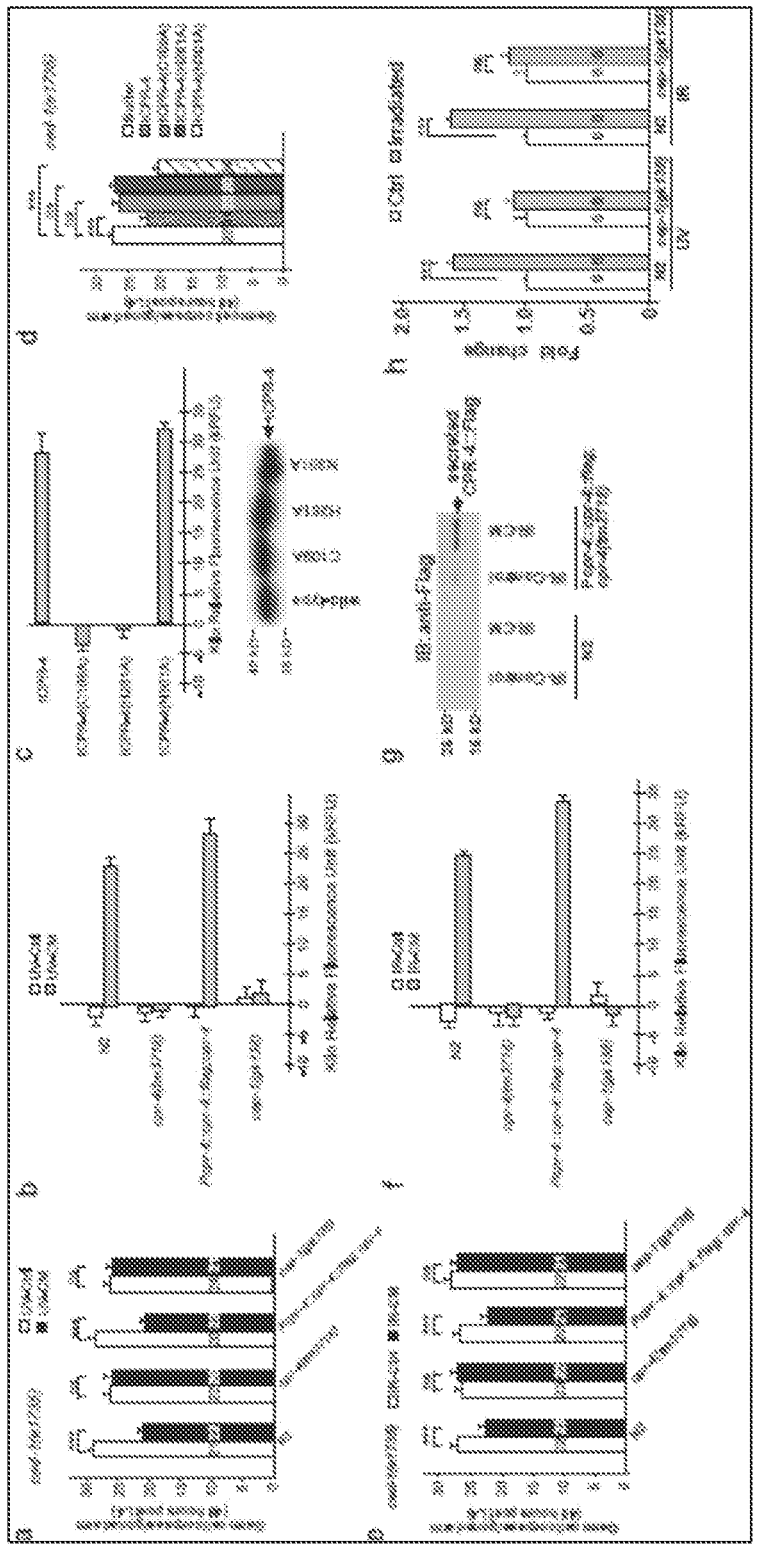
FIG. 2: Identification of CPR-4 as a RIBE factor. (2a, 2d-e). Conditioned medium (0.1 μg/μL) from the indicated strains (a, e) or 2.8 μM of recombinant tCPR-4 proteins (d) were used to treat ced-1(e1735) animals as in FIG. 1b. (2b-c, 2f). Protease activity of conditioned medium (0.1 μg/μL) from the indicated strains (b, f) or 2.8 μM tCPR-4 proteins (c). Immunoblotting image of tCPR-4 is below c. (2g). CPR-4::Flag was secreted into IR-CM from Pcpr-4::cpr-4::flag animals. IR-CM and IR-Ctrl (1 μg/μL) resolved on SDS PAGE were detected by immunoblotting. (2h). Relative cpr-4 mRNA levels (fold change) in the indicated strains were determined by quantitative RT-PCR, compared to those of sham-irradiated samples (Ctrl). Data are mean±s.e.m. (a-f, h). The numbers of gonad arms scored are indicated inside the bars (a, d, e) and n=6 in each group for other assays (b, c, f, h); ***P<0.001, "ns", non-significant, two-sided, unpaired t test (a, d, e, h).
Figure 13:
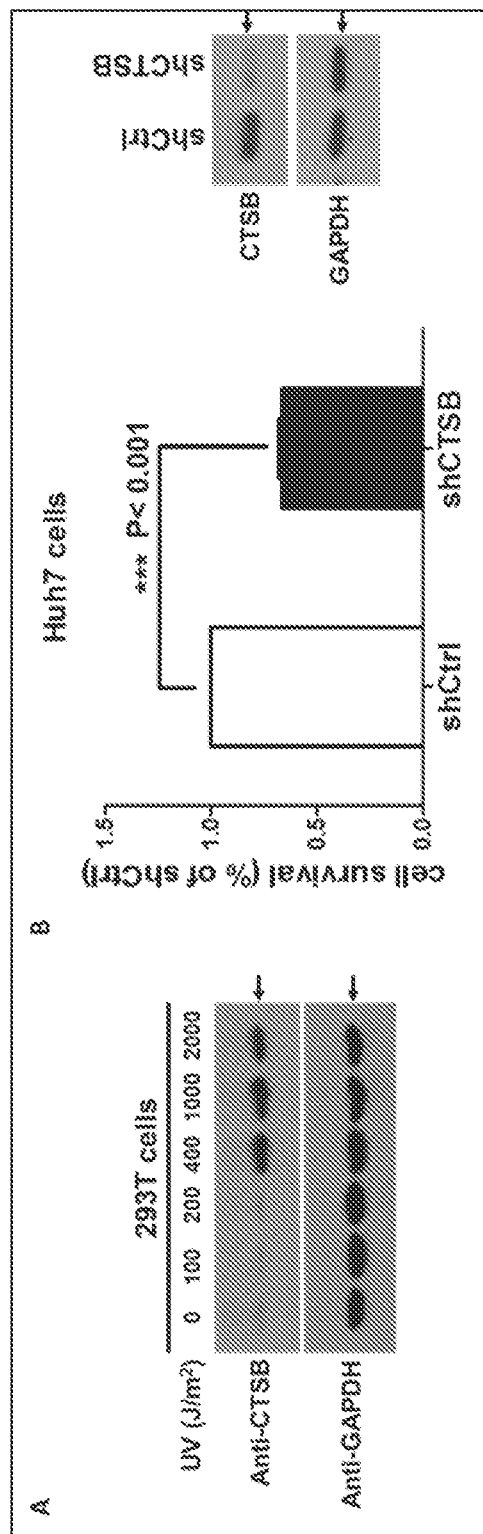
FIG. 13: Cathepsin B (CTSB) is involved in UV-induced bystander effects in human cells. (13a). Cathepsin B (CTSB) expression is unregulated in response to UV irradiation. 293T cells were irradiated with UV at the indicated dosages. Cells were then collected 24 hours later and subjected to immunoblotting analysis using anti-CTSB and anti-GAPDH (loading control) antibodies, respectively. (13b). UV conditioned medium (UV-CM) collected from irradiated 293T cells displays a stronger pro-survival activity than that from 293T cells with reduced Cathepsin B (CTSB) expression. UV-CM collected from 293T cells expressing control short hairpin RNA (shRNA) or Cathepsin B (CTSB)shRNA was used to cultured unexposed Huh7 cells. The percentage of Huh7 survival was measured using SRB assays. The efficiency of Cathepsin B (CTSB) knockdown was shown by immunoblotting at the right.

Example 12: This Example Illustrates that Human Cathepsin B (CTSB) is Involved in RIBE Effects in Human Cells To investigate whether human cathepsin B (CTSB) cysteine protease is also involved in radiation-induced bystander effects, the present inventors first examined if the expression of CTSB is upregulated in response to UV irradiation as observed in C. elegans. As shown in FIG. 13A, the expression of CTSB is upregulated in response to UV irradiation in a dosage-dependent manner, reaching maximal response at 400 J/m2. The present inventors then generated CTSB short hairpin RNA (shCTSB) knockdown 293T cells and irradiated these cells and control shRNA (shCtrl) 293T cells with UV at 400 J/m2. UV conditioned medium (UV-CM) was then collected from the irradiated cells (see Methods) and used to culture unexposed Huh7 cells. The present inventors found that UV-CM from shCtrl 293T cells displays a significantly stronger activity in promoting cell survival than UV-CM collected from shCTSB 293T cells, indicating that loss of CTSB expression reduces radiation-induced bystander effect in promoting cell survival. The present inventors observed similar results with UV-CM collected from shCtrl Huh7 cells and shCTSB Huh7 cells (FIG. 2). These results together that that the cathepsin B cysteine protease is also involved in UV-induced bystander effects in human cells.

In this embodiment, 293T cells were transfected with PLKO.1-Ctrl (shCtrl) and PLKO.1-CTSB (shCTSB) plasmids, respectively, for 48 hours. Cells were washed and placed in fresh medium and exposed to UV radiation (400 J/m$^2$). The irradiated cells were cultured for another 48 hours. The supernatant, the UV conditioned medium, was collected and used to culture unexposed Huh7 cells for 48 hours. Sulforhodamine B (SRB) assays were performed to measure the percentage of Huh7 cell survival. In addition, Huh7 cells were transfected with PLKO.1-Ctrl (shCtrl) and PLKO.1-CTSB (shCTSB) plasmids for 48 hours. Cells were washed and placed in fresh medium and exposed to UV radiation (400 J/m$^2$). The irradiated cells were cultured for another 48 hours. The supernatant, the UV conditioned medium, was collected and used to culture unexposed Huh7 cells for 48 hours. Sulforhodamine B (SRB) assays were performed to measure the percentage of Huh7 cell survival.

Example 13: This Example Demonstrates Screens for Compounds that Inhibit the Cathepsin B Protease Activity In Vitro To identify compounds that can inhibit the activity of the cysteine protease cathepsin B (CTSB), a critical mediator of radiation-induced bystander effects (RIBE), the present inventors screened a collection of bioactive small molecules that are known inhibitors of cysteine proteases or have potential anti-cancer activities (See Table 1 below). These include three cysteine protease inhibitors, E64 [N—[N-(L-3-Trans-carboxirane-2-carbonyl)-L-leucyl]-agmatine], CA074 [N-(1-3-trans-propylcarbamoyloxirane-2-carbonyl)-1-isoleucyl-1-proline], a selective inhibitor of CTSB (1), and CA074 methyl ester (CA074Me), a membrane-permeant inhibitor for intracellular CTSB. The present inventors also tested a short-chain polypeptide, NH$_2$-Arg-Leu-Ala-COOH (RLA), a selenium chelate of this polypeptide, NH$_2$-Arg-Leu-Ala-COOH—Se, and some anti-cancer compounds and vitamins that are reported to inhibit the proliferation of cancer cells and exhibit low toxicity to mammalian cells.

From a collection of 18 bioactive small molecules, the present inventors identified 11 compounds that show CTSB inhibitory activities. (See generally FIGS. 22-23) Three cysteine protease inhibitors, CA074Me, CA074 and E64, demonstrated the best inhibitory effects on the CTSB protease (See Table 2 below). The short chain polypeptide (RLA) and its selenium chelate inhibit more than 86% of the CTSB protease activity. Several flavonoids, apigenin [5,7-Dihydroxy-2-(4-hydroxyphenyl)-4H-1-benzopyran-4-one], quercetin [2-(3,4-dihydroxyphenyl)-3,5,7-trihydroxy-4H-chromen-4-one], isoquercitrin [2-(3,4-Dihydroxyphenyl)-5,7-dihydroxy-3-[(2S,3R,4S,5S,6R)-3,4,5-trihydroxy-6-(hydroxymethyl)oxan-2-yl]oxychromen-4-one], and baicalein (5,6,7-Trihydroxy-2-phenyl-chromen-4-one), can also achieve 65-85% inhibition. Tannic acid, a polyphenol but not a flavonoid, shows 69.29% inhibition. As also shown in Table 2, interestingly, folic acid, also known as vitamin B9, turns out to be a CTSB activator and can enhance the activity of the CTSB protease by more than 4 folds.

As shown in Table 3, the present inventors determined the half maximal inhibitory concentration (IC50) of some of these compounds. E64, CA074 and CA074Me demonstrated the best IC50 values, around or less than 20 nM. The flavonoids, quercetin and baicalein, have IC50 at 1.87 µM and 0.87 µM, respectively. The short chain polypeptide RLA has an IC50 significantly higher than other compounds. On the other hand, the half maximal effective concentration (EC50) of folic acid is 1.26 µM.

As note above, the C. elegans CTSB homologue, CPR-4, exhibits a similar protease activity and property to that of human CTSB. The present inventors assayed the activities of some of these compounds in inhibiting the CPR-4 protease activity in vitro. As shown in Table. 4, the cysteine protease inhibitor E64 has the highest inhibitory activity (89.59%) on the CPR-4 protease and the short chain polypeptide RLA inhibits 85.03% of the CPR-4 protease activity. The flavonoid quercetin exhibits 80.67% inhibition and the flavonoid baicalein shows 41.54% inhibition.

Example 14: This Example Demonstrates that Cathepsin B Inhibitors Block Radiation-Induced Bystander Effects (RIBE)

Using a localized UV irradiation (LUI) intra-animal RIBE model described above, the present inventors examined if the identified CTSB inhibitors can block RIBE or side effects induced by LUI. Several prominent RIBE effects seen in *C. elegans* are chromosomal DNA damage in unexposed germ cells in the posterior gonad, increased lethality of unexposed embryos, and elevated stress response in the unexposed posterior region of animals that undergo LUI specifically at the head region. Before subject to the LUI treatment, larval stage 2 (L2) animals were first treated with DMSO (Mock), 10 µM of CA074, CA074Me, or E64, or 250 µM of quercetin, isoquercitrin, (FIG. 19) or folic acid (FIG. 20), respectively, for 48 hours.

Figure 21:
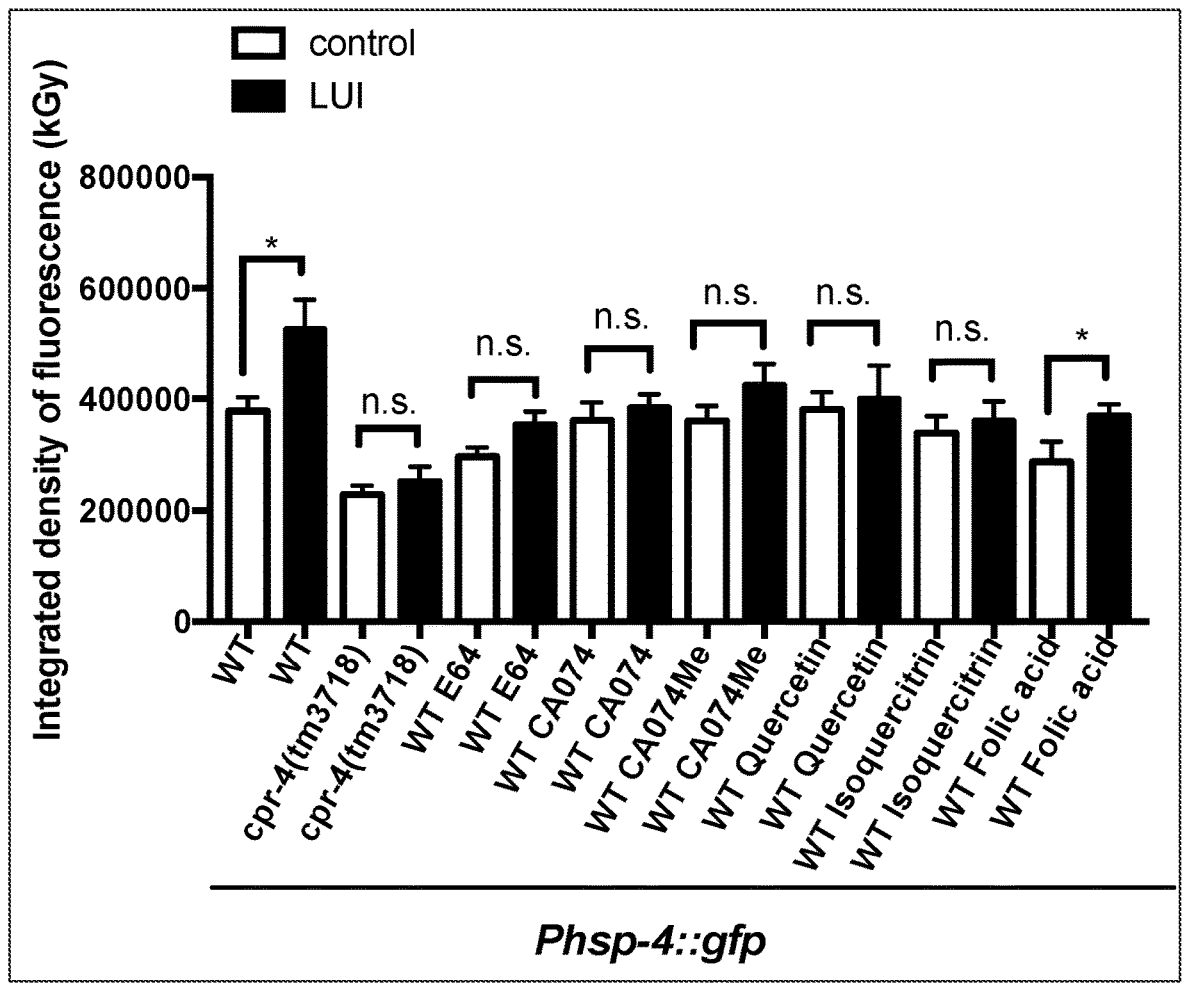
FIG. 21: Inhibition of the stress response ($P_{hsp-4}$::gfp) induced by localized UV irradiation. The stress response in the posterior region of irradiated animals was quantified by measuring the GFP fluorescent intensity from the $P_{hsp-4}$::gfp integrated transgene, a stress-response reporter. In each experiment, at least 15 animals were scored. L2 animals were treated with the drug. Data are mean±s.e.m. n.s., not significant; *P<0.05, two-sided, unpaired t-test.

Assays of the chromosomal DNA damage in unexposed germ cells in the posterior gonads of the LUI animals were carried out on animals containing a hus-1::NeoGreen knock-in. The *C. elegans* gene hus-1 is required for DNA damage-induced cell cycle arrest and apoptosis. Following DNA damage, HUS-1 has been shown to localize specifically to breaks of chromosomes and form distinct foci on the chromatin. The present inventors thus analyzed the unexposed mitotic germ cells for the number of HUS-1::NeoGreen foci in LUI animals, which serves as an indicator of chromosomal DNA damage induced by irradiation. As shown in FIG. 21, treatment with the identified compounds, except for folic acid (a CTSB activator), or genetic inactivation of the cpr-4 gene through a deletion (tm3718), potently inhibited the number of germ cells with positive HUS-1 foci, indicating that the identified compounds or inactivation of the cpr-4 gene block the side effect of chromosomal DNA damage induced by LUI.

Figure 19:
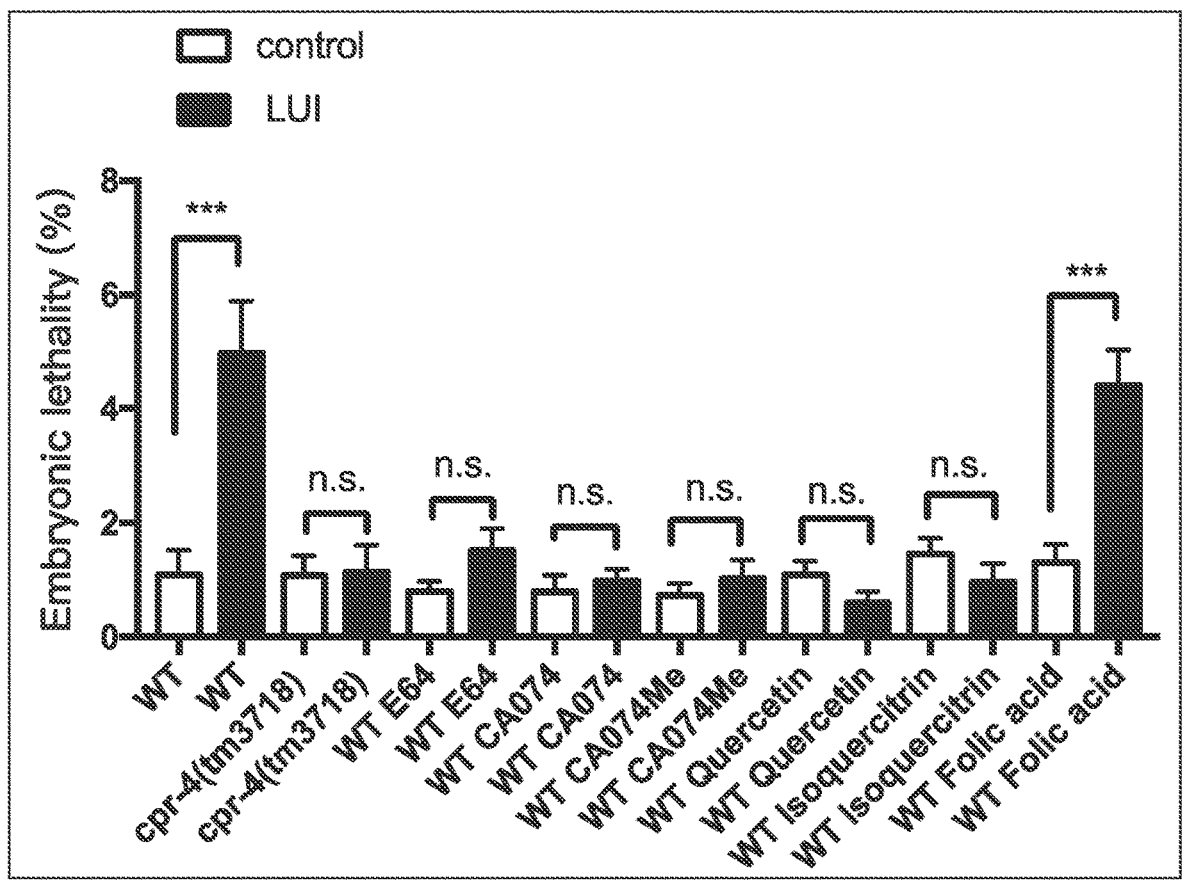
FIG. 19: Inhibition of embryonic lethality induced by localized UV irradiation. In each experiment, more than 1500 embryos were scored. L2 animals were treated with the drug. Data are mean±s.e.m. n.s. indicates not significant; ***P<0.001, two-sided, unpaired t-test.
Figure 20:
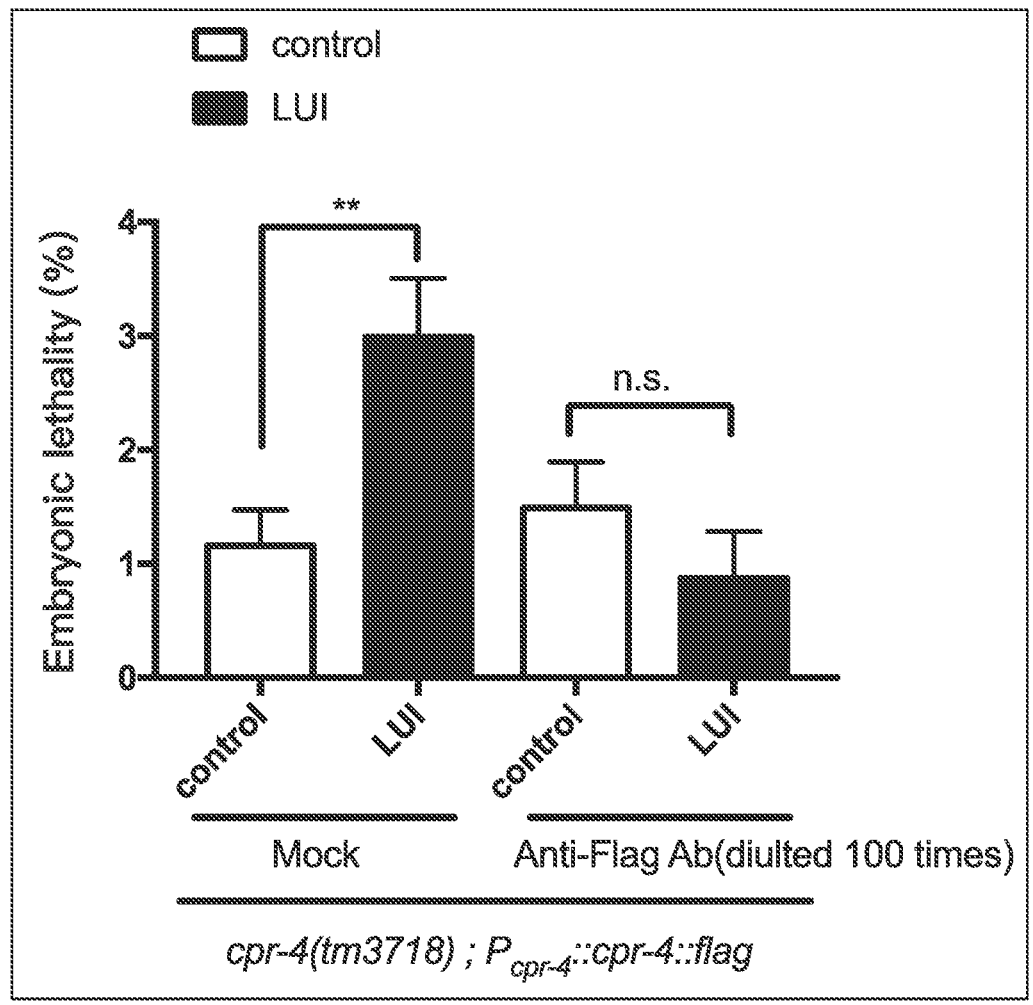
FIG. 20: Inhibition of embryonic lethality induced by localized UV irradiation using specific antibody. In each experiment, more than 700 embryos were scored. L2 animals were treated with the anti-Flag antibody targeted to the CPR-4::Flag protein. Data are mean±s.e.m. n.s., not significant; **P<0.01, two-sided, unpaired t-test.

Assays of the increased lethality of unexposed embryos in LUI animals were performed as described previously. As shown in FIG. 19, wild-type (WT) animals after the LUI treatment showed increased embryonic lethality in their unexposed progeny. However, in animals pretreated with the identified compounds (with the exception of folic acid, a CTSB activator) or in animals deficient in the cpr-4 gene, LUI did not induce increased embryonic lethality. These results indicate that the identified CTSB inhibitor compounds or genetic inactivation of the cpr-4 gene can prevent the side effect of increased embryonic lethality in *C. elegans* induced by localized irradiation. Interestingly, when cpr-4 (tm3718) animals carrying a single-copy cpr-4 transgene expressing a modified CPR-4 protein with a short peptide tag (the Flag tag) at its carboxyl terminus were pretreated with an anti-Flag antibody before the LUI treatment, the antibody, but not the mock treatment, effectively blocked the side effect of increased embryonic lethality induced by localized irradiation as shown in FIG. 20, indicating that the *C. elegans* RIBE model can also be used to screen for antibody drugs that can alleviate side effects induced by radiotherapy.

Assays of the elevated stress response in the unexposed posterior region of the LUI animals were performed in animals carrying an integrated transgene expressing a GFP reporter under the control of the promoter of the hsp-4 gene (Phsp-4::gfp), which can respond to several stress conditions, including irradiation. As shown in FIG. 21, treatment with the identified compounds, except for folic acid, or loss of the cpr-4 gene, potently inhibited the side effect of increased stress response, indicated by increased GFP fluorescent intensity, in the posterior unexposed regions of the LUI animals. These results together indicate that the identified CTSB inhibitors can block various side effects induced by irradiation in an exemplary eukaryotic organism. These studies also indicate that the combination of the in vitro drug screen and the testing of the identified compounds in the *C. elegans* RIBE model is a powerful approach to identify effective small molecule compounds or antibody drugs that can be used to alleviate or treat side effects induced by radiotherapy or other human disease.

Figure 14:
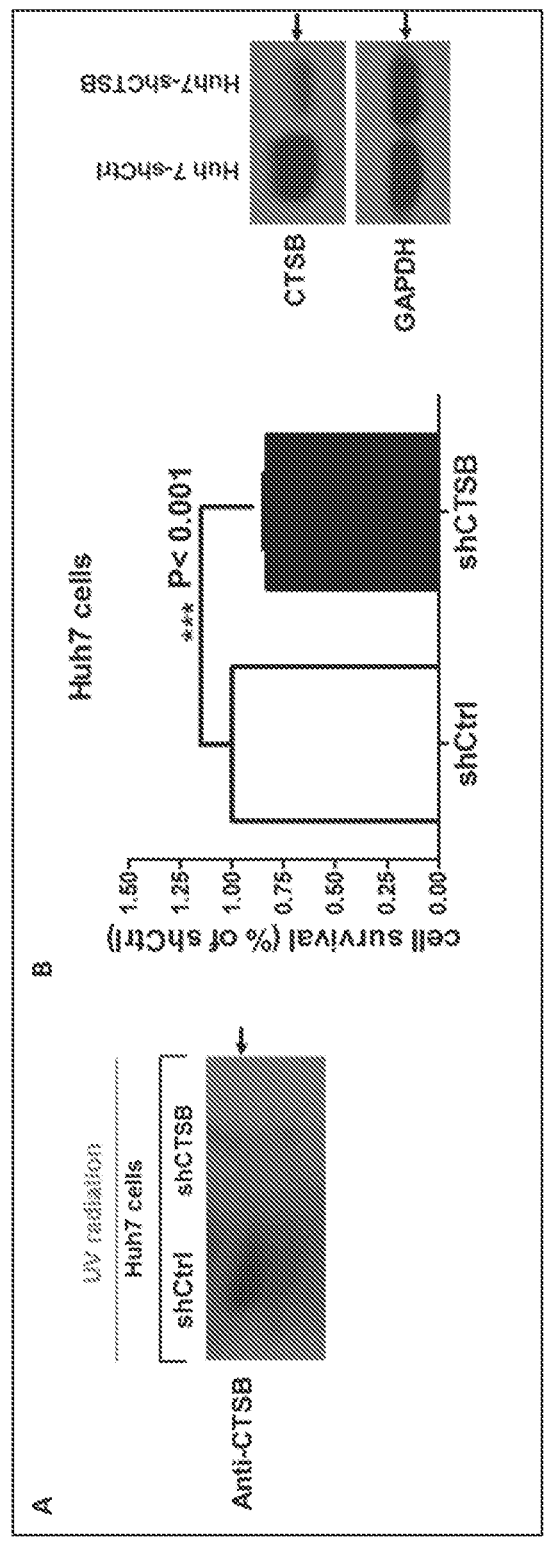
FIG. 14: Cathepsin B (CTSB) is involved in UV-induced bystander effects in human cells. (14a). Greatly reduced Cathepsin B (CTSB) secretion in UV conditioned medium (UV-CM) collected from irradiated Huh7 cells expressing Cathepsin B (CTSB)shRNA. Huh7 cells expressing the indicated shRNA were irradiated with UV (400 J/m$^2$). UV-CM was then collected 48 hours later and subjected to immunoblotting analysis using anti-CTSB antibodies. (14b). UV-CM collected from irradiated Huh7 cells similarly promotes cell survival. UV-CM collected from Huh7 cells expressing control shRNA or CTSB shRNA was used to cultured unexposed Huh7 cells. The percentage of Huh7 cell survival was measured using SRB assays (Methods). The efficiency of CTSB shRNA knockdown was shown by immunoblotting at the right.
Figure 15:
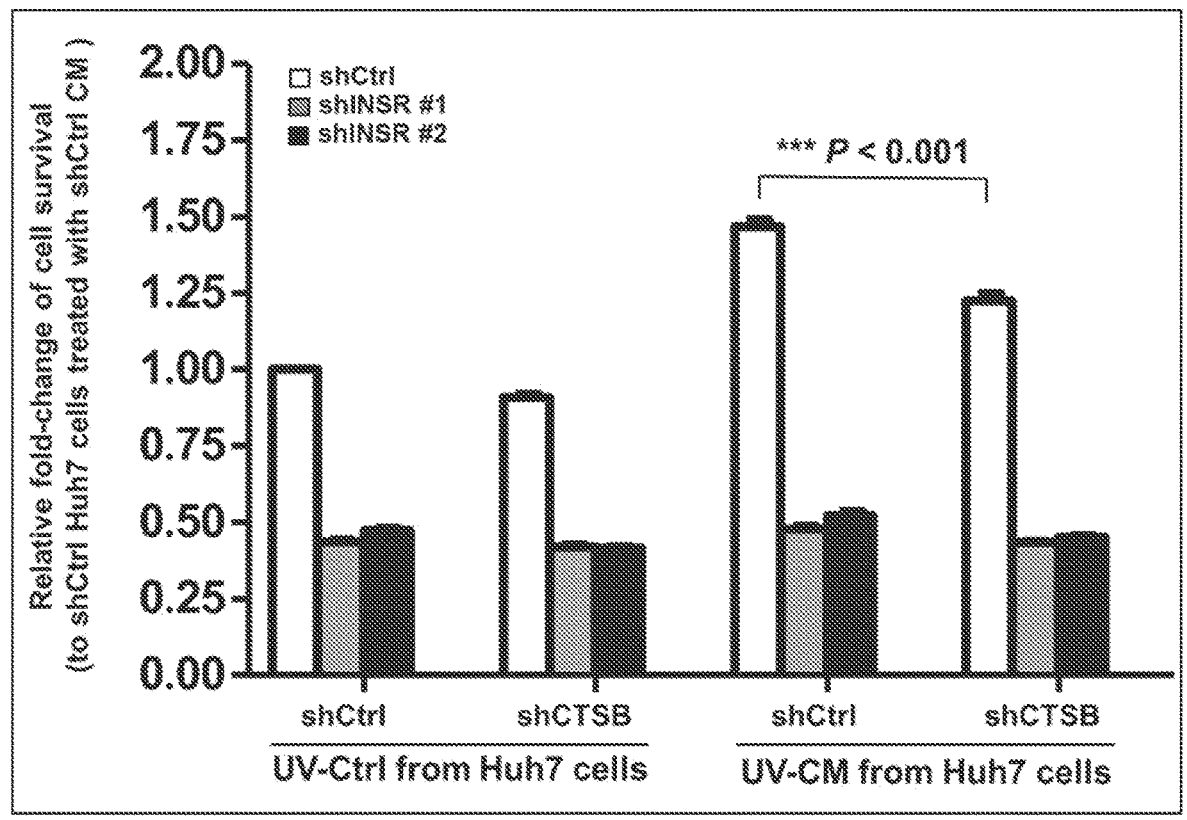
FIG. 15: Human Insulin Receptor is important for mediating CTSB-induced RIBE in human cells. Huh7 cells expressing shCtrl and shCTSB were irradiated with UV (400 J/m2). UV-CM was then collected 48 hours later and used to treat unexposed Huh7 cells expressing shCtrl or shINSR. The percentage of Huh7 cell survival was measured using SRB assays. Huh7 cells were transfected with PLKO.1-Ctrl (shCtrl) and PLKO.1-CTSB (shCTSB) plasmids for 48 hours. Cells were washed and placed in fresh medium and exposed to UV radiation (400 J/m2). The irradiated cells were cultured for another 48 hours. The supernatant, the UV conditioned medium, was collected and used to culture unexposed Huh7 cells expressing shCtrl or shINSR for 48 hours. Sulforhodamine B (SRB) assays were performed to measure the percentage of Huh7 cell survival.

Example 15: This Example Identifies that Human Insulin Receptor is Important for Mediating CTSB-Induced RIBE The involvement of human Insulin/IGF Receptor (INSR), the homologue of the *C. elegans* DAF-2 protein, in RIBE in human cells was investigated. The present inventors decreased INSR expression in human Huh7 cells using two different INSR short hairpin RNA lentiviral clones (shINSR #1 and #2) and then treated these INSR knockdown cells with conditioned medium collected from sham-irradiated Huh7 cells (UV-Ctrl) or UV-irradiated (UV-CM) Huh7 cells that expressed either shCtrl or shCTSB (see FIG. 14). INSR knockdown (shINSR #1 and #2) appeared to decrease Huh7 cell survival, which was not affected by UV-Ctrl collected from either shCtrl or shCTSB Huh7 cells. Consistent with the previous observations (FIGS. 13 and 14), UV-CM from shCtrl Huh7 cells displayed a significantly stronger activity in promoting cell survival in unexposed shCtrl Huh 7 cells than UV-CM collected from shCTSB Huh7 cells (FIG. 15), confirming that CTSB promotes cell survival. However, shINSR knockdown blocked enhanced cell survival induced by UV-CM from shCtrl Huh7 cells compared with UV-CM from shCTSB Huh7 cells (FIG. 15). These results suggest that the Insulin/IGF receptor is also important for mediating CTSB-induced RIBE in human cells and that the RIBE signaling pathways are conserved between *C. elegans* and humans.

Figure 16:
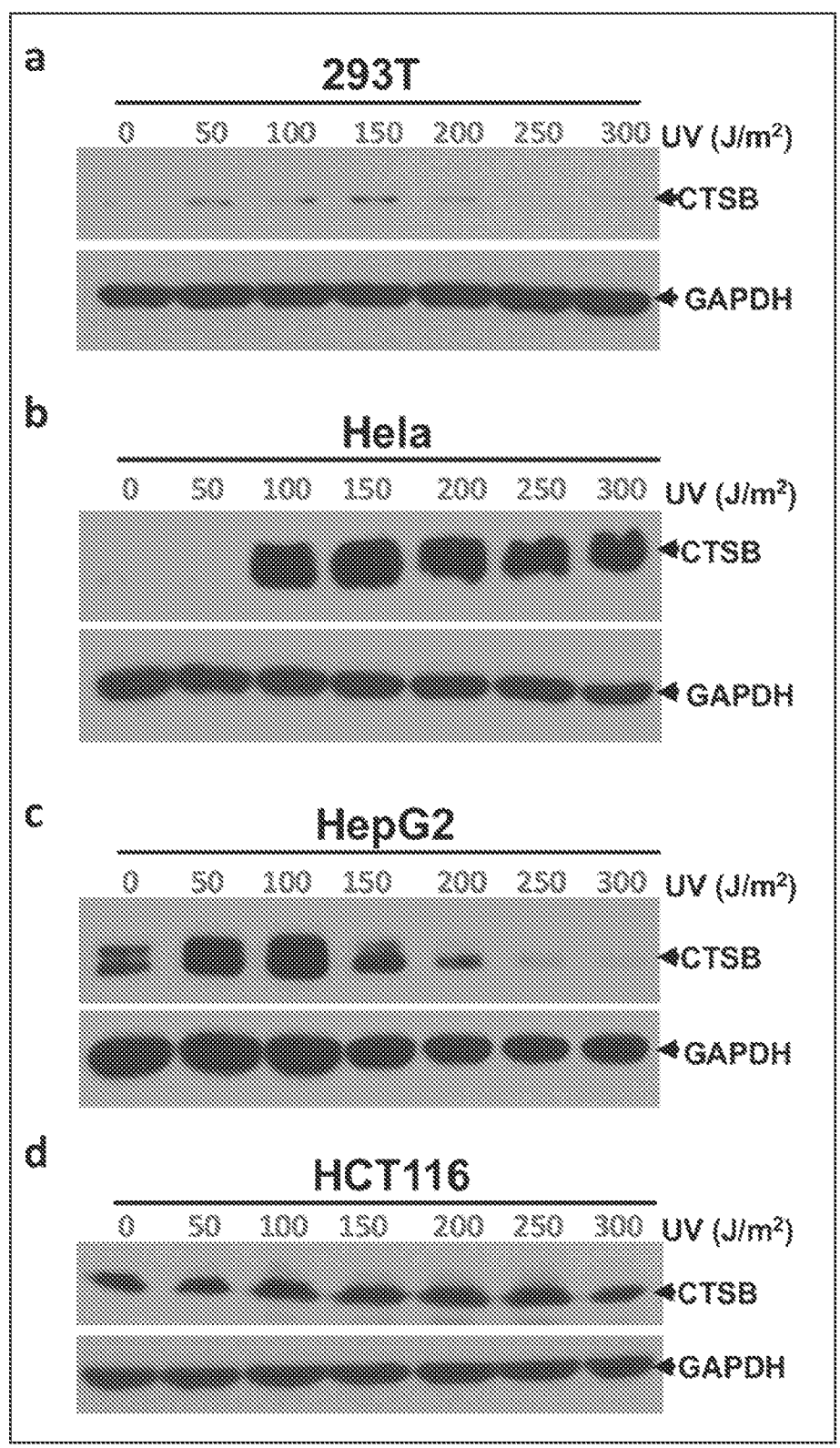
FIG. 16: Different human cell lines display different basal Cathepsin B (CTSB) expression levels and different sensitivity to UV irradiation. (a-d). Cells were irradiated with UV at the indicated dosages, collected 48 hours later, and subjected to immunoblotting analysis using anti-CTSB and anti-GAPDH (loading control) antibodies, respectively. Cells were seeded in 6 cm plates and incubated overnight with complete medium. The adherent cells were washed once with PBS, replenished with 1.5 ml of PBS (to keep cells from drying), and irradiated at the indicated UV dosages using a UV cross-linker. After irradiation, PBS was discarded and fresh complete medium was added back to the plates. After 48 hours, all cells, including adherent cells and floating cells, were collected, lysed, and subjected to immunoblotting analysis.

Example 16: This Example Identifies that Different Human Cell Lines Display Different Basal CTSB Expression Levels and Different Sensitivity to UV Irradiation The expression levels of CTSB were examined in four different human immortalized or cancer cell lines (293T, Hela, HepG2 and HCT116, respectively) and their responses to UV irradiation. Before UV irradiation, 293T (embryonic kidney origin) and Hela (cervical tumor origin) cells show little CTSB expression, HepG2 (liver cancer origin) cells show low CTSB expression, and HCT116 (colon cancer origin) cells show high CTSB expression (FIG. 15). After irradiated with different doses of UV, Hela and HepG2 cells showed strong upregulation of CTSB expression, reaching saturation at approximately 100 J/m2, whereas HCT116 cells showed no obvious change in CTSB expression (FIG. 16). 293T cells also exhibited upregulation of CTSB expression in response to UV irradiation, however the CTSB expression levels were rather low (FIG. 16).

Example 17: This Example Identifies Cathepsin B Inhibitors that Block RIBE

Figure 17:
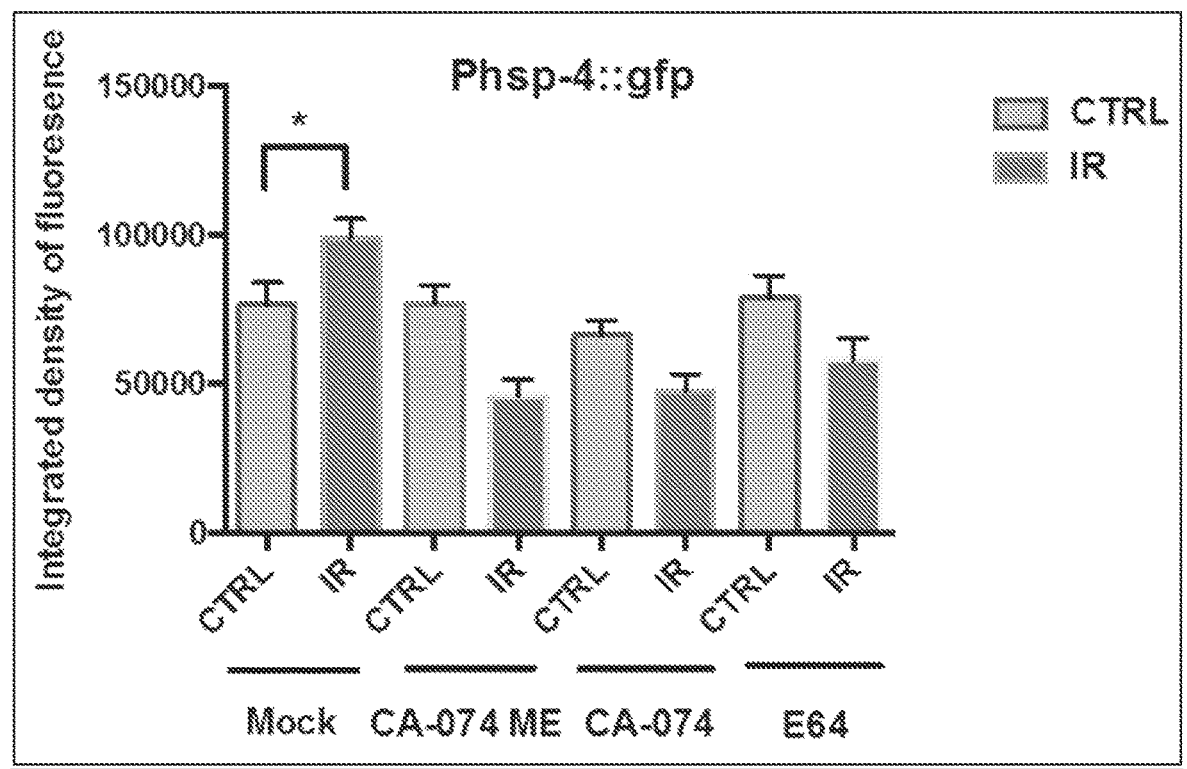
FIG. 17: Several inhibitors of human cathepsin B block RIBE in a localized UV irradiation animal model. zcls4 L1 larvae that carry the integrated Phsp-4::gfp transgene were treated with DMSO (Mock), 1 mM of CA074, CA074Me, or E64, respectively, for 48 h. Assays of the Phsp-4::gfp bystander response to localized UV irradiation (LUI) in the posterior unexposed regions of irradiated animals were performed as described in FIG. 3 above. Data are mean±s.e.m. *P<0.05. two-sided, unpaired t-test.
Figure 18:
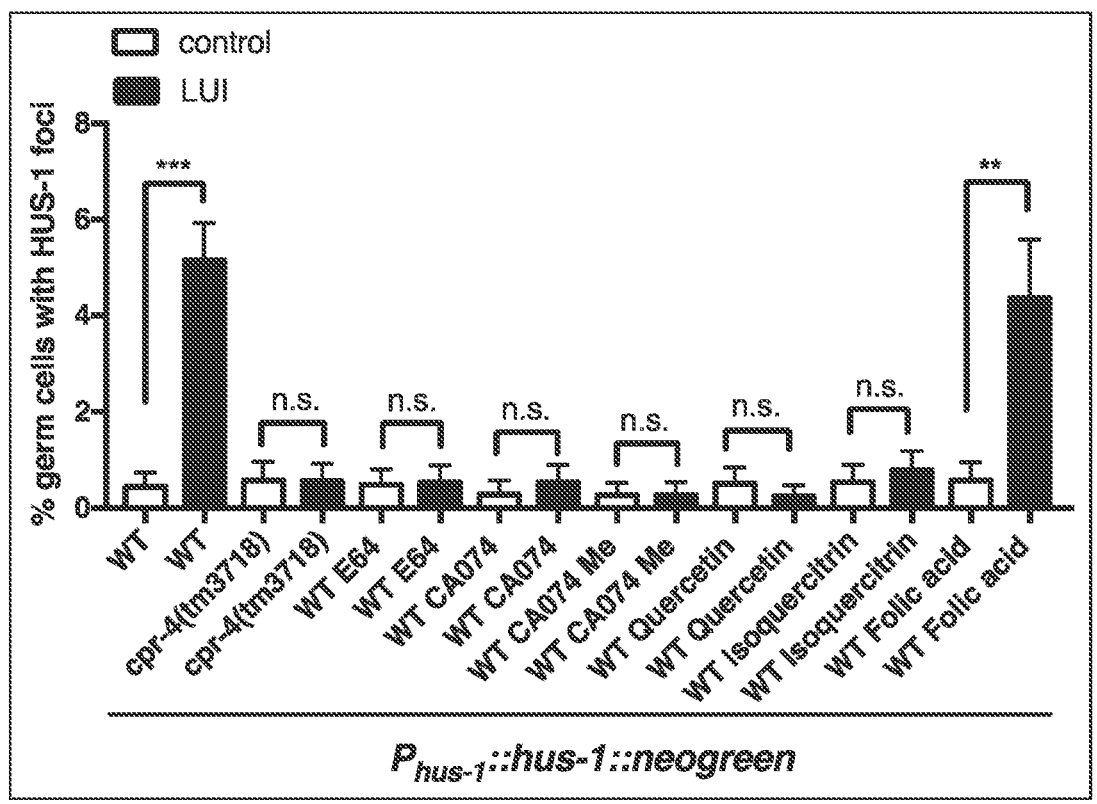
FIG. 18: Inhibition of the chromosomal DNA damage induced by localized UV irradiation (LUI). The chromosomal DNA damage is quantified as the percentage of germ cells in the mitotic region that contain the HUS-1::NeoGreen foci, a DNA damage indicator. In each experiment, at least 15 animals were scored. Larval stage 2 (L2) animals were treated with the drug. Data are mean s.e.m. n.s., not significant; P<0.01, *P<0.001, two-sided, unpaired t-test.

Using a localized UV irradiation (LUI) intra-animal RIBE model (see FIG. 3 above), the present inventors examined if inhibitors of cathepsin B (CTSB) can interfere with RIBE induced by LUI. The present inventors first tested CA074 [N-(1-3-trans-propylcarbamoyloxirane-2-carbonyl)-1-isoleucyl-1-proline], a selective inhibitor of CTSB, and CA074 methyl ester (CA074Me), a membrane-permeant proinhibitor for intracellular cathepsin B. As shown in FIG. 17, treatment with either CA074 or CA74Me abolished the bystander Phsp-4::gfp response in the posterior unexposed regions of the animals treated with LUI at the head regions. The present inventors observed similar results with E64, which is an epoxide that can irreversibly inhibit a wide range of cysteine peptidases, including cathepsin B. These results indicate that human CTSB inhibitors can block RIBE in *C. elegans* and may, in certain embodiments, inhibit RIBE in humans.

Example 18: This Example Identifies *C. elegans* as an Animal Model for Therapeutic Drug Screens for Novel Inhibitors of RIBE Because ectopic pharyngeal expression of CPR-4:: mCherry in *C. elegans* causes significant embryonic lethality and larval arrest (see FIG. 9) and because human CTSB inhibitors block RIBE in *C. elegans* (FIG. 17), the present inventors can take advantage of this feature to screen for novel inhibitors or modulators of RIBE. In one embodiment, adult Pmyo-2::CPR-4::mCherry transgenic animals may be placed on Nematode Growth Media (NGM) plates containing compounds or drugs as previously described above (44, 45). Compounds that can significantly inhibit both embryonic lethality and larval arrest in progeny of Pmyo-2::CPR-4::mCherry transgenic animals may be selected and retested in triplicates. The RIBE inhibitory effects of candidate compounds may be confirmed using the LUI assays as described above.

Example 19: This Example Identifies Various Methods and Apparatus Related to Embodiments of the Present Invention Strains and culture conditions. The present inventors cultured *C. elegans* strains at 20° C. using standard procedures[31], unless otherwise noticed. The present inventors used the N2 Bristol strain as the wild-type strain. The following stains were used in the genetic analyses: LGI, cep-1(gk138), daf-16(mu86), ced-1(e1735); LGII, single copy insertion of Pcpr-4::cpr-4::flag, single copy insertion of Pcpr-4::nls::gfp; LGIII, daf-2(e1370), glp-1(e2141); LGV, cpr-4(tm3718), zcls4 (Phsp-4::gfp); LGX, pdk-1(sa680). Each single-copy insertion transgene was backcrossed at least four times with N2 animals before being used.

Irradiation. Adult animals grown on Nematode Growth Media (NGM) plates or in plastic tubes with liquid culture media were irradiated at room temperature using a UV-cross-linker or a $Co^{60}$ radiation source. The dosage of UV irradiation was 100 $J/m^2$. The dosage of $Co^{60}$ irradiation was 500 Gy at a dosage rate approximately 33.3 Gy/minute. Plates were returned to 20° C. incubators immediately after irradiation. Plastic tubes were placed in a 20° C. shaker after irradiation to generate conditioned medium. Sham-irradiated controls were used in all irradiation experiments.

Generation of conditioned medium from irradiated animals. *C. elegans* animals close to starving were washed off from three NGM plates (6 cm in diameter) and cultured for six days in 250 mL of S-Medium (100 mM NaCl, 5.8 mM $K_2HPO_4$, 44 mM $KH_2PO_4$, 0.013 mM cholesterol, 1 mM citric acid monohydrate, 9 mM tri-potassium citrate monohydrate, 0.05 mM disodium EDTA, 0.025 mM $FeSO_4$, 0.01 mM $MnCl_2$, 0.01 mM $ZnSO_4$, 0.001 mM $CuSO_4$, 1.5 mM $CaCl_2$, 3 mM $MgSO_4$, 0.13 mM ampicillin, 0.007 mM streptomycin sulfate, 0.16 mM neomycin sulfate, and 0.02 mM Nystatin) using plentiful *Escherichia coli* strain HB101 as a food source. The animals were harvested by precipitation at 4° C. for 10 minutes, which were mostly adults, and washed with S-Medium three times. The present inventors adjusted the animal density to approximately 2 animals/µL in S-Medium, transferred them to a quartz plate (with lid), and irradiated them using UV with the desired dosages or sham-irradiated. For IR irradiation, animals at the same density were transferred to 15 mL Corning centrifuge tubes and irradiated using 500 Gy IR or sham-irradiated. The irradiated or sham-irradiated animals were washed with fresh S-Medium, transferred to 15 mL Corning centrifuge tubes in 6 mL S-Medium supplemented with the HB101 bacteria, and grown in a 20° C. shaker for 24 hours with constant 200 rpm shaking. After that, the present inventors removed the animals and bacteria by centrifugation at 3000 rpm for 10 min and filtrated the medium with a 0.22 µm filter unit to obtain conditioned medium. The conditioned medium was then concentrated by passing through a 10 kD ultrafiltration tube (Amicon Ultra-15, Millipore) and adjusted to 0.1 µg/µL total protein concentration using S-Medium. To generate UV-CM and UV-Ctrl from Pcpr-4:: cpr-4::flag; daf-2(eJ730); cpr-4(tm3718) animals, starved plates containing the animals were chunked to 300 new NGM plates, which were placed at 20° C. for 2 days before being shifted to 25° C. for one more day. UV-irradiated or sham-irradiated animals were grown in a 25° C. shaker for 24 hours to obtain UV-CM and UV-Ctrl.

Localized irradiation in *C. elegans*. *C. elegans* L4 larvae were mounted on an agarose pad (2%) with 10 nM Sodium Azide and irradiated at the head region using a Nikon A1 laser scanning confocal on an inverted Ti-E microscope with a 40×/0.9 NA Plan Apo Lambda objective lens. At installation, the 405 nm laser power, which is very close to the wavelength of UV, was measured at 23.32 mW at the fiber. Irradiation was performed using 60% 405 nm laser power at 512×512 with a pixel size of 0.58 micron×0.58 micron for 2.2 microseconds/pixel. Using a Thor labs power meter (PM100D) and photosensor (S140C), the present inventors measured the power at the sample plane to be approximately 0.25-0.30 mW. This corresponds to approximately 0.75-0.89 mW/$micron^2$ at the sample. For sham-irradiation controls, a region slightly away from the animal on the agarose pad was irradiated. After irradiation, the animals were immediately rescued from the agarose pad and transferred to a regular NGM plate to recover at 20° C. for 24 hours or at 25° C. for 20 hours (embryonic lethality assays) before being assayed for intra-animal bystander effects. Three assays were conducted to monitor intra-animal bystander effects in unexposed areas. They are germ cell corpse assays in the posterior gonads, embryonic lethality assays of the F1 progeny of irradiated animals, and Phsp-4::gfp stress response assays in the posterior region. For Phsp-4::gfp stress response assays, experiments using the daf-2(e1370ts) strains and corresponding control strains were performed at 25° C. after LUI. For the embryonic lethality assays, after 20-hour recovery at 25° C., irradiated or sham-irradiated animals were placed on NGM plates to lay eggs for 4 hours at 25° C. and then transferred to new NGM plates. After two more transfers, the animals were discarded. The number of eggs that did not hatch (scored as dead eggs) and the number of eggs that developed into larvae were scored and used to determine the rate of embryonic lethality.

Formaldehyde-treated bacteria as the food source. HB101 bacteria were treated with 3.7% formaldehyde for 10 minutes, washed three times with S-medium, and collected by centrifugation. The death of bacteria was verified by spreading them on a plate with no antibiotics and observing no bacterial colony. The bacterial pellets were added to S-medium to grow worms.

RNA interference (RNAi) experiments. RNAi experiments were performed using a bacterial feeding protocol. HT115 bacteria transformed with the pPD129.36-cpr-4 or the pPD129.36 plasmid were used in cpr-4 RNAi and control RNAi experiments, respectively. Bacterial clones used in other RNAi experiments are from an RNAi library purchased from ThermoFisher. To perform RNAi experiments in liquid culture, three NGM plates with RNAi bacteria were used to feed 30 larval stage 4 (L4) N2 animals until the plates were almost starved. The present inventors then washed the animals off the plates and transferred them to glass flasks with 250 mL of S-Medium containing 0.5 mM Isopropyl β-D-1-thiogalactopyranoside (IPTG) and the RNAi bacteria and grew them for one more generation. The procedure to obtain conditioned medium is similar to that described above.

Growing C. elegans animals in 96-well plates. HB101 bacteria were mixed with 100 μL conditioned medium (0.1 μg/μL) or 100 μL S-Medium containing 2.8 μM of recombinant tCPR-4 proteins (wild-type or mutant) or 0.27 μM recombinant human cathepsin B in a 96-well plate. Approximately 60 L4 larvae were transferred into each well of the plate. After being cultured in liquid media for 48 hours, these animals were scored for the numbers of germ cell corpses and mitotic nuclei.

Enzyme treatment of conditioned medium. The nature of the RIBE factor was analyzed by treating conditioned medium with different enzymes. 1 μL DNase (1 Unit/μL, QIAGEN), 1 μL RNase (100 μg/μL, QIAGEN) or 1 μL Trypsin (5 μg/μL, Sigma) was mixed with 100 μL conditioned medium for 1 hour at 30° C. The treated or untreated conditioned medium was then used to culture ced-1(e1735) animals for 48 hours at 20° C. in a 96-well plate.

Quantification of germ cell corpses. L4 animals were cultured in liquid media in a 96-well plate as described above. After 48 hours, they were transferred to NGM plates and allowed to recover for 1 hour at 20° C. The animals were then anesthetized by 20 mM NaN$_3$, mounted onto 2% agar pad, and scored under Nomarski optics. For transgenic animals expressing CPR-4 in the pharynx, L4 animals were grown on NGM plates for 24 hours at 20° C. before they were scored for germ cell corpses. Only the posterior arms of intact gonads were scored. Blind tests were carried out in all germ cell corpse quantification experiments.

Quantification of mitotic nuclei. L4 animals treated with 2.8 μM of purified tCPR-4 proteins in liquid culture for 48 hours were transferred to NGM plates and allowed to recover for 1 hour at 20° C. They were then dissected to expose their gonads following the protocol described previously [24]. Dissected gonads were fixed and stained with DAPI. The number of germ nuclei and the number of metaphase nuclei in the mitotic zone of each gonad were scored using a Zeiss Nomarski microscope with a DAPI filter.

Quantification of the expression levels of cpr-4 through the GFP reporter. A single-copy insertion of the Pcpr-4::nls::gfp transgene was used to determine the expression levels of cpr-4 before and after irradiation. Middle stage L4 Pcpr-4::nls::gfp and cep-1(gk138); Pcpr-4::nls::gfp larvae were irradiated with 100 J/m$^2$ UV and allowed to recover for 2 hours at 20° C. before imaging. The GFP expression patterns of the animals were recorded by capturing images under Nomarski optics. The exposure times of all images were fixed at 100 ms. The intensity of GFP fluorescence in each animal was quantified using the Image J software (NIH). The expression levels of cpr-4 at different developmental stages (embryos, L1, L2, L3, L4 larvae, adults at 24 hours and 48 hours post L4) without irradiation were determined using the same method.

Embryonic lethality and larval arrest assays. For embryonic lethality assays caused by direct irradiation, after irradiated with 100 J/m$^2$ UV or 500 Gy gamma ray, gravid adults were placed on NGM plates to lay eggs for 4 hours at 25° C. and then removed from the plates. For embryonic lethality assays in liquid media, L4 larvae were cultured in conditioned medium or S-Medium containing the purified proteins at 20° C. for 48 hours, transferred to fresh NGM plates from the liquid media, and allowed to lay eggs for 4 hours at 25° C., before the adult animals were removed. For embryonic lethality assays in transgenic animals expressing CPR-4 in the pharynx, transgenic gravid adults at 24 hours post L4 were placed on NGM plates to lay eggs for 4 hours at 25° C. and then removed from the plates. In all cases, after 24 hours at 25° C. on NGM plates, the number of eggs that did not hatch (scored as dead eggs) and the number of eggs that developed into larvae were scored and used to determine the rate of embryonic lethality.

For the larval arrest assays, gravid transgenic adults were placed on NGM plates, control RNAi plates, or cpr-4 RNAi plates to lay eggs for 4 hours at 25° C. The number of transgenic larvae that hatched out was scored under the fluorescence stereoscope before the plates were returned to the 20° C. incubator. After 3 days, the number of transgenic animals that did not enter the adult stages was scored and used to determine the rate of larval arrest.

Molecular biology. Full-length cpr-4 cDNA was amplified by polymerase chain reaction (PCR) from a C. elegans cDNA library. The signal peptide of CPR-4 is predicted using the SignalP 3.0 Server. To construct the pGEX4T-2-tCPR-4 plasmid, a cpr-4 cDNA fragment encoding residues 16-336 was PCR amplified from the full-length cpr-4 cDNA clone and subcloned into a modified pGEX4T-2 vector through its NdeI and XhoI sites, which has a PreScission Protease cleavage site LEVLFQGP inserted right after the GST coding sequence. To make the pGEX4T-2-tCPR-4 (C109A), pGEX4T-2-tCPR-4(H281A) and pGEX4T-2-tCPR-4(N301A) vectors, two-step PCR was used to generate the tCPR-4 cDNA fragment carrying the indicated mutation, which was subcloned into the same modified pGEX4T-2 vector through its NdeI and XhoI sites. To construct Pmyo-2::CPR-4::mCherry, Pmyo-2::tCPR-4::mCherry, Pmyo-2::CPR-4(C109A)::mCherry, Pmyo-2::CPR-4(H281A)::mCherry, and Pmyo-2::CPR-4(N301A)::mCherry expression vectors, the cDNA fragments encoding full-length CPR-4(C109A), CPR-4 (H281A) and CPR-4 (N301A) were first generated using a two-step PCR method. The DNA fragments encoding CPR-4::mCherry, tCPR-4::mCherry, CPR-4(C109A)::mCherry, CPR-4(H281A)::mCherry and CPR-4(N301A)::mCherry were similarly PCR amplified and subcloned into a modified pCFJ90 vector (Addgene) through its NheI sites.

To make the plasmid pCFJ151-Pcpr-4::cpr-4::flag for generating the single copy integrated transgene, a cpr-4 genomic fragment (Pcpr-4::cpr-4::utr), containing 4018 bp of the cpr-4 promoter sequence, 1196 bp of the cpr-4 genomic coding sequence, and 2267 bp of the cpr-4 3' untranslated region (UTR), was excised from a fosmid WRM0619bH11 through digestion with PmlI and BssHII and then subcloned into a modified pCFJ151 plasmid through its BssHII site and a blunted AvrII site. This Pcpr-4::cpr-4::utr genomic fragment was then excised from the plasmid through AflII and NheI digestion and subcloned into a plasmid pSL1190 through its AflII and NheI sites. A Flag tag (DYKDDDDK) was inserted immediately after the cpr-4 coding region through the QuickChange method. The modified Pcpr-4::cpr-4::flag::utr genomic fragment was subcloned back to pCFJ151 through its AflII and NheI sites to obtain the plasmid pCFJ151-Pcpr-4::cpr-4::flag.

To construct the plasmid pSL1190-Pcpr-4::nls::gfp for single copy insertion, a 4114 bp fragment containing the cpr-4 promoter and the first 58 bp of the cpr-4 coding region, a 1767 bp fragment containing the NLS::GFP coding sequence and the unc-54 3'UTR, a 1337 bp upstream homologous recombination fragment of the LGII Mos I site (ttTi5605) and a 1418 bp downstream homologous recombination fragment of the LGII MosI site were ligated into the pSL1190 plasmid backbone through its PstJ and BamHI sites using the Gibson ligation method.

To construct the plasmid for cpr-4 RNAi, full-length cpr-4 cDNA fragment was PCR amplified and subcloned into the pPD129.36 vector through its Nhe I and Xho I sites. All clones generated were confirmed by DNA sequencing.

Transgenic animals. Transgenic animals were generated using the standard protocol. Pmyo-2::CPR-4::mCherry, Pmyo-2::tCPR-4::mCherry, Pmyo-2::CPR-4(C109A)::mCherry, Pmyo-2::CPR-4(H281A)::mCherry, or Pmyo-2::CPR-4(N301A)::mCherry was injected into ced-1(e1735); cpr-4(tm3718) animals at 20 ng/µL (for quantification of germ cell corpses) or 2 ng/µL (for embryonic lethality and larval arrest assays) along with the pTG96 plasmid (at 20 ng/µL) as a co-injection marker. The pTG96 plasmid contains a sur-5::gfp translational fusion that is expressed in many cells and in most developmental stages [37]. Single-copy insertion Pcpr-4::cpr-4::flag transgene and Pcpr-4::nls::gfp transgene were generated using a method described previously.

Immunoblotting detection of secreted CPR-4::Flag. Conditioned medium derived from irradiated N2, Pcpr-4::cpr-4::flag, Pcpr-4::cpr-4::flag; cpr-4(tm3178), cep-1(gk138); Pcpr-4::cpr-4::flag, or Pcpr-4::cpr-4::flag; daf-2(e1370); cpr-4(tm3178) animals was concentrated using a 10 kD molecular weight cut-off (MWCO) centrifugal filter column (1 µg/µL final protein concentration). Concentrated conditioned media were resolved on a 12% SDS polyacrylamide gel (SDS-PAGE) and transferred to a PVDF membrane. Secreted CPR-4::Flag was detected using a monoclonal antibody to the Flag tag (Sigma, catalog number F3165, 1:2000 dilution) and a goat-anti-mouse secondary antibody conjugated with horseradish peroxidase (HRP, Bio-Rad, catalog number 1705047, 1:5000 dilution).

CPR-4::Flag depletion. UV-CM or UV-Ctrl derived from Pcpr-4::cpr-4::flag; cpr-4(tm3718) animals were incubated with 20 µL bed volume anti-Flag M2 affinity gel (Sigma, catalog number A2220) overnight at 4° C. on a rotary shaker. The anti-Flag beads were spun down by centrifugation at 10,000 rpm for 2 minutes and the supernatant was collected and used as anti-Flag-depleted conditioned medium.

Protein expression and purification. tCPR-4 or mutant tCPR-4 proteins (C109A, H281A, or N301A) were expressed in the *Escherichia coli* strain BL21(DE3) with a N-terminal GST tag and a C-terminal His6-tag. The soluble fraction of bacteria was purified using a Glutathione Sepharose column (GE Healthcare, catalog number 17-0756-01) and cleaved by the PreScission Protease at room temperature for 2 hours to remove the GST tag. The proteins were then affinity purified using a $Ni^{2+}$ Sepharose column (GE Healthcare, catalog number 17-5268-01) and eluted from the column with 250 mM imidazole. Purified proteins were concentrated using 5 kD MWCO centrifugal filter units to approximately 200 ng/µL final concentration and dialyzed twice using a dialysis buffer containing 25 mM Tris-HCl (pH 8.0), 100 mM NaCl, 1 mM DTT and 10% (v/v) glycerol at 4° C. for 4-6 hours with magnetic stirring. Insoluble aggregates after dialysis were removed by high-speed centrifugation. The proteins were then diluted to 100 ng/µL final concentration with the dialysis buffer and stored at −80° C. in aliquots. The concentrations of purified proteins were determined by anti-His6 immunoblotting, using tCPR-4-His6 with a known concentration as a normalizing control.

Mass spectroscopy analysis. The protein bands of interests excised from the silver-stained gels were destained by 1% potassium ferricyanide and 1.6% sodium thiosulfate, subjected to reduction and alkylation by 10 mM DTT and 55 mM iodoacetamide in 25 mM $NH_4HCO_3$, and then in-gel digested with trypsin (20 µg/mL in 25 mM $NH_4HCO_3$) at 37° C. for 16 hours. The reaction products were analyzed with liquid chromatography tandem mass spectrometry (LC-MS/MS) using a linear ion trap mass spectrometer (LTQ-Orbitrap, Thermo Fisher). Samples were loaded across a trap column (Zorbax 300SB-C18, 0.3×5 mm, Agilent Technologies) and peptides were separated on an analytical column (capillary RP18 column, Synergy hydro-RP, 2.5 µm, 0.075×100 mm, packed in house) with a gradient of 2-95% HPLC buffer (99.9% acetonitrile containing 0.1% formic acid) in 75 minutes. For the MS analysis, the present inventors used a data-dependent procedure that alternated between one MS scan and six MS/MS scans for the six most abundant precursor ions. The resulting spectra were used in searches of the sprot_20140416 database (selected for *Caenorhabditis elegans*, 3466 entries) assuming the digestion enzyme trypsin. The MASCOT search engine (http://www.matrix-science.com; v.2.2.2 Matrix Science) was used, allowing two missing cleavage sites with charge states from $2^+$ to $3^+$. The parent ion mass tolerance was set to 10 ppm and the fragment ion mass tolerance was set to 0.5 Da for both fix modification (carbamidomethylation of cysteine) and variable modifications (acetylation at protein N-terminal, oxidation of methionine, and Gln change to pyro-Glu). The DAT files produced by Mascot Daemon were subjected to search using Scaffold 3 search engine (v.3.06.01; http://www.proteomesoftware.com). Protein identification is accepted if protein probability is >95%, containing at least two peptides with peptide prophet algorithm probability >95%.

Measurement of protease activity in vitro. The CPR-4 enzymatic assays were performed following the method described previously with some modifications. The cathepsin B-specific fluorogenic substrate, Z-Arg-Arg-7-amido-4-methylcoumarin hydrochloride (z-Arg-Arg-AMC; Peptanova, catalog number 88937-61-5), was dissolved in 2×reaction buffer, containing 25 mM Tris-HCl (pH 8.0), 100 mM NaCl, 10% (v/v) Glycerol, 0.8 mM Sodium Acetate (pH6.0), and 8 mM EDTA. For the assays, 10 µL of proteins (100 ng/µL) or 10 µL of conditioned medium (100 ng/µL) were incubated with 10 µL of 20 µM z-Arg-Arg-AMC at 25° C. for 10 minutes before measuring the luminescence. Enzymatic activities were determined as the mean velocities at 25° C. in a dual luminescence fluorometer EnVision (Perkin-Elmer) at an excitation wavelength of 380 nm and an emission wavelength of 460 nm, and expressed as relative intensity in kilo relative fluorescence unit (kRFU). Recombinant human cathepsin B (rhCTSB; Sino Biological Inc., catalog number 10483-H08H-10) was dissolved in a buffer recommended by the manufacturer [25 mM Tris-HCl (pH 8.0), 100 mM NaCl, 10% (v/v) glycerol, 5 mM DTT, and 0.1% Triton-X]. The buffer control unique to the CPR-4 proteins or the rhCTSB protein, or the sham-irradiated conditioned medium, was also measured using the same procedures. S-Medium was used in each experiment as the background control.

Quantitative RT-PCR analysis of the cpr-4 transcriptional levels. N2 and cep-1(gk138) L4 larvae were transferred to fresh NGM plates and cultured at 20° C. for 24 hours. Two hours after they were subjected to 100 J/m$^2$ UV or 500 Gy gamma ray irradiation or sham-irradiation, they were lysed for total RNA extraction using the RNAiso kit (TaKaRa, catalog number 9108). Isolated total RNAs were used as templates in reverse transcription (RT) using the ImProm-II™ Reverse Transcription System (Promega, catalog number A3800) to obtain the first strand cDNA according to manufacturer's instructions.

Quantitative PCR analysis was carried out using a Bio-Rad CFX96 Touch real-time PCR detection system using the iTaq™ SYBR® Green Supermix with ROX (Bio-Rad, catalog number 1725151). Each PCR reaction contained 12.5 µL of the Bio-Rad supermix solution, 50 nM of forward and reverse primers, and 5 µL cDNA (150 ng/µL) in a final volume of 25 µL. Amplifications were performed in real-time PCR tubes (Bio-Rad, catalog number TLS0851) placed in the 96-well of the real-time PCR detection system. The cycling conditions were as follows: 95° C. for 3 minutes for denaturation, followed by 50 cycles of 20 seconds at 95° C., 30 seconds at 60° C., and 20 seconds at 72° C. Melting curve analysis was performed after the final cycle to examine the specificity of primers in each reaction. PCR reactions were run in triplicate and three independent experiments were performed. The transcription of pmp-3 was used as the internal reference due to its unusually stable expression levels in adults. The data were analyzed by the Livak method. The primers to detect cpr-4 are:

```
(forward primer)
5'-TCGGAAAGAAGGTCTCCCAGAT-3';
and (reverse primer)
5'-GGTAGAAGTCCTCGTAGACAGTGAAT-3'.
```

The primers to detect pmp-3 are:

```
(forward primer)
5'-GTTCCCGTGTTCATCACTCAT-3';
and (reverse primer)
5' ACACCGTCGAGAAGCTGTAGA-3'.
```

Localized irradiation in *C. elegans* coupled with screened compounds. *C. elegans* L4 larvae were mounted on an agarose pad (2%) with 10 nM sodium azide and irradiated at the head region using a Nikon A1 laser scanning confocal on an inverted Ti-E microscope with a 40x/0.9 NA Plan Apo Lambda objective lens. At installation, the 405 nm laser power, which is very close to the wavelength of UV, was measured at 23.32 mW at the fibre. Irradiation was performed using 60% 405 nm laser power at 512×512 with a pixel size of 0.58 µm×0.58 µm for 2.2 µs pixel$^{-1}$. Using a Thor labs power meter (PM100D) and photosensor (S140C), the present inventors measured the power at the sample plane to be approximately 0.25-0.30 mW. This corresponds to approximately 0.75-0.89 mW µm$^{-2}$ at the sample. For sham-irradiation controls, a region slightly away from the animal on the agarose pad was irradiated. After irradiation, the animals were immediately rescued from the agarose pad and transferred to a regular NGM plate to recover at 20° C. for 24 hours or at 25° C. for 20 hours (embryonic lethality assays) before being assayed for intra-animal bystander effects. Three assays were conducted to monitor intra-animal bystander effects in unexposed areas. They are hus-1::NeoGreen chromosomal DNA damage assays in the gonads, embryonic lethality assays of the F1 progeny of irradiated animals, and Phsp-4::gfp stress response assays in the posterior region.

Measurement of the CTSB or CPR-4 protease activity in vitro. The cathepsin B-specific fluorogenic substrate, Z-Arg-Arg-7-amido-4-methylcoumarin hydrochloride (z-Arg-Arg-AMC; Peptanova, 88937-61-5), was dissolved in 2× reaction buffer, containing 25 mM Tris-HCl (pH 8.0), 100 mM NaCl, 10% (v/v) glycerol, 0.8 mM sodium acetate (pH6.0), and 8 mM EDTA. For the assays, 5 µL of proteins (100 ng µl$^{-1}$) and 5 µL of the compound were incubated with 10 µL of 20 µM z-Arg-Arg-AMC at 37° C. for 60 min before measuring the luminescence. Enzymatic activities were determined as the mean velocities at 37° C. in a fluorimeter Molecular Devices Spectra MAX M5 at an excitation wavelength of 380 nm and an emission wavelength of 460 nm. Distilled deionized water was used in each experiment as the background control. Inhibition rate=(control OD−OD with compound)/control OD×100%. Values of IC$_{50}$ were determined by inhibition rate measurements with at least six different inhibitor concentrations. All kinetic parameters were determined by nonlinear regression employing GraphPad Prism 7.0 (GraphPad Software, San Diego, Calif.).

Embryonic lethality assays. For the embryonic lethality assays, after 20 hour recovery at 25° C. after the LUI treatment, irradiated or sham-irradiated animals were placed on NGM plates to lay eggs for 4 hours at 25° C. and then transferred to new NGM plates. After two more transfers, the animals were discarded. The number of eggs that did not hatch (scored as dead eggs) and the number of eggs that developed into larvae were scored and used to determine the rate of embryonic lethality. For embryonic lethality assays with the antibody treatment, L4 larvae were placed on NGM plates to recover for 6 hours after the LUI treatment, then cultured in the M9 buffer containing the 100-fold diluted anti-Flag M2 antibody (Sigma) at 20° C. for 12 hours, transferred to fresh NGM plates from the liquid medium, and allowed to lay eggs for 4 hours at 25° C. After two more transfers, the animals were discarded and the rate of embryonic lethality was scored as above.

HUS-1::NeoGreen chromosomal DNA damage assay. Chromosomal DNA damage in *C. elegans* mitotic germ cells was assessed using the wild-type animals carrying a hus-1::neogreen knock-in. After the LUI treatment, the irradiated animals were mounted on microscope slides in 0.2 mM Levamisole (Sigma), and the HUS-1::NeoGreen foci in a single Z stack were scored using a Nomarski microscope (Zeiss, Germany). The percentage of mitotic germ cells with the HUS-1::NeoGreen foci were then determined.

Those skilled in the art will appreciate, or be able to ascertain using no more than routine experimentation, further features and advantages of the invention based on the above-described embodiments. Accordingly, the invention is not to be limited by what has been particularly shown and described. All publications and references are herein expressly incorporated by reference in their entirety.

REFERENCES

Each of the following references are incorporated by reference.

[1] Mothersill, C. & Seymour, C. Radiation-induced bystander effects: past history and future directions. *Radiat. Res.* 155, 759-767 (2001).

[2] Prise, K. M. & O'Sullivan, J. M. Radiation-induced bystander signalling in cancer therapy. *Nat. Rev. Cancer* 9, 351-360 (2009).

[3] Rzeszowska-Wolny, J., Przybyszewski, W. M. & Widel, M. Ionizing radiation-induced bystander effects, potential targets for modulation of radiotherapy. *Eur J. Pharmacol.* 625, 156-164 (2009).

[4] Stergiou, L., Doukoumetzidis, K., Sendoel, A. & Hengartner, M. O. The nucleotide excision repair pathway is required for UV-C-induced apoptosis in *Caenorhabditis elegans*. *Cell Death Differ* 14, 1129-1138 (2007).

[5] Derry, W. B., Putzke, A. P. & Rothman, J. H. *Caenorhabditis elegans* p53: Role in apoptosis, meiosis, and stress resistance. *Science* 294, 591-595 (2001).

[6] Schumacher, B., Hofmann, K., Boulton, S. & Gartner, A. The *C. elegans* homolog of the p53 tumor suppressor is required for DNA damage-induced apoptosis. *Curr Biol.* 11, 1722-1727 (2001).

[7] Klokov, D. et al. Low dose IR-induced IGF-1-sCLU expression: a p53-repressed expression cascade that interferes with TGFbeta1 signaling to confer a pro-survival bystander effect. *Oncogene* 32, 479-490 (2013).

[8] Koturbash, I. et al. In vivo bystander effect: Cranial X-irradiation leads to elevated DNA damage, altered cellular proliferation and apoptosis, and increased p53 levels in shielded spleen. *Int. J. Radiat. Oncol. Biol. Phys.* 70, 554-562 (2008).

[9] Sun, Y. et al., Treatment-induced damage to the tumor microenvironment promotes prostate cancer therapy resistance through WNT16B. *Nat. Med.* 18, 1359-1368 (2012).

[10] Buck, M. R., Karustis, D. G., Day, N. A., Honn, K. V. & Sloane, B. F. Degradation of Extracellular-Matrix Proteins by Human Cathepsin-B from Normal and Tumor-Tissues. *Biochem. J.* 282, 273-278 (1992).

[11] Poole, A. R., Tiltman, K. J., Recklies, A. D. & Stoker, T. A. Differences in secretion of the proteinase cathepsin B at the edges of human breast carcinomas and fibroadenomas. *Nature* 273, 545-547 (1978).

[12] Larminie, C. G. & Johnstone, I. L. Isolation and characterization of four developmentally regulated cathepsin B-like cysteine protease genes from the nematode *Caenorhabditis elegans*. *DNA Cell Biol.* 15, 75-82 (1996).

[13] Lorimore, S. A., Rastogi, S., Mukherjee, D., Coates, P. J. & Wright, E. G. The influence of p53 functions on radiation-induced inflammatory bystander-type signaling in murine bone marrow. *Radiat. Res.* 179, 406-415 (2013).

[14] Calfon, M. et al. IRE1 couples endoplasmic reticulum load to secretory capacity by processing the XBP-1 mRNA. *Nature* 415, 92-96 (2002).

[15] Bertucci, A., Pocock, R. D., Randers-Pehrson, G. & Brenner, D. J. Microbeam irradiation of the *C. elegans* nematode. *J Radiat. Res.* 50 Suppl A, A49-54 (2009).

[16] Mort, J. S. & Buttle, D. J. Cathepsin B. *Int. J. Biochem. Cell Biol.* 29, 715-720 (1997).

[17] Shore, D. E. & Ruvkun, G. A cytoprotective perspective on longevity regulation. *Trends Cell Biol.* 23, 409-420 (2013).

[18] Kenyon, C. J. The genetics of ageing. *Nature* 464, 504-512 (2010).

[19] Perrin, A. J. et al. Noncanonical control of *C. elegans* germline apoptosis by the insulin/IGF-1 and Ras/MAPK signaling pathways. *Cell Death Differ* 20, 97-107 (2013).

[20] Scott, B. A., Avidan, M. S. & Crowder, C. M. Regulation of hypoxic death in *C. elegans* by the insulin/IGF receptor homolog DAF-2. *Science* 296, 2388-2391 (2002).

[21] Paradis, S., Ailion, M., Toker, A., Thomas, J. H. & Ruvkun, G. A PDK1 homolog is necessary and sufficient to transduce AGE-1 PI3 kinase signals that regulate diapause in *Caenorhabditis elegans*. *Genes Dev.* 13, 1438-1452 (1999).

[22] Lin, K., Dorman, J. B., Rodan, A. & Kenyon, C. daf-16: An HNF-3/forkhead family member that can function to double the life-span of *Caenorhabditis elegans*. *Science* 278, 1319-1322 (1997).

[23] Ogg, S. et al. The Fork head transcription factor DAF-16 transduces insulin-like metabolic and longevity signals in *C. elegans*. *Nature* 389, 994-999 (1997).

[24] Michaelson, D., Korta, D. Z., Capua, Y. & Hubbard, E. J. Insulin signaling promotes germline proliferation in *C. elegans*. *Development* 137, 671-680 (2010).

[25] Pinkston, J. M., Garigan, D., Hansen, M. & Kenyon, C. Mutations that increase the life span of *C. elegans* inhibit tumor growth. *Science* 313, 971-975 (2006).

[26] Nikjoo, H. & Khvostunov, I. K. A theoretical approach to the role and critical issues associated with bystander effect in risk estimation. *Hum. Exp. Toxicol.* 23, 81-86 (2004).

[27] Mothersill, C. & Seymour, C. Radiation-induced bystander and other non-targeted effects: novel intervention points in cancer therapy? *Curr Cancer Drug Targets* 6, 447-454 (2006).

[28] Recklies, A. D., Tiltman, K. J., Stoker, T. A. & Poole, A. R. Secretion of proteinases from malignant and non-malignant human breast tissue. *Cancer Res.* 40, 550-556 (1980).

[29] Barrett, A. J. & Kirschke, H. Cathepsin B, Cathepsin H, and cathepsin L. *Methods Enzymol.* 80 Pt C, 535-561 (1981).

[30] Shree, T. et al. Macrophages and cathepsin proteases blunt chemotherapeutic response in breast cancer. *Genes Dev.* 25, 2465-2479 (2011).

[31] Brenner, S. The genetics of *Caenorhabditis elegans*. Genetics 77, 71-94 (1974).

[32] Frokjaer-Jensen, C. et al., Single-copy insertion of transgenes in *Caenorhabditis elegans*. *Nat. Genet.* 40, 1375-1383 (2008).

[33] Timmons, L., Court, D. L. & Fire, A. Ingestion of bacterially expressed dsRNAs can produce specific and potent genetic interference in *Caenorhabditis elegans*. *Gene* 263, 103-112 (2001).

[34] Pepper, A. S. R., Killian, D. J. & Hubbard, E. J. A. Genetic analysis of *Caenorhabditis elegans* glp-1 mutants suggests receptor interaction or competition. *Genetics* 163, 115-132 (2003).

[35] Bendtsen, J. D., Nielsen, H., von Heijne, G., & Brunak, S., Improved prediction of signal peptides: SignalP 3.0. *J. Mol. Biol.* 340, 783-795 (2004).

[36] Mello, C. C., Kramer, J. M., Stinchcomb, D., & Ambros, V., Efficient Gene-Transfer in C-*Elegans*-Extra-chromosomal Maintenance and Integration of Transforming Sequences. *EMBO J.* 10, 3959-3970 (1991).

[37] Gu, T., Orita, S. & Han, M. *Caenorhabditis elegans* SUR-5, a novel but conserved protein, negatively regulates LET-60 Ras activity during vulval induction. *Mol. Cell Biol.* 18, 4556-4564 (1998).

[38] Paquet, C., Sane, A. T., Beauchemin, M. & Bertrand, R. Caspase- and mitochondrial dysfunction-dependent mechanisms of lysosomal leakage and cathepsin B activation in DNA damage-induced apoptosis. *Leukemia* 19, 784-791 (2005).

[39] Hoogewijs, D., Houthoofd, K., Matthijssens, F., Vandesompele, J. & Vanfleteren, J. R. Selection and validation of a set of reliable reference genes for quantitative sod gene expression analysis in *C. elegans*. *BMC Mol. Biol.* 9, 9 (2008).

[40] Timmons, L., Court, D. L. & Fire, A. Ingestion of bacterially expressed dsRNAs can produce specific and potent genetic interference in *Caenorhabditis elegans*. *Gene* 263, 103-112 (2001).

[41] Sumiya, S., Yoneda, T., Kitamura, K., Murata, M., Yokoo, C., Tamai, M., Yamamoto, A., Inoue, M. & Ishida, T. Molecular design of potent inhibitor specific for cathepsin B based on the tertiary structure prediction. *Chem. Pharm. Bull.* 40, 299-303 (1992).

[42] Buttle, D., Murata, M., Knight, C. & Barrett, A. CA074 methyl ester: A proinhibitor for intracellular cathepsin B. *Arch. Biochem. Biophys.* 299, 377-380 (1992).

[43] Gour-Salin, B. et al. E64 [trans-epoxysuccinyl-1-leucylamido-(4-guanidino)butane]analogues as inhibitors of cysteine proteinases: investigation of S2 subsite interactions. *Biochem. J.* 299, 389-392 (1994).

[44] Kokel, D., Li, Y. H., Qin, J., and Xue, D. The non-genotoxic carcinogens naphthalene and para-dichlorobenzene suppress apoptosis in *C. elegans*. *Nature Chemical Biology* 2, 338-345 (2006).

[45] Kokel, D. and Xue, D. (2006). A class of benzenoid chemicals suppresses apoptosis in *C. elegans*. *ChemBioChem* 7, 2010-2015 (2006).

[46] Hofmann E R, Milstein S, Boulton S J, et al. *Caenorhabditis elegans* HUS-1 is a DNA damage checkpoint protein required for genome stability and induction of EGL-1. *Curr. Biol.* 12, 1908-1918 (2002).

[47] Peng Y, Zhang M, Zheng L, et al. Cysteine protease cathepsin B mediates radiation induced bystander effects. *Nature.* 547, 458-462 (2017).

TABLE 1

Screens for compounds that inhibit CTSB activity and RIBE.

| NO. | Name of compound |
|---|---|
| 1 | Catechin hydrate |
| 2 | Apigenin |
| 3 | Baicalein |
| 4 | Isoquercitrin |
| 5 | Curcumin |
| 6 | Resveratrol |
| 7 | Quercetin |
| 8 | Rutin |
| 9 | Astaxanthin |
| 10 | Tannic acid |
| 11 | Ganoderic acid B |
| 12 | Folic acid |
| 13 | Ascorbic acid |
| 14 | $NH_2$-Arg-Leu-Ala-COOH |
| 15 | $NH_2$-Arg-Leu-Ala-COOH—Se |
| 16 | CA074Me |
| 17 | CA074 |
| 18 | E64 |

TABLE 2

Screens for compounds that inhibit the CTSB protease activity.

| Name of compound | Inhibition rate (%) |
|---|---|
| Apigenin | 70.93 |
| Isoquercitrin | 68.98 |
| Quercetin | 82.42 |
| Tannic acid | 69.29 |
| Ca074Me | 88.13 |
| Ca074 | 91.81 |
| E64 | 92.13 |
| Folic acid | −425.60 |
| Baicalein | 82.76 |
| $NH_2$-Arg-Leu-Ala-COOH | 86.12 |
| $NH_2$-Arg-Leu-Ala-COOH—Se | 86.93 |

1 mM of each compound was used in the protease inhibition assay

TABLE 3

IC50 of the compounds in inhibiting the CTSB protease activity.

| Name of compound | IC50(μM) | EC50(μM) |
|---|---|---|
| Quercetin | 1.87 | |
| F-64 | 0.02 | |
| Folic acid | | 1.26 |
| Baicalein | 0.87 | |
| $NH_2$-Arg-Leu-Ala-COOH | 12.21 | |
| CA074 | 0.01 | |
| CA074 Me | <0.01 | |

TABLE 4

The activity of the compounds in inhibiting the *C. elegans* CPR-4 protease activity.

| Name of compound | Inhibition rate(%) |
|---|---|
| Quercetin | 80.67 |
| E64 | 89.59 |
| Baicalein | 41.54 |
| $NH_2$-Arg-Leu-Ala-COOH | 85.03 |

1 mM of each compound was used in the CPR-4 protease inhibition assay

TABLE 5

A summary of peptide identification information in bands 1-10 by LC-MS/MS analysis using LTQ-Orbitrap.

| Band No. | Protein name | Gene name | Protein ID probability | No. of unique peptides | Percentage of sequence coverage |
|---|---|---|---|---|---|
| 1 | Not determined | | | | |
| 2 | Putative serine protease K12H4.7 | K12H4.7 | 99.80% | 2 | 5.29% |
|   | Elongation factox 1-alpha | eft-3 | 99.80% | 2 | 4.10% |
| 3 | Putative serine protease K12H4.7 | K12H4.7 | 100.00% | 3 | 7.65% |
|   | Putative phospholipase B-like 1 | Y37D8A.2 | 100.00% | 2 | 5.78% |
| 4 | Aspartic protease 6 | asp-6 | 100.00% | 4 | 19.00% |
| 5 | Cathepsin B-like cysteine proteinase 4 | cpr-4 | 100.00% | 3 | 11.30% |
|   | Muscle M-line assembly protein unc-89 | unc-89 | 99.90% | 2 | 0.24% |
|   | Uncharacterized serine carboxypeptidase F13S12.6 | F13D12.6 | 99.80% | 2 | 4.41% |
|   | Aspartic protease 6 | asp-6 | 99.80% | 2 | 10.80% |
| 6 | Aspartic protease 6 | asp-6 | 100.00% | 6 | 19.00% |
|   | Uncharactetized serine carboxypeptidase K10B2.2 | K10B2.2 | 100.00% | 3 | 7.66% |
|   | DNA repair protein rad-50 | rad-50 | 99.80% | 2 | 0.92% |
|   | Cathepsin B-like cysteine proteinase 4 | cpr-4 | 99.80% | 2 | 8.36% |
| 7 | Actin-1 | act-1 | 100.00% | 7 | 18.40% |
|   | Histone H4 | his-1 | 100.00% | 5 | 41.70% |
|   | Elongation factor 1-alpha | eft-3 | 100.00% | 3 | 6.26% |
|   | Superoxide dismutase [Cu—Zn] | sod-1 | 100.00% | 3 | 23.30% |
|   | 14-3-3-like protein 1 | par-5 | 99.80% | 2 | 7.26% |
|   | Histone H3.3 type 1 | his-71 | 100.00% | 2 | 10.30% |
|   | Ubiquitin-60S ribosomal protein 1.40 | ubq-2 | 99.80% | 2 | 11.70% |
|   | Histone H2B 2 | his-4 | 99.80% | 2 | 13.00% |
| 8 | Uncharacterized serine carboxypeptidase F13S12.6 | F13D12.6 | 100.00% | 5 | 10.40% |
|   | Fatty-acid and retinol-binding protein 2 | far-2 | 100.00% | 3 | 17.00% |
|   | UPF0375 protein C08F11.11 | C08F11.11 | 100.00% | 3 | 36.00% |
|   | Actin-1 | act-1 | 99.90% | 2 | 7.45% |
|   | RutC family protein C23G10.2 | C23G10.2 | 99.80% | 2 | 13.50% |
| 9 | Aspartic protease 6 | asp-6 | 100.00% | 3 | 11.60% |
|   | Uncharacterized serine carboxypeptidase F13S12.6 | F13D12.6 | 99.70% | 2 | 4.85% |
|   | Cathepsin B-like cysteine proteinase 4 | cpr-4 | 99.70% | 2 | 8.36% |
| 10 | Aspartic protease 6 | asp-6 | 100.00% | 4 | 9.77% |
|   | Uncharacterized serine carboxypeptidase F13S12.6 | F13D12.6 | 99.80% | 2 | 4.85% |
|   | Cathepsin B-like cysteine proteinase 4 | cpr-4 | 99.80% | 2 | 10.40% |
|   | Histone H4 | his-1 | 99.80% | 2 | 17.50% |

TABLE 6

A summary of cpr-4 RNAi treatment of Pmyo-2::CPR-4::mCherry transgenic animals. All strains contain the ced-1(e1735) and cpr-4(tm3718) mutations. RNAi experiments were carried out using a bacteria-feeding protocol.

| Genotype | Larval arrest (%) | n |
|---|---|---|
| Control RNAi | 0% | 150 |
| cpr-4 RNAi | 0% | 150 |
| Ex[Pmyo-2::CPR-4::mCherry]#1; Control RNAi | 9% | 135 |
| Ex[Pmyo-2::CPR-4::mCherry]#2; Control RNAi | 7% | 172 |
| Ex[Pmyo-2::CPR-4::mCherry] #1; cpr-4 RNAi | 1% | 136 |
| Ex[Pmyp-2::CPR-4::mCherry] #2; cpr-4 RNAi | 1% | 163 |

What is claimed is:

1. A method for treating radiation-induced bystander effects (RIBE) in non-irradiated cells of a subject caused by exposure to radiation, comprising administering to the subject a therapeutically effective amount of quercetin, isoquercetin, or a combination thereof, wherein said therapeutically effective amount inhibits the activity of Cathepsin B (CTSB), preventing RIBE in said non-irradiated cells.

2. The method of claim 1 and further comprising the step of administering to the subject a therapeutically effective amount of quercetin, isoquercetin, or a combination thereof in a pharmaceutically acceptable carrier wherein said pharmaceutically acceptable carrier is an aqueous and/or non-aqueous pharmaceutically acceptable carrier.

3. The method of claim 2 wherein said therapeutically effective amount of said quercetin, isoquercetin, or a combination thereof, inhibits the protease activity of CTSB.

4. The method of claim 3 wherein said therapeutically effective amount of said quercetin, isoquercetin, or a combination thereof, is administered prior to the administration of the radiotherapy, along with to the administration of the radiotherapy, or after the administration of the radiotherapy.

5. The method of claim 2 wherein said therapeutically effective amount of said quercetin, isoquercetin, or a combination thereof, is administered in combination with an anti-cancer therapy.

6. The method of claim 5 wherein said anti-cancer therapy is selected from the group consisting of surgery, immunotherapy, and chemotherapy, or a combination of the same.

7. The method of claim 3 wherein said therapeutically effective amount of said quercetin, isoquercetin, or a combination thereof, alters cell death or cell proliferation, reduces DNA damage, or increases DNA repair in the subject.

8. The method of claim 3 wherein said therapeutically effective amount of said quercetin, isoquercetin, or a combination thereof, reduces and/or prevents RIBE in a subject.

9. The method of claim 3 wherein said therapeutically effective amount of said quercetin, isoquercetin, or a combination thereof, produces at least one of the following effects in a subject:
    increases the effectiveness of radiotherapy and/or chemotherapy in a cancer subject in the subject;
    reduces resistance of cancer cells to radiotherapy and/or chemotherapy in the subject; and
    increases the subject's tolerance to radiotherapy.

* * * * *

SEQUENCE LISTING

<160> NUMBER OF SEQ ID NOS: 5

<210> SEQ ID NO 1
<211> LENGTH: 339
<212> TYPE: PRT
<213> ORGANISM: C. elegans

<400> SEQUENCE: 1

Met Trp Gln Leu Trp Ala Ser Leu Cys Cys Leu Leu Val Leu Ala Asn
1               5                   10                  15

Ala Arg Ser Arg Pro Ser Phe His Pro Leu Ser Asp Glu Leu Val Asn
            20                  25                  30

Tyr Val Asn Lys Arg Asn Thr Thr Trp Gln Ala Gly His Asn Phe Tyr

```
                 35                  40                  45
Asn Val Asp Met Ser Tyr Leu Lys Arg Leu Cys Gly Thr Phe Leu Gly
 50                  55                  60

Gly Pro Lys Pro Pro Gln Arg Val Met Phe Thr Asp Leu Lys Leu
 65                  70                  75                  80

Pro Ala Ser Phe Asp Ala Arg Glu Gln Trp Pro Gln Cys Pro Thr Ile
                     85                  90                  95

Lys Glu Ile Arg Asp Gln Gly Ser Cys Gly Ser Cys Trp Ala Phe Gly
                100                 105                 110

Ala Val Glu Ala Ile Ser Asp Arg Ile Cys Ile His Thr Asn Ala His
                115                 120                 125

Val Ser Val Glu Val Ser Ala Glu Asp Leu Leu Thr Cys Cys Gly Ser
                130                 135                 140

Met Cys Gly Asp Gly Cys Asn Gly Gly Tyr Pro Ala Glu Ala Trp Asn
145                 150                 155                 160

Phe Trp Thr Arg Lys Gly Leu Val Ser Gly Leu Tyr Glu Ser His
                    165                 170                 175

Val Gly Cys Arg Pro Tyr Ser Ile Pro Pro Cys Glu His His Val Asn
                    180                 185                 190

Gly Ser Arg Pro Pro Cys Thr Gly Glu Gly Asp Thr Pro Lys Cys Ser
                    195                 200                 205

Lys Ile Cys Glu Pro Gly Tyr Ser Pro Thr Tyr Lys Gln Asp Lys His
                    210                 215                 220

Tyr Gly Tyr Asn Ser Tyr Ser Val Ser Asn Ser Glu Lys Asp Ile Met
225                 230                 235                 240

Ala Glu Ile Tyr Lys Asn Gly Pro Val Glu Gly Ala Phe Ser Val Tyr
                    245                 250                 255

Ser Asp Phe Leu Leu Tyr Lys Ser Gly Val Tyr Gln His Val Thr Gly
                    260                 265                 270

Glu Met Met Gly Gly His Ala Ile Arg Ile Leu Gly Trp Gly Val Glu
                    275                 280                 285

Asn Gly Thr Pro Tyr Trp Leu Val Ala Asn Ser Trp Asn Thr Asp Trp
                    290                 295                 300

Gly Asp Asn Gly Phe Phe Lys Ile Leu Arg Gly Gln Asp His Cys Gly
305                 310                 315                 320

Ile Glu Ser Glu Val Val Ala Gly Ile Pro Arg Thr Asp Gln Tyr Trp
                    325                 330                 335

Glu Lys Ile

<210> SEQ ID NO 2
<211> LENGTH: 22
<212> TYPE: DNA
<213> ORGANISM: Artificial
<220> FEATURE:
<223> OTHER INFORMATION: CPR-4 forward primer

<400> SEQUENCE: 2
tcggaaagaa ggtctcccag at                                              22

<210> SEQ ID NO 3
<211> LENGTH: 26
<212> TYPE: DNA
<213> ORGANISM: Artificial
<220> FEATURE:
<223> OTHER INFORMATION: cpr-4 reverse primer

<400> SEQUENCE: 3
```

```
ggtagaagtc ctcgtagaca gtgaat                                   26

<210> SEQ ID NO 4
<211> LENGTH: 21
<212> TYPE: DNA
<213> ORGANISM: Artificial
<220> FEATURE:
<223> OTHER INFORMATION: pmp-3 forward primer

<400> SEQUENCE: 4
gttcccgtgt tcatcactca t                                        21

<210> SEQ ID NO 5
<211> LENGTH: 21
<212> TYPE: DNA
<213> ORGANISM: Artificial
<220> FEATURE:
<223> OTHER INFORMATION: pmp-3 reverse primer

<400> SEQUENCE: 5
acaccgtcga gaagctgtag a                                        21
```